United States Patent [19]
Morimoto et al.

[11] Patent Number: 6,030,926
[45] Date of Patent: Feb. 29, 2000

[54] PYRAZOLE DERIVATIVE AND HERBICIDAL COMPOSITION

[75] Inventors: Katsushi Morimoto; Tomoyuki Ogura; Takeshi Nagaoka; Hiroyuki Furusawa; Koichi Nishio; Shigeru Ishii, all of Funabashi; Tsutomu Nawamaki, Shiraoka; Kunimitsu Nakahira, Shiraoka; Kimihiro Ishikawa, Shiraoka, all of Japan

[73] Assignee: Nissan Chemical Industries, Ltd., Tokyo, Japan

[21] Appl. No.: 09/210,890

[22] Filed: Dec. 16, 1998

Related U.S. Application Data

[62] Division of application No. 08/875,499, filed as application No. PCT/JP96/00260, Feb. 7, 1996.

[30] Foreign Application Priority Data

Feb. 7, 1995 [JP] Japan ........................ 7-18981
Jan. 16, 1996 [JP] Japan ........................ 8-04631

[51] Int. Cl.$^7$ .......................... A01N 43/56; C07O 409/06
[52] U.S. Cl. ........................................ 504/280; 548/365.7
[58] Field of Search ........................ 548/365.7; 504/280

[56] References Cited

U.S. PATENT DOCUMENTS 4,008,200  2/1977  Avar et al. .
4,105,851  8/1978  De Wald .

FOREIGN PATENT DOCUMENTS 0 538 156   4/1993   European Pat. Off. .
0 627 423  12/1994   European Pat. Off. .
49-101373   9/1974   Japan .
54-84032    7/1979   Japan .
55-113706   9/1980   Japan .
WO 96/02138 2/1996   WIPO .

OTHER PUBLICATIONS

Butler et al, Chem Abstracts, vol. 75 No. 110225 (1971).
Patent Abstracts of Japan, vol. 95, No. 9, Oct. 31, 1995, JP 07 165724, Jun. 27, 1995.

*Primary Examiner*—Robert W. Ramsuer
*Attorney, Agent, or Firm*—Oblon, Spivak McClelland, Maier & Neustadt, P.C.

[57] ABSTRACT

A pyrazole derivative represented by the general formula (1a) or (1b):

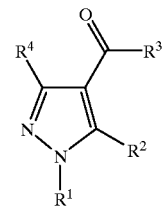

(1a)

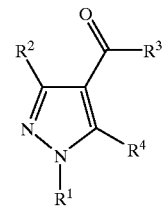

(1b)

wherein
$R^1$ represents a hydrogen atom or a pesticidally acceptable protecting group; $R^2$ and $R^3$ represent a phenyl, 1-naphthyl or 2-naphthyl group, or a 5-6 membered heterocyclic ring and the like; $R^4$ represents a hydrogen or halogen atom, or a alkyl, alkoxy or alkylthio group; and a herbicidal composition containing the pyrazole derivative.

4 Claims, No Drawings

PYRAZOLE DERIVATIVE AND HERBICIDAL COMPOSITION

This application is a Division of application Ser. No. 08/875,499 Filed on Oct. 27, 1997, which is a 371 of PCT/JP96/0026 filed Feb. 7, 1996.

FIELD OF THE INVENTION

The present invention relates to a novel pyrazole derivative and a herbicide comprising the derivative as an active ingredient.

BACKGROUND OF INVENTION

Specific pyrazole derivatives having herbicidal activity are known, for example from JP-A-55-113706. However, they have at 5-position of their pyrazole rings a hydroxyl group or a derivative thereof and consequently have chemical structures completely different from the compounds of the present invention.

In Chemische Berichte, 100 (9), 2885–98 (1967), methyl o-[(3-phenylpyrazol-4-yl)carbonyl]benzoate and o-[(3-phenylpyrazol-4-yl)carbonyl]benzoic acid are described. However, they have carboxylic acid methyl ester or carboxylic acid respectively as a substituent on their benzoyl groups and consequently have chemical structures different from the compounds of the present invention. In addition, no herbicidal activity is referred to in the same publication.

In Journal of Heterocyclic Chemistry, 19, 1355 (1982), 4-benzoyl-1-methyl-5-phenylpyrazole and 4-benzoyl-1-methyl-3-phenylpyrazole are described. However, they have a methyl group as a substituent at 1-position of their pyrazole rings and consequently have chemical structures different from the compounds of the present invention. In addition, no herbicidal activity is referred to in the same publication.

In U.S. Pat. No. 2,721,143, phenylpyrazole derivatives are described. However, they have chemical structures different from the compounds of the present invention. In addition, no herbicidal activity is referred to in the same publication.

In EP-A-538156, phenylpyrazole derivatives comprising a benzoyl group are claimed, which, however, are not concretely disclosed. In addition, no herbicidal activity is referred to in the same publication.

SUMMARY OF THE INVENTION

Taking the above into consideration, the present inventor has continued to study for developing a herbicide and consequently has found:

[1] a pyrazole derivative represented by the general formula (1a) or (1b):

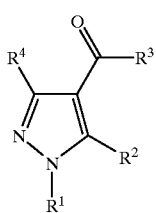

(1a)

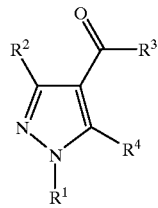

(1b)

wherein
$R^1$ represents a hydrogen atom or a pesticidally acceptable protecting group;
$R^2$ and $R^3$ independently represent:
 a phenyl group which may be substituted with one or more substituents selected from a halogen atom, a $C_{1-4}$ alkyl, $C_{1-4}$ alkoxy, $C_{1-4}$ haloalkyl, $C_{1-4}$ haloalkoxy, di-$C_{1-4}$ alkylamino, cyano, nitro, $C_{1-4}$ alkoxy-carbonyl, phenyl or phenoxy group;
 a 1-naphthyl group which may be substituted with one or more substituents selected from a halogen atom or a $C_{1-4}$ alkyl group;
 a 2-naphthyl group which may be substituted with one or more substituents selected from a halogen atom or a $C_{1-4}$ alkyl group; or
 a 5-6 membered heterocyclic ring which may be substituted with one or more substituents selected from a halogen atom or a $C_{1-4}$ alkyl group;
$R^4$ represents a hydrogen or halogen atom, or a $C_{1-4}$ alkyl, $C_{1-4}$ alkoxy or $C_{1-4}$ alkylthio group;
[2] a pyrazole derivative according to the aforementioned item [1], wherein
$R^1$ represents a hydrogen atom or a $C_{1-4}$ alkoxy $C_{1-4}$ alkyl, $C_{1-3}$ alkoxy-ethoxy-$C_{1-3}$ alkyl, $C_{1-4}$ alkylcarbonyl, benzoyl, $C_{1-4}$ alkoxy-carbonyl, $C_{1-4}$ alkylsulfonyl, di-$C_{1-4}$ alkylsulfamoyl, di-$C_{1-4}$ alkylcarbamoyl or $C_{1-4}$ alkyl-carbamoyl group; and
the 5-6 membered heterocyclic ring represents a thiophen-2-yl, thiophen-3-yl, furan-2-yl, furan-3-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, imidazol-1-yl, imidazol-2-yl, imidazol-4-yl, imidazol-5-yl, isoxazol-3-yl, isoxazol-4-yl, isoxazol-5-yl, isothiazol-3-yl, isothiazol-4-yl, isothiazol-5-yl, pyrazol-1-yl, pyrazol-3-yl, pyrazol-4-yl, pyrazol-5-yl, 1,3,4-oxadiazol-2-yl, 1,3,4-thiadiazol-2-yl, 1,3,4-triazol-1-yl, 1,3,4-triazol-2-yl, 1,2,4-oxadiazol-3-yl, 1,2,4-oxadiazol-5-yl, 1,2,4-thiadiazol-3-yl, 1,2,4-thiadiazol-5-yl, 1,2,4-triazol-1-yl, 1,2,4-triazol-3-yl, 1,2,4-triazol-5-yl, 1,2,3-oxadiazol-4-yl, 1,2,3-oxadiazol-5-yl, 1,2,3-thiadiazol-3-yl, 1,2,3-thiadiazol-5-yl, 1,2,3,4-tetrazol-1-yl, 1,2,3,4-tetrazol-5-yl, 1,2,3,5-tetrazol-1-yl, 1,2,3,5-tetrazol-4-yl, pyridin-2-yl, pyridin-3-yl, pyridin-4-yl, pyrimidin-2-yl, pyrimidin-5-yl, pyrimidin-4-yl, pyrazin-2-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, benzothiophen-2-yl, benzothiophen-3-yl, benzothiophen-4-yl, benzothiophen-5-yl, benzothiophen-6-yl, benzothiophen-7-yl, benzofuran-2-yl, benzofuran-3-yl, benzofuran-4-yl, benzofuran-5-yl, benzofuran-6-yl, benzofuran-7-yl, indol-1-yl, indol-2-yl, indol-3-yl, indol-4-yl, indol-5-yl, indol-6-yl, indol-7-yl, benzoxazol-2-yl, benzoxazol-4-yl, benzoxazol-5-yl, benzoxazol-6-yl, benzoxazol-7-yl, benzothiazol-2- yl, benzothiazol-4-yl, benzothiazol-5-yl, benzothiazol-6-yl, benzothiazol-7-yl, benzimidazol-1-yl, benzimidazol-2-yl, benzimidazol-4-yl, benzimidazol-5-yl, benzimidazol-6-yl, benzimidazol-7-yl, benzisoxazol-3-yl, benzisoxazol-4-yl, benzisoxazol-5-yl, benzisoxazol-6-yl, benzisoxazol-7-yl, benzisothiazol-3-yl, benzisothiazol-4-yl, benzisothiazol-5-yl, benzisothiazol-6-yl, benzisothiazol-7-yl, indazol-1-yl, indazol-3-yl, indazol-4-yl, indazol-5-yl, indazol-6-yl, indazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, quinazolin-2-yl, quinazolin-4-yl, quinazolin-5-yl, quinazolin-6-yl, quinazolin-7-yl, quinazolin-8-yl, quinoxalin-2(or 3)-yl, quinoxalin-5(or 8)-yl, quinoxalin-6(or 7)-yl, phthalazin-1(or 4)-yl, phthalazin-5(or 8)-yl, phthalazin-6(or 7)-yl, cinnolin-3-yl, cinnolin-4-yl, cinnolin-5-yl, cinnolin-6-yl, cinnolin-7-yl, cinnolin-8-yl, 1,2,4-benzotriazin-3-yl, 1,2,4-benzotriazin-5-yl, 1,2,4-benzotriazin-6-yl, 1,2,4-benzotriazin-7-yl or 1,2,4-benzotriazin-8-yl group;

[3] a pyrazole derivative according to the aforementioned item [2], wherein $R^1$ represents a hydrogen atom;

[4] a pyrazole derivative according to the aforementioned item [2], wherein $R^4$ represents a hydrogen atom;

[5] a pyrazole derivative according to the aforementioned item [2], wherein each of $R^1$ and $R^4$ represents a hydrogen atom;

[6] a pyrazole derivative according to the aforementioned item [5], wherein
$R^2$ represents a phenyl or 2-naphthly group which may be substituted with one or more substituents selected from a halogen atom or a $C_{1-4}$ alkyl, $C_{1-4}$ alkoxy, $C_{1-4}$ haloalkyl, $C_{1-4}$ haloalkoxy, di-$C_{1-4}$ alkylamino, cyano, nitro, $C_{1-4}$ alkoxycarbonyl, phenyl or phenoxy group; and
$R^3$ represents a 5-6 membered heterocyclic ring which may be substituted with one or more substituents selected from a halogen atom or a $C_{1-4}$ alkyl group;

[7] a pyrazole derivative according to the aforementioned item [5], wherein
$R^2$ represents a 5-6 membered heterocyclic ring which may be substituted with one or more substituents selected from a halogen atom or a $C_{1-4}$ alkyl group;
$R^3$ represents a phenyl or thiophen-2-yl group;

[8] a pyrazole derivative according to the aforementioned item [5], wherein $R^2$ and $R^3$ independently represent a 5-6 membered heterocyclic ring which may be substituted with one or more substituents selected from a halogen atom or a $C_{1-4}$ alkyl group;

[9] a pyrazole derivative according to the aforementioned item [2], wherein
$R^2$ represents a phenyl or 2-naphthly group which may be substituted with one or more substituents selected from a halogen atom or a $C_{1-4}$ alkyl, $C_{1-4}$ alkoxy, $C_{1-4}$ haloalkyl, $C_{1-4}$ haloalkoxy, di-$C_{1-4}$ alkylamino, cyano, nitro, phenyl or phenoxy group; and
$R^3$ represents a phenyl or thiophen-2-yl group;

[10] a pyrazole derivative according to the aforementioned item [9], wherein $R^1$ represents a hydrogen atom;

[11] a pyrazole derivative according to the aforementioned item [9], wherein $R^4$ represents a hydrogen atom;

[12] a pyrazole derivative according to the aforementioned item [9], wherein each of $R^1$ and $R^4$ represents a hydrogen atom;

[13] a pyrazole derivative according to the aforementioned item [12], wherein $R^2$ represents a 3-substituted-phenyl, 4-substituted-phenyl, 3,4-disubstituted-phenyl, 3,5-disubstituted-phenyl or 3,4,5-trisubstituted-phenyl group which may be substituted with one, two or three substituents selected from a halogen atom or a $C_{1-4}$ alkyl, $C_{1-4}$ alkoxy, $C_{1-4}$ haloalkyl, $C_{1-4}$ haloalkoxy, di-$C_{1-4}$ alkylamino, cyano, nitro, phenyl or phenoxy group; and

[14] a herbicide composition comprising as an active ingredient one or more pyrazole derivatives according to any of the aforementioned items [1] to [13] (hereinafter, referred to as "the compounds of the present invention").

DETAILED DESCRIPTION OF THE INVENTION

The substituents $R^1$, $R^2$, $R^3$ and $R^4$ of the compounds of the present invention are then concretely exemplified in the following.

The abbreviations to be used have the following meanings:

Me: methyl group,
Et: ethyl group,
Pr-n: normal-propyl group,
Pr-iso: iso-propyl group,
Bu-n: normal-butyl group,
Bu-iso: iso-butyl group,
Bu-sec: secondary-butyl group,
Bu-tert: tertiary-butyl group,
Ph: phenyl group.

[Examples of $R^1$ of the compounds of the present invention]

The substituent $R^1$ may be a hydrogen atom or a pesticidally acceptable protecting group which can be easily converted to a hydrogen atom, and is preferably a hydrogen atom.

Examples of the substituent $R^1$ specifically include H, $CH_2OMe$, $CH_2OEt$, $CH_2OPr$-n, $CH_2OPr$-iso, $CH_2OBu$-n, $CH_2OBu$-iso, $CH_2OBu$-sec, $CH_2OBu$-tert, $CH_2CH_2OMe$, $CH_2CH_2OEt$, $CH_2CH_2OPr$-n, $CH_2CH_2CH_2OMe$, $CH_2CH_2CH_2OEt$, $CH_2CH_2CH_2CH_2OMe$, $CH_2OCH_2CH_2OMe$, $CH_2OCH_2CH_2OEt$, $CH_2OCH_2CH_2OPr$-n, $CH_2OCH_2CH_2OPr$-iso, $CH_2CH_2OCH_2CH_2OMe$, $CH_2CH_2OCH_2CH_2OEt$, $CH_2CH_2CH_2OCH_2CH_2OMe$, MeCO, EtCO, (Pr-n)CO, (Bu-n)CO, PhCO, MeOCO, EtOCO, (Pr-n)OCO, (Bu-n)OCO, $MeSO_2$, $EtSO_2$, (Pr-n)$SO_2$, (Bu-n)$SO_2$, $Me_2NSO_2$, $Et_2NSO_2$, (Pr-n)$_2NSO_2$, (Bu-n)$_2NSO_2$, $Me_2NCO$, $Et_2NCO$, (Pr-n)$_2NCO$, (Bu-n)$_2NCO$, MeNHCO, EtNHCO, (Pr-n)NHCO and (Bu-n)NHCO.

[Examples of $R^2$ and $R^3$ of the compounds of the present invention]

The substituent $C_{1-4}$ alkyl group carried on the substituents $R^2$ and $R^3$ may be Me, Et, Pr-n, Pr-iso, Bu-n, Bu-iso, Bu-sec, Bu-tert or the like.

The substituent $C_{1-4}$ alkoxy group carried on the substituents $R^2$ and $R^3$ may be a straight or branched $C_{1-4}$ alkoxy group, such as OMe, OEt, OPr-n, OPr-iso, OBu-n, OBu-iso, OBu-sec and OBu-tert.

The substituent $C_{1-4}$ haloalkyl group carried on the substituents $R^2$ and $R^3$ may be a straight or branched $C_{1-4}$, preferably $C_{1-2}$ alkyl group carrying one to nine, preferably one to five halogen atoms which may be the same or different, such as fluoromethly, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chlorodifluoromethyl, trifluorochloroethyl, chlorobutyl and fluorobutyl groups.

The substituent $C_{1-4}$ haloalkoxy group carried on the substituents $R^2$ and $R^3$ may be a straight or branched $C_{1-4}$, preferably $C_{1-2}$ alkoxy group carrying one to nine, preferably one to five halogen atoms which may be the same or different, such as fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoroisopropoxy, chloroisopropoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy, trifluorochloroethoxy and bromodifluoromethoxy groups.

Examples of the substituents $R^2$ and $R^3$ specifically include Ph, 2-F-Ph, 3-F-Ph, 4-F-Ph, 2,4-F$_2$-Ph, 3,4-F$_2$-Ph, 3,5-F$_2$-Ph, 2,6-F$_2$-Ph, 2,3-F$_2$-Ph, 2,5-F$_2$-Ph, 2,4,6-F$_3$-Ph, 2,3,5-F$_3$-Ph, 2,3,4-F$_3$-Ph, 3,4,5-F$_3$-Ph, 2,4,5-F$_3$-Ph, 2,3,6-F$_3$-Ph, 2,3,4,5-F$_4$-Ph, 2,3,4,6-F$_4$-Ph, 2,3,5,6-F$_4$-Ph, F$_5$-Ph, 2-Cl-Ph, 3-Cl-Ph, 4-Cl-Ph, 2,4-Cl$_2$-Ph, 3,4-Cl$_2$-Ph, 3,5-Cl$_2$-Ph, 2,6-Cl$_2$-Ph, 2,3-Cl$_2$-Ph, 2,5-Cl$_2$-Ph, 2,4,6-Cl$_3$-Ph, 2,3,5-Cl$_3$-Ph, 2,3,4-Cl$_3$-Ph, 3,4,5-Cl$_3$-Ph, 2,4,5-Cl$_3$-Ph, 2,3,6-Cl$_3$-Ph, 2,3,4,5-Cl$_4$-Ph, 2,3,4,6-Cl$_4$-Ph, 2,3,5,6-Cl$_4$-Ph, Cl$_5$-Ph, 2-Br-Ph, 3-Br-Ph, 4-Br-Ph, 2,4-Br$_2$-Ph, 3,4-Br$_2$-Ph, 3,5-Br$_2$-Ph, 2,6-Br$_2$-Ph, 2,3-Br$_2$-Ph, 2,5-Br$_2$-Ph, 2,4,6-Br$_3$-Ph, 2,3,5-Br$_3$-Ph, 2,3,4-Br$_3$-Ph, 3,4,5-Br$_3$-Ph, 2,4,5-Br$_3$-Ph, 2,3,6-Br$_3$-Ph, 2-I-Ph, 3-I-Ph, 4-I-Ph, 2,4-I$_2$-Ph, 3,4-I$_2$-Ph, 3,5-I$_2$-Ph, 2,6-I$_2$-Ph, 2,3-I$_2$-Ph, 2,5-I$_2$-Ph, 2,4,6-I$_3$-Ph, 2,3,5-I$_3$-Ph, 2,3,4-I$_3$-Ph, 3,4,5-I$_3$-Ph, 2,4,5-I$_3$-Ph, 2,3,6-I$_3$-Ph, 2-Cl-3-F-Ph, 2-Cl-4-F-Ph, 2-Cl-5-F-Ph, 2-Cl-6-F-Ph, 3-Cl-2-F-Ph, 3-Cl-4-F-Ph, 3-Cl-5-F-Ph, 3-Cl-6-F-Ph, 4-Cl-2-F-Ph, 4-Cl-3-F-Ph, 2-Br-3-F-Ph, 2-Br-4-F-Ph, 2-Br-5-F-Ph, 2-Br-6-F-Ph, 3-Br-2-F-Ph, 3-Br-4-F-Ph, 3-Br-5-F-Ph, 3-Br-6-F-Ph, 4-Br-2-F-Ph, 4-Br-3-F-Ph, 2-F-3-I-Ph, 2-F-4-I-Ph, 2-F-5-I-Ph, 2-F-6-I-Ph, 3-F-2-I-Ph, 3-F-4-I-Ph, 3-F-5-I-Ph, 3-F-6-I-Ph, 4-F-2-I-Ph, 4-F-3-I-Ph, 2-Br-3-Cl-Ph, 2-Br-4-Cl-Ph, 2-Br-5-Cl-Ph, 2-Br-6-Cl-Ph, 3-Br-2-Cl-Ph, 3-Br-4-Cl-Ph, 3-Br-5-Cl-Ph, 3-Br-6-Cl-Ph, 4-Br-2-Cl-Ph, 4-Br-3-Cl-Ph, 2-Br-3-I-Ph, 2-Br-4-I-Ph, 2-Br-5-I-Ph, 2-Br-6-I-Ph, 3-Br-2-I-Ph, 3-Br-4-I-Ph, 3-Br-5-I-Ph, 3-Br-6-I-Ph, 4-Br-2-I-Ph, 4-Br-3-I-Ph, 2-Cl-3,4-F$_2$-Ph, 2-Cl-3,5-F$_2$-Ph, 2-Cl-3,6-F$_2$-Ph, 2-Cl-4,5-F$_2$-Ph, 2-Cl-4,6-F$_2$-Ph, 2-Cl-5,6-F$_2$-Ph, 3-Cl-2,4-F$_2$-Ph, 3-Cl-2,5-F$_2$-Ph, 3-Cl-2,6-F$_2$-Ph, 3-Cl-4,5-F$_2$-Ph, 3-Cl-4,6-F$_2$-Ph, 3-Cl-5,6-F$_2$-Ph, 4-Cl-2,3-F$_2$-Ph, 4-Cl-2,5-F$_2$-Ph, 4-Cl-2,6-F$_2$-Ph, 4-Cl-3,5-F$_2$-Ph, 3,4-Cl$_2$-2-F-Ph, 3,5-Cl$_2$-2-F-Ph, 2,5-Cl$_2$-6-F-Ph, 3,4-Cl$_2$-6-F-Ph, 2,4-Cl$_2$-6-F-Ph, 2,3-Cl$_2$-6-F-Ph, 2,4-Cl$_2$-3-F-Ph, 2,5-Cl$_2$-3-F-Ph, 2,6-Cl$_2$-3-F-Ph, 3,4-Cl$_2$-5-F-Ph, 2,4-Cl$_2$-5-F-Ph, 2,3-Cl$_2$-5-F-Ph, 2,3-Cl$_2$-4-F-Ph, 2,5-Cl$_2$-4-F-Ph, 2,6-Cl$_2$-4-F-Ph, 3,5-Cl$_2$-4-F-Ph, 2-Br-3,4-F$_2$-Ph, 2-Br-3,5-F$_2$-Ph, 2-Br-3,6-F$_2$-Ph, 2-Br-4,5-F$_2$-Ph, 2-Br-4,6-F$_2$-Ph, 2-Br-5,6-F$_2$-Ph, 3-Br-2,4-F$_2$-Ph, 3-Br-2,5-F$_2$-Ph, 3-Br-2,6-F$_2$-Ph, 3-Br-4,5-F$_2$-Ph, 3-Br-4,6-F$_2$-Ph, 3-Br-5,6-F$_2$-Ph, 4-Br-2,3-F$_2$-Ph, 4-Br-2,5-F$_2$-Ph, 4-Br-2,6-F$_2$-Ph, 4-Br-3,5-F$_2$-Ph, 3,4-Br$_2$-2-F-Ph, 3,5-Br$_2$-2-F-Ph, 2,5-Br$_2$-6-F-Ph, 3,4-Br$_2$-6-F-Ph, 2,4-Br$_2$-6-F-Ph, 2,3-Br$_2$-6-F-Ph, 2,4-Br$_2$-3-F-Ph, 2,5-Br$_2$-3-F-Ph, 2,6-Br$_2$-3-F-Ph, 3,4-Br$_2$-5-F-Ph, 2,4-Br$_2$-5-F-Ph, 2,3-Br$_2$-5-F-Ph, 2,3-Br$_2$-4-F-Ph, 2,5-Br$_2$-4-F-Ph, 2,6-Br$_2$-4-F-Ph, 3,5-Br$_2$-4-F-Ph, 3,4-F$_2$-2-I-Ph, 3,5-F$_2$-2-I-Ph, 2,5-F$_2$-6-I-Ph, 3,4-F$_2$-6-I-Ph, 2,4-F$_2$-6-I-Ph, 2,3-F$_2$-6-I-Ph, 2,4-F$_2$-3-I-Ph, 2,5-F$_2$-3-I-Ph, 2,6-F$_2$-3-I-Ph, 3,4-F$_2$-5-I-Ph, 2,4-F$_2$-5-I-Ph, 2,3-F$_2$-5-I-Ph, 2,3-F$_2$-4-I-Ph, 2,5-F$_2$-4-I-Ph, 2,6-F$_2$-4-I-Ph, 3,5-F$_2$-4-I-Ph, 2-F-3,4-I$_2$-Ph, 2-F-3,5-I$_2$-Ph, 2-F-3,6-I$_2$-Ph, 2-F-4,5-I$_2$-Ph, 2-F-4,6-I$_2$-Ph, 2-F-5,6-I$_2$-Ph, 3-F-2,4-I$_2$-Ph, 3-F-2,5-I$_2$-Ph, 3-F-2,6-I$_2$-Ph, 5-F-3,4-I$_2$-Ph, 5-F-2,4-I$_2$-Ph, 5-F-2,3-I$_2$-Ph, 4-F-2,3-I$_2$-Ph, 4-F-2,5-I$_2$-Ph, 4-F-2,6-I$_2$-Ph, 4-F-3,5-I$_2$-Ph, 2-Br-3,4-cl$_2$-Ph, 2-Br-3,5-Cl$_2$-Ph, 2-Br-3,6-Cl$_2$-Ph, 2-Br-4,5-Cl$_2$-Ph, 6-Br-2,4-Cl$_2$-Ph, 6-Br-2,3-Cl$_2$-Ph, 3-Br-2,4-Cl$_2$-Ph, 3-Br-2,5-Cl$_2$-Ph, 3-Br-2,6-Cl$_2$-Ph, 3-Br-4,5-Cl$_2$-Ph, 5-Br-2,4-Cl$_2$-Ph, 5-Br-2,3-Cl$_2$-Ph, 4-Br-2,3-Cl$_2$-Ph, 4-Br-2,5-Cl$_2$-Ph, 4-Br-2,6-Cl$_2$-Ph, 4-Br-3,5-Cl$_2$-Ph, 3,4-Br$_2$-2-Cl-Ph, 3,5-Br$_2$-2-Cl-Ph, 2,5-Br$_2$-6-Cl-Ph, 3,4-Br$_2$-6-Cl-Ph, 2,4-Br$_2$-6-Cl-Ph, 2,3-Br$_2$-6-Cl-Ph, 2,4-Br$_2$-3-Cl-Ph, 2,5-Br$_2$-3-Cl-Ph, 2,6-Br$_2$-3-Cl-Ph, 3,4-Br$_2$-5-Cl-Ph, 2,4-Br$_2$-5-Cl-Ph, 2,3-Br$_2$-5-Cl-Ph, 2,3-Br$_2$-4-Cl-Ph, 2,5-Br$_2$-4-Cl-Ph, 2,6-Br$_2$-4-Cl-Ph, 3,5-Br$_2$-4-Cl-Ph, 3,4-Cl$_2$-2-I-Ph, 3,5-Cl$_2$-2-I-Ph, 2,5-Cl$_2$-6-I-Ph, 3,4-Cl$_2$-6-I-Ph, 2,4-Cl$_2$-6-I-Ph, 2,3-Cl$_2$-6-I-Ph, 2,4-Cl$_2$-3-I-Ph, 2,5-Cl$_2$-3-I-Ph, 2,6-Cl$_2$-3-I-Ph, 3,4-Cl$_2$-5-I-Ph, 2,4-Cl$_2$-5-I-Ph, 2,3-Cl$_2$-5-I-Ph, 2,3-Cl$_2$-4-I-Ph, 2,5-Cl$_2$-4-I-Ph, 2,6-Cl$_2$-4-I-Ph, 3,5-Cl$_2$-4-I-Ph, 2-Cl-3,4-I$_2$-Ph, 2-Cl-3,5-I$_2$-Ph, 2-Cl-3,6-I$_2$-Ph, 2-Cl-4,5-I$_2$-Ph, 2-Cl-4,6-I$_2$-Ph, 2-Cl-5,6-I$_2$-Ph, 3-Cl-2,4-I$_2$-Ph, 3-Cl-2,5-I$_2$-Ph, 3-Cl-2,6-I2-Ph, 3-Cl-4,5-I$_2$-Ph, 3-Cl-4,6-I$_2$-Ph, 3-Cl-5,6-I$_2$-Ph, 4-Cl-2,3-I$_2$-Ph, 4-Cl-2,5-I$_2$-Ph, 4-Cl-2,6-I$_2$-Ph, 4-Cl-3,5-I$_2$-Ph, 3,4-Br$_2$-2-I-Ph, 3,5-Br$_2$-2-I-Ph, 2,5-Br$_2$-6-I-Ph, 3,4-Br$_2$-6-I-Ph, 2,4-Br$_2$-6-I-Ph, 2,3-Br$_2$-6-I-Ph, 2,4-Br$_2$-3-I-Ph, 2,5-Br$_2$-3-I-Ph, 2,6-Br$_2$-3-I-Ph, 3,4-Br$_2$-5-I-Ph, 2,4-Br$_2$-5-I-Ph, 2,3-Br$_2$-5-I-Ph, 2,3-Br$_2$-4-I-Ph, 2,5-Br$_2$-4-I-Ph, 2,6-Br$_2$-4-I-Ph, 3,5-Br$_2$-4-I-Ph, 2-Br-3,4-I$_2$-Ph, 2-Br-3,5-I$_2$-Ph, 2-Br-3,6-I$_2$-Ph, 2-Br-4,5-I$_2$-Ph, 2-Br-4,6-I$_2$-Ph, 2-Br-5,6-I$_2$-Ph, 3-Br-2,4-I$_2$-Ph, 3-Br-2,5-I$_2$-Ph, 3-Br-2,6-I$_2$-Ph, 3-Br-4,5-I$_2$-Ph, 3-Br-4,6-I$_2$-Ph, 3-Br-5,6-I$_2$-Ph, 4-Br-2,3-I$_2$-Ph, 4-Br-2,5-I$_2$-Ph, 4-Br-2,6-I$_2$-Ph, 4-Br-3,5-1$_2$-Ph, 2-Cl-3,4,5-F$_3$-Ph, 2-Cl-3,4,6-F$_3$-Ph, 2-Cl-3,5,6-F$_3$-Ph, 6-Cl-2,3,4-F$_3$-Ph, 3-Cl-2,4,5-F$_3$-Ph, 3-Cl-2,4,6-F$_3$-Ph, 5-Cl-2,3,6-F$_3$-Ph, 5-Cl-2,3,4-F$_3$-Ph, 4-Cl-2,3,5-F$_3$-Ph, 4-Cl-2,3,6-F$_3$-Ph, 2,3-Cl$_2$-4,5-F$_2$-Ph, 2,3-Cl$_2$-5,6-F$_2$-Ph, 2,3-Cl$_2$-4,6-F$_2$-Ph, 2,4-Cl$_2$-3,5-F$_2$-Ph, 2,4-Cl$_2$-3,6-F$_2$-Ph, 4,6-Cl$_2$-2,3-F$_2$-Ph, 2,5-Cl$_2$-3,4-F$_2$-Ph, 2,5-Cl$_2$-3,6-F$_2$-Ph, 3,6-Cl$_2$-2,4-F$_2$-Ph, 2,6-Cl$_2$-3,5-F$_2$-Ph, 3,5-Cl$_2$-2,4-F$_2$-Ph, 3,5-Cl$_2$-2,6-F$_2$-Ph, 3,4,5-Cl$_3$-2,6-F$_2$-Ph, 3,4,5-Cl$_3$-2-F-Ph, 3,4,6-Cl$_3$-2-F-Ph, 3,5,6-Cl$_3$-2-F-Ph, 2,3,4-Cl$_3$-6-F-Ph, 2,4,5-Cl$_3$-3-F-Ph, 2,4,6-Cl$_3$-3-F-Ph, 2,5,6-Cl$_3$-3-F-Ph, 2,3,4-Cl$_3$-5-F-Ph, 2,3,5-Cl$_3$-4-F-Ph, 2,3,6-Cl$_3$-4-F-Ph, 2-Br-3,4,5-F$_3$-Ph, 2-Br-3,4,6-F$_3$-Ph, 2-Br-3,5,6-F$_3$-Ph, 6-Br-2,3,4-F$_3$-Ph, 3-Br-2,4,5-F$_3$-Ph, 3-Br-2,4,6-F$_3$-Ph, 5-Br-2,3,6-F$_3$-Ph, 5-Br-2,3,4-F$_3$-Ph, 4-Br-2,3,5-F$_3$-Ph, 4-Br-2,3,6-F$_3$-Ph, 2,3-Br$_2$-4,5-F$_2$-Ph, 2,3-Br$_2$-5,6-F$_2$-Ph, 2,3-Br$_2$-4,6-F$_2$-Ph, 2,4-Br$_2$-3,5-F$_2$-Ph, 2,4-Br$_2$-3,6-F$_2$-Ph, 4,6-Br$_2$-2,3-F$_2$-Ph, 2,5-Br$_2$-3,4-F$_2$-Ph, 2,5-Br$_2$-3,6-F$_2$-Ph, 3,6-Br$_2$-2,4-F$_2$-Ph, 2,6-Br$_2$-3,4-F$_2$-Ph, 2,6-Br$_2$-3,5-F$_2$-Ph, 3,5-Br$_2$-2,4-F$_2$-Ph, 3,5-Br$_2$-2,6-F$_2$-Ph, 3,4,5-Br$_3$-2-F-Ph, 3,4,6-Br$_3$-2-F-Ph, 3,5,6-Br$_3$-2-F-Ph, 2,3,4-Br$_3$-6-F-Ph, 2,4,5-Br$_3$-3-F-Ph, 2,4,6-Br$_3$-3-F-Ph, 2,5,6-Br$_3$-3-F-Ph, 2,3,4-Br$_3$-5-F-Ph, 2,3,5-Br$_3$-4-F-Ph, 2,3,6-Br$_3$-4-F-Ph, 3,4,5-F$_3$-2-I-Ph, 3,4,6-F$_3$-2-I-Ph, 3,5,6-F$_3$-2-I-Ph, 2,3,4-F$_3$-6-I-Ph, 2,4,5-F$_3$-3-I-Ph, 2,4,6-F$_3$-3-I-Ph, 2,5,6-F$_3$-3-I-Ph, 2,3,4-F$_3$-5-I-Ph, 2,3,5-F$_3$-4-I-Ph, 2,3,6-F$_3$-4-I-Ph, 2,3-F$_2$-4,5-I$_2$-Ph, 2,3-F$_2$-5,6-I$_2$-Ph, 2,3-F$_2$-4,6-I$_2$-Ph, 2,4-F$_2$-3,5-I2-Ph, 2,4-F$_2$-3,6-I$_2$-Ph, 4,6-F$_2$-2,3-I$_2$-Ph, 2,5-F$_2$-3,4-I$_2$-Ph, 2,5-F$_2$-3,6-I$_2$-Ph, 3,6-F$_2$-2,4-I$_2$-Ph, 2,6-F$_2$-3,4-I$_2$-Ph, 2,6-F$_2$-3,5-I$_2$-Ph, 3,5-F$_2$-2,4-I$_2$-Ph, 3,5-F$_2$-2,6-I$_2$-Ph, 2-F-3,4,5-I$_3$-Ph, 2-F-3,4,6-I$_3$-Ph, 2-F-3,5,6-I$_3$-Ph, 6-F-2,3,4-I$_3$-Ph, 3-F-2,4,5-I$_3$-Ph, 3-F-2,4,6-I$_3$-Ph, 5-F-2,3,6-I$_3$-Ph, 5-F-2,3,4-I$_3$-Ph, 4-F-2,3,5-I$_3$-Ph, 4-F-2,3,6-I$_3$-Ph, 2-Br-3,4,5-Cl$_3$-Ph, 2-Br-3,4,6-Cl$_3$-Ph, 2-Br-3,5,6-Cl$_3$-Ph, 6-Br-2,3,4-Cl$_3$-Ph, 3-Br-2,4,5-Cl$_3$-Ph, 3-Br-2,4,6-Cl$_3$-Ph, 5-Br-2,3,6-Cl$_3$-Ph, 5-Br-2,3,4-Cl$_3$-Ph, 4-Br-2,3,5-Cl$_3$-Ph, 4-Br-2,3,6-Cl$_3$-Ph, 2,3-Br$_2$-4,5-Cl$_2$-Ph, 2,3-Br$_2$-5,6-Cl$_2$-Ph, 2,3-Br$_2$-4,6-Cl$_2$-Ph, 2,4-Br$_2$-3, 5-Cl$_2$-Ph, 2,4-Br$_2$-3,6-Cl$_2$-Ph, 4,6-Br$_2$-2,3-Cl$_2$-Ph, 2,5-Br$_2$-3,4-Cl$_2$-Ph, 2,5-Br$_2$-3,6-Cl$_2$-Ph, 3,6-Br$_2$-2,4-Cl$_2$-Ph, 2,6-Br$_2$-3,4-Cl$_2$-Ph, 2,6-Br$_2$-3,5-Cl$_2$-Ph, 3,5-Br$_2$-2,4-Cl$_2$-Ph, 3,5-Br$_2$-2,6-Cl$_2$-Ph, 3,4,5-Br$_3$-2-Cl-Ph, 3,4,6-Br$_3$-2-Cl-Ph, 3,5,6-Br$_3$-2-Cl-Ph, 2,3,4-Br$_3$-6-Cl-Ph, 2,4,5-Br$_3$-3-Cl-Ph, 2,4,6-Br$_3$-3-Cl-Ph, 2,5,6-Br$_3$-3-Cl-Ph, 2,3,4-Br$_3$-5-Cl-Ph, 2,3,5-Br$_3$-4-Cl-Ph, 2,3,6-Br$_3$-4-Cl-Ph, 3,4,5-Cl$_3$-2-I-Ph, 3,4,6-cl$_3$-2-I-Ph, 3,5,6-Cl$_3$-2-I-Ph, 2,3,4-Cl$_3$-6-I-Ph, 2,4,5-Cl$_3$-3-I-Ph, 2,4,6-Cl$_3$-3-I-Ph, 2,5,6-Cl$_3$-3-I-Ph, 2,3,4-Cl$_3$-5-I-Ph, 2,3,5-Cl$_3$-4-I-Ph, 2,3,6-Cl$_3$-4-I-Ph, 2,3-Cl$_2$-4,5-I$_2$-Ph, 2,3-Cl$_2$-5,6-I$_2$-Ph, 2,3-Cl$_2$-4,6-I$_2$-Ph, 2,4-Cl$_2$-3,5-I$_2$-Ph, 2,4-Cl$_2$-3,6-I$_2$-Ph, 4,6-Cl$_2$-2,3-I$_2$-Ph, 2,5-Cl$_2$-3,4-I$_2$-Ph, 2,5-Cl$_2$-3,6-I$_2$-Ph, 3,6-Cl$_2$-2,4-I$_2$-Ph, 2,6-Cl$_2$-3,4-I$_2$-Ph, 2,6-Cl$_2$-3,5-I$_2$-Ph, 3,5-Cl$_2$-2,4-I$_2$-Ph, 3,5-Cl$_2$-2,6-I$_2$-Ph, 3,4,5-Br$_3$-2-I-Ph, 3,4,6-Br$_3$-2-I-Ph, 3,5,6-Br$_3$-2-I-Ph, 2,3,4-Br$_3$-6-I-Ph, 2,4,5-Br$_3$-3-I-Ph, 2,4,6-Br$_3$-3-I-Ph, 2,5,6-Br$_3$-3-I-Ph, 2,3,4-Br$_3$-5-I-Ph, 2,3,5-Br$_3$-4-I-Ph, 2,3,6-Br$_3$-4-I-Ph, 2,3-Br$_2$-4,5-I$_2$-Ph, 2,3-Br$_2$-5,6-I$_2$-Ph, 2,3-Br$_2$-4,6-I$_2$-Ph, 2,4-Br$_2$-3,5-I$_2$-Ph, 2,4-Br$_2$-3,6-I$_2$-Ph, 4,6-Br$_2$-2,3-I$_2$-Ph, 2,5-Br$_2$-3,4-I$_2$-Ph, 2,5-Br$_2$-3,6-I$_2$-Ph, 3,6-Br$_2$-2,4-I$_2$-Ph, 2,6-Br$_2$-3,4-I$_2$-Ph, 2,6-Br$_2$-3,5-I$_2$-Ph, 3,5-Br$_2$-2,4-I$_2$-Ph, 3,5-Br$_2$-2,6-I$_2$-Ph, 2-Cl-3,4,5,6-F$_4$-Ph, 3-Cl-2,4,5,6-F$_4$-Ph, 4-Cl-2,3,5,6-F$_4$-Ph, 2,4-Cl$_2$-3,5,6-F$_3$-Ph, 3,4-Cl$_2$-2,5,6-F$_3$-Ph, 3,5-Cl$_2$-2,4,6-F$_3$-Ph, 2,6-Cl$_2$-3,4,5-F$_3$-Ph, 2,3-Cl$_2$-4,5,6-F$_3$-Ph, 2,5-Cl$_2$-3,4,6-F$_3$-Ph, 2,4,6-Cl$_3$-3,5-F$_2$-Ph, 2,3,5-Cl$_3$-4,6-F$_2$-Ph, 2,3,4-Cl$_3$-5,6-F$_2$-Ph, 3,4,5-Cl$_3$-2,6-F$_2$-Ph, 2,4,5-Cl$_3$-3,6-F$_2$-Ph, 2,3,6-Cl$_3$-4,5-F$_2$-Ph, 2,3,4,5-Cl$_4$-6-F-Ph, 2,3,4,6-Cl$_4$-5-F-Ph, 2,3,5,6-Cl$_4$-4-F-Ph, 2-Br-3,4,5,6-F$_4$-Ph, 3-Br-2,4,5,6-F$_4$-Ph, 4-Br-2,3,5,6-F$_4$-Ph, 2,4-Br$_2$-3,5,6-F$_3$-Ph, 3,4-Br$_2$-2,5,6-F$_3$-Ph, 3,5-Br$_2$-2,4,6-F$_3$-Ph, 2,6-Br$_2$-3,4,5-F$_3$-Ph, 2,3-Br$_2$-4,5,6-F$_3$-Ph, 2,5-Br$_2$-3,4,6-F$_3$-Ph, 2,4,6-Br$_3$-3,5-F$_2$-Ph, 2,3,5-Br$_3$-4,6-F$_2$-Ph, 2,3,4-Br$_3$-5,6-F$_2$-Ph, 3,4,5-Br$_3$-2,6-F$_2$-Ph, 2,4,5-Br$_3$-3,6-F$_2$-Ph, 2,3,6-Br$_3$-4,5-F$_2$-Ph, 2,3,4,5-Br$_4$-6-F-Ph, 2,3,4,6-Br$_4$-5-F-Ph, 2,3,5,6-Br$_4$-4-F-Ph, 2-I-3,4,5,6-F$_4$-Ph, 3-I-2,4,5,6-F$_4$-Ph, 4-I-2,3,5,6-F$_4$-Ph, 2-Br-3,4,5,6-Cl$_4$-Ph, 3-Br-2,4,5,6-Cl$_4$-Ph, 4-Br-2,3,5,6-Cl$_4$-Ph, 2,4-Br$_2$-3,5,6-Cl$_3$-Ph, 3,4-Br$_2$-2,5,6-Cl$_3$-Ph, 3,5-Br$_2$-2,4,6-Cl$_3$-Ph, 2,6-Br$_2$-3,4,5-Cl$_3$-Ph, 2,3-Br$_2$-4,5,6-Cl$_3$-Ph, 2,5-Br$_2$-3,4,6-Cl$_3$-Ph, 2,4,6-Br$_3$-3,5-Cl$_2$-Ph, 2,3,5-Br$_3$-4,6-Cl$_2$-Ph, 2,3,4-Br$_3$-5,6-Cl$_2$-Ph, 3,4,5-Br$_3$-2,6-Cl$_2$-Ph, 2,4,5-Br$_3$-3,6-Cl$_2$-Ph, 2,3,6-Br$_3$-4,5-Cl$_2$-Ph, 2-Me-Ph, 3-Me-Ph, 4-Me-Ph, 2,4-Me$_2$-Ph, 3,5-Me$_2$-Ph, 2,6-Me$_2$-Ph, 2,3-Me$_2$-Ph, 3,4-Me$_2$-Ph, 2,5-Me$_2$-Ph, 2-Et-Ph, 3-Et-Ph, 4-Et-Ph, 2-(Pr-n)-Ph, 3-(Pr-n)-Ph, 4-(Pr-n)-Ph, 3-(Pr-iso)-Ph, 4-(Pr-iso)-Ph, 3-(Bu-n)-Ph, 4-(Bu-n)-Ph, 3-(Bu-tert)-Ph, 4-(Bu-tert)-Ph, 3-(Bu-iso)-Ph, 3-(Bu-sec)-Ph, 4-F-3-Me-Ph, 3-F-4-Me-Ph, 4-Cl-3-Me-Ph, 3-Cl-4-Me-Ph, 4-Br-3-Me-Ph, 3-Br-4-Me-Ph, 4-F-3,5-Me$_2$-Ph, 4-Cl-3,5-Me$_2$-Ph, 4-Br-3,5-Me$_2$-Ph, 2-MeO-Ph, 3-MeO-Ph, 4-MeO-Ph, 3-EtO-Ph, 3-(OPr-iso)-Ph, 4-(OPr-iso)-Ph, 3-(OBu-n)-Ph, 4-(OBu-n)-Ph, 3-(OBu-iso)-Ph, 3-(OBu-tert)-Ph, 3,4,5-(MeO)$_3$-Ph, 3,4,5-(EtO)$_3$-Ph, 4-F-3-MeO-Ph, 3-F-4-MeO-Ph, 4-Cl-3-MeO-Ph, 3-Cl-4-MeO-Ph, 4-Cl-2-MeO-Ph, 5-Cl-2-MeO-Ph, 3,4-(MeO)$_2$-Ph, 4-Br-3-MeO-Ph, 3-Br-4-MeO-Ph, 4-F-3,5-(MeO)$_2$-Ph, 4-Cl-3,5-(MeO)$_2$-Ph, 4-Br-3,5-(MeO)$_2$-Ph, 2-CF$_3$-Ph, 3-CF$_3$-Ph, 4-CF$_3$-Ph, 3-F-5-CF$_3$-Ph, 3-Cl-4-CF$_3$-Ph, 2,4-(CF$_3$)$_2$-Ph, 3,5-(CF$_3$)$_2$-Ph, 2,6-(CF$_3$)$_2$-Ph, 2,3-(CF$_3$)$_2$-Ph, 2,5-(CF$_3$)$_2$-Ph, 4-F-3,5-(CF$_3$)$_2$-Ph, 4-Cl-3,5-(CF$_3$)$_2$-Ph, 4-Br-3,5-(CF$_3$)$_2$-Ph, 3-CH$_2$F-Ph, 3-CH$_2$Cl-Ph, 3-CH$_2$Br-Ph, 3-CH$_2$I-Ph, 3-CHF$_2$-Ph, 3-CHCl$_2$-Ph, 3-CCl$_3$-Ph, 3-CH$_2$CH$_2$F-Ph, 3-CH$_2$CH$_2$Cl-Ph, 3-CH$_2$CH$_2$Br-Ph, 3-CF$_2$Cl-Ph, 3-CH$_2$CF$_3$-Ph, 3-CF$_2$CF$_2$Br-Ph, 3-CF$_2$CF$_2$CF$_3$-Ph, 3-CF$_2$CF$_2$CF$_2$CF$_3$-Ph, 4CH$_2$F-Ph, 4-CH$_2$Cl-Ph, 4-CH$_2$Br-Ph, 4-CH$_2$I-Ph, 4-CHF$_2$-Ph, 4-CHCl$_2$-Ph, 4-CCl$_3$-Ph, 4-CH$_2$CH$_2$F-Ph, 4-CH$_2$CH$_2$Cl-Ph, 4-CH$_2$CH$_2$Br-Ph, 4-CF$_2$Cl-Ph, 4-CH$_2$CF$_3$-Ph, 4-CF$_2$CF$_2$CF$_3$-Ph, 4-CF$_2$CF$_2$CF$_2$CF$_3$-Ph, 3-OCH$_2$F-Ph, 3-OCHF$_2$-Ph, 3-OCF$_3$-Ph, 3-OCClF$_2$-Ph, 3-OCBrF$_2$-Ph, 3-OCF$_2$CHF$_2$-Ph, 3-OCH$_2$CH$_2$F-Ph, 3-OCH$_2$CH$_2$Cl-Ph, 3-OCH$_2$CH$_2$Br-Ph, 3-OCH$_2$CH$_2$I-Ph, 3-OCH$_2$CF$_3$-Ph, 3-OCH$_2$CCl$_3$-Ph, 3-OCF(CH$_3$)$_2$-Ph, 3-OCH$_2$CH$_2$CH$_2$CH$_2$F-Ph, 4-OCH$_2$F-Ph, 4-OCHF$_2$-Ph, 4-OCF$_3$-Ph, 4-OCClF$_2$-Ph, 4-OCBrF$_2$-Ph, 4-OCF$_2$CHF$_2$-Ph, 4-OCH$_2$CH$_2$F-Ph, 4-OCH$_2$CH$_2$Cl-Ph, 4-OCH$_2$CH$_2$Br-Ph, 4-OCH$_2$CH$_2$I-Ph, 4-OCH$_2$CF$_3$-Ph, 4-OCH$_2$CCl$_3$-Ph, 4-OCF(CH$_3$)$_2$-Ph, 4-OCH$_2$CH$_2$CH$_2$CH$_2$F-Ph, 2-Me$_2$N-Ph, 3-Me$_2$N-Ph, 4-Me$_2$N-Ph, 3,5-(Me$_2$N)$_2$-Ph, 4-F-3,5-(Me$_2$N)$_2$-Ph, 4-Cl-3,5-(Me$_2$N)$_2$-Ph, 4-Br-3,5-(Me$_2$N)2-Ph, 3-Et$_2$N-Ph, 4-(Pr-n)$_2$N-Ph, 3-(Bu-n)$_2$N-Ph, 3-(Pr-iso)$_2$N-Ph, 2-NO$_2$-Ph, 3-NO$_2$-Ph, 4-NO$_2$-Ph, 3,5-(NO$_2$)$_2$-Ph, 4-F-3,5-(NO$_2$)$_2$-Ph, 4-Cl-3,5-(NO$_2$)$_2$-Ph, 2-Cl-3,5-(NO$_2$)$_2$-Ph, 2,4-Cl$_2$-3,5-(NO$_2$)$_2$-Ph, 4-Br-3,5-(NO$_2$)$_2$-Ph, 4-Me-3-NO$_2$-Ph, 2-Cl-3-NO$_2$-Ph, 2-Cl-4-NO$_2$-Ph, 4-Cl-2-NO$_2$-Ph, 5-Cl-2-NO$_2$-Ph, 4-Cl-3-NO$_2$-Ph, 4-MeO-3-NO$_2$-Ph, 2-CN-Ph, 3-CN-Ph, 4-CN-Ph, 4-F-3-CN-Ph, 4-Cl-3-CN-Ph, 3,5-(CN)$_2$-Ph, 4-F-3,5-(CN)$_2$-Ph, 4-Cl-3,5-(CN)$_2$-Ph, 4-Br-3,5-(CN)$_2$-Ph, 2-CO$_2$Me-Ph, 3-CO$_2$Me-Ph, 4-CO$_2$Me-Ph, 4-F-3-CO$_2$Me-Ph, 4-Cl-3-CO$_2$Me-Ph, 4-F-3,5-(CO$_2$Me)$_2$-Ph, 4-Cl-3,5-(CO$_2$Me)$_2$-Ph, 2-Ph-Ph, 3-Ph-Ph, 4-Ph-Ph, 2,4-Ph$_2$-Ph, 3,5-Ph$_2$-Ph, 2,6-Ph$_2$-Ph, 2,3-Ph$_2$-Ph, 2,5-Ph$_2$-Ph, 4-F-3-Ph-Ph, 3-F-4-Ph-Ph, 4-Cl-3-Ph-Ph, 3-Cl-4-Ph-Ph, 4-Br-3-Ph-Ph, 3-Br-4-Ph-Ph, 4-F-3,5-Ph$_2$-Ph, 4-Cl-3,5-Ph$_2$-Ph, 4-Br-3,5-Ph$_2$-Ph, 2-PhO-Ph, 3-PhO-Ph, 4-PhO-Ph, 2,4-(PhO)$_2$-Ph, 3,5-(PhO)$_2$-Ph, 2,6-(PhO)$_2$-Ph, 2,3-(PhO)$_2$-Ph, 2,5-(PhO)$_2$-Ph, 4-Cl-3-PhO-Ph, 4-F-3-PhO-Ph, 3-F-4-PhO-Ph, 4-Cl-3-PhO-Ph, 3-Cl-4-PhO-Ph, 4-Br-3-PhO-Ph, 3-Br-4-PhO-Ph, 4-F-3,5-(PhO)$_2$-Ph, 4-Cl-3,5-(PhO)$_2$-Ph, 4-Br-3,5-(PhO)$_2$-Ph, thiophen-2-yl, 5-chlorothiophen-2-yl, thiophen-3-yl, furan-2-yl, furan-3-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, imidazol-1-1, imidazol-2-yl, imidazol-4-yl, imidazol-5-yl, isoxazol-3-yl, isoxazol-4-yl, isoxazol-5-yl, isothiazol-3-yl, isothiazol-4-yl, isothiazol-5-yl, pyrazol-1-yl, pyrazol-3-yl, pyrazol-4-yl, pyrazol-5-yl, 1,3,4-oxadiazol-2-yl, 1,3,4-thiadiazol-2-yl, 1,3,4-triazol-1-yl, 1,3,4-triazol-2-yl, 1,2,4-oxadiazol-3-yl, 1,2,4-oxadiazol-5-yl, 1,2,4-thiadiazol-3-yl, 1,2,4-thiadiazol-5-yl, 1,2,4-triazol-1-yl, 1,2,4-triazol-3-yl, 1,2,4-triazol-5-yl, 1,2,3-oxadiazol-4-yl, 1,2,3-oxadiazol-5-yl, 1,2,3-thiadiazol-3-yl, 1,2,3-thiadiazol-5-yl, 1,2,3,4-tetrazol-1-yl, 1,2,3,4-tetrazol-5-yl, 1,2,3,5-tetrazol-1-yl, 1,2,3,5-tetrazol-4-yl, pyridin-2-yl, pyridin-3-yl, pyridin-4-yl, pyrimidin-2-yl, pyrimidin-5-yl, pyrimidin-4-yl, pyrazin-2-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, benzothiophen-2-yl, benzothiophen-3-yl, benzothiophen-4-yl, benzothiophen-5-yl, benzothiophen-6-yl, benzothiophen-7-yl, benzofuran-2-yl, benzofuran-3-yl, benzofuran-4-yl, benzofuran-5-yl, benzofuran-6-yl, benzofuran-7-yl, indol-1-yl, indol-2-yl, indol-3-yl, indol-4-yl, indol-5-yl, indol-6-yl, indol-7-yl, benzoxazol-2-yl, benzoxazol-4-yl, benzoxazol-5-yl, benzoxazol-6-yl, benzoxazol-7-yl, benzothiazol-2-yl, benzothiazol-4-yl, benzothiazol-5-yl, benzothiazol-6-yl, benzothiazol-7-yl, benzimidazol-1-yl, benzimidazol-2-yl, benzimidazol-4-yl, benzimidazol-5-yl, benzimidazol-6-yl, benzimidazol-7-yl, benzisoxazol-3-yl, benzisoxazol-4-yl, benzisoxazol-5-yl, benzisoxazol-6-yl, benzisoxazol-7-yl, benzisothiazol-3-yl, benzisothiazol-4-yl, benzisothiazol-5-yl, benzisothiazol-6-yl, benzisothiazol-7-yl, indazol-1-yl, indazol-3-yl, indazol-4-yl, indazol-5-yl, indazol-6-yl, indazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, quinazolin-2-yl, quinazolin-4-yl, quinazolin-5-yl, quinazolin-6-yl, quinazolin-7-yl, quinazolin-8-yl, quinoxalin-2(or 3)-yl, quinoxalin-5(or 8)-yl, quinoxalin-6(or 7)-yl, phthalazin-1(or 4)-yl, phthalazin-5(or 8)-yl, phthalazin-6(or 7)-yl, cinnolin-3-yl, cinnolin-4-yl, cinnolin-5-yl, cinnolin-6-yl, cinnolin-7-yl, cinnolin-8-yl, 1,2,4-benzotriazin-3-yl, 1,2,4-benzotriazin-5-yl, 1,2,4-benzotriazin-6-yl, 1,2,4-benzotriazin-7-yl, 1,2,4-benzotriazin-8-yl, 1-methyl-3,5-dichloropyrazol-4-yl, 1-methyl-5-chloropyrazol-4-yl and 2,6-dichloropyridin-4-yl.

Preferable examples of the substituent $R^2$ include 3-F-Ph, 4-F-Ph, 3,4-F$_2$-Ph, 3,5-F$_2$-Ph, 3,4,5-F$_3$-Ph, 3-Cl-Ph, 4-Cl-Ph, 3,4-Cl$_2$-Ph, 3,5-Cl$_2$-Ph, 3,4,5-Cl$_3$-Ph, 3-Br-Ph, 4-Br-Ph, 3,4-Br$_2$-Ph, 3,5-Br$_2$-Ph, 3,4,5-Br$_3$-Ph, 3-I-Ph, 4-I-Ph, 3,4-I$_2$-Ph, 3,5-I$_2$-Ph, 3,4,5-I$_3$-Ph, 3-Cl-4-F-Ph, 3-Cl-5-F-Ph, 4-Cl-3-F-Ph, 3-Br-4-F-Ph, 3-Br-5-F-Ph, 4-Br-3-F-Ph, 3-F-4-I-Ph, 3-F-5-I-Ph, 4-F-3-I-Ph, 3-Br-4-Cl-Ph, 3-Br-5-Cl-Ph, 4-Br-3-Cl-Ph, 3-Br-4-I-Ph, 3-Br-5-I-Ph, 4-Br-3-I-Ph, 3-Cl-4,5-F$_2$-Ph, 4-Cl-3,5-F$_2$-Ph, 3,4-Cl$_2$-5-F-Ph, 3,5-Cl$_2$-4-F-Ph, 3-Br-4,5-F$_2$-Ph, 4-Br-3,5-F$_2$-Ph, 3,4-Br$_2$-5-F-Ph, 3,5-Br$_2$-4-F-Ph, 3,4-F$_2$-5-I-Ph, 3,5-F$_2$-4-I-Ph, 5-F-3,4-I$_2$-Ph, 4-F-3,5-I$_2$-Ph, 3-Br-4,5-Cl$_2$-Ph, 4-Br-3,5-Cl$_2$-Ph, 3,4-Br$_2$-5-Cl-Ph, 3,5-Br$_2$-4-Cl-Ph, 3,4-Cl$_2$-5-I-Ph, 3,5-Cl$_2$-4-I-Ph, 3-Cl-4,5-I$_2$-Ph, 4-Cl-3,5-I$_2$-Ph, 3,4-Br$_2$-5-I-Ph, 3,5-Br$_2$-4-I-Ph, 3-Br-4,5-I$_2$-Ph, 4-Br-3,5-I$_2$-Ph, 3-Me-Ph, 4-Me-Ph, 3,5-Me$_2$-Ph, 3,4-Me$_2$-Ph, 3-Et-Ph, 4-Et-Ph, 3-(Pr-n)-Ph, 4-(Pr-n)-Ph, 3-(Pr-iso)-Ph, 4-(Pr-iso)-Ph, 3-(Bu-n)-Ph, 4-(Bu-n)-Ph, 3-(Bu-tert)-Ph, 4-(Bu-tert)-Ph, 3-(Bu-iso)-Ph, 3-(Bu-sec)-Ph, 4-F-3-Me-Ph, 3-F-4-Me-Ph, 4-Cl-3-Me-Ph, 3-Cl-4-Me-Ph, 4-Br-3-Me-Ph, 3-Br-4-Me-Ph, 4-F-3,5-Me$_2$-Ph, 4-Cl-3,5-Me$_2$-Ph, 4-Br-3,5-Me$_2$-Ph, 3-MeO-Ph, 4-MeO-Ph, 3-EtO-Ph, 3-(OPr-iso)-Ph, 4-(OPr-iso)-Ph, 3-(OBu-n)-Ph, 4-(OBu-n)-Ph, 3-(OBu-iso)-Ph, 3-(OBu-tert)-Ph, 3,4,5-(MeO)$_3$-Ph, 3,4,5-(EtO)$_3$-Ph, 4-F-3-MeO-Ph, 3-F-4-MeO-Ph, 4-Cl-3-MeO-Ph, 3-Cl-4-MeO-Ph, 3,4-(MeO)$_2$-Ph, 4-Br-3-MeO-Ph, 3-Br-4-MeO-Ph, 4-F-3,5-(MeO)$_2$-Ph, 4-Cl-3,5-(MeO)$_2$-Ph, 4-Br-3,5-(MeO)$_2$-Ph, 3-CF$_3$-Ph, 4-CF$_3$-Ph, 3-F-5-CF$_3$-Ph, 3-Cl-4-CF$_3$-Ph, 3,5-(CF$_3$)$_2$-Ph, 4-F-3,5-(CF$_3$)$_2$-Ph, 4-Cl-3,5-(CF$_3$)$_2$-Ph, 4-Br-3,5-(CF$_3$)$_2$-Ph, 3-CH$_2$F-Ph, 3-CH$_2$Cl-Ph, 3-CH$_2$Br-Ph, 3-CH$_2$I-Ph, 3-CHF$_2$-Ph, 3-CHCl$_2$-Ph, 3-CCl$_3$-Ph, 3-CH$_2$CH$_2$F-Ph, 3-CH$_2$CH$_2$Cl-Ph, 3-CH$_2$CH$_2$Br-Ph, 3-CF$_2$Cl-Ph, 3-CH$_2$CF$_3$-Ph, 3-CF$_2$CF$_3$-Ph, 3-CF$_2$CF$_2$CF$_3$-Ph, 4-CH$_2$F-Ph, 4-CH$_2$Cl-Ph, 4-CH$_2$Br-Ph, 4-CH$_2$I-Ph, 4-CHF$_2$-Ph, 4-CHCl$_2$-Ph, 4-CCl$_3$-Ph, 4-CH$_2$CH$_2$F-Ph, 4-CH$_2$CH$_2$Cl-Ph, 4-CH$_2$CH$_2$Br-Ph, 4-CF$_2$Cl-Ph, 4-CH$_2$CF$_3$-Ph, 4-CF$_2$CF$_2$CF3-Ph, 4-CF$_2$CF$_2$CF$_2$CF$_3$-Ph, 3-OCH$_2$F-Ph, 3-OCHF$_2$-Ph, 3-OCF$_3$-Ph, 3-OCClF$_2$-Ph, 3-OCBrF$_2$-Ph, 3-OCF$_2$CHF$_2$-Ph, 3-OCH$_2$CH$_2$F-Ph, 3-OCH$_2$CH$_2$Cl-Ph, 3-OCH$_2$CH$_2$Br-Ph, 3-OCH$_2$CH$_2$I-Ph, 3-OCH$_2$CF$_3$-Ph, 3-OCH$_2$CCl$_3$-Ph, 3-OCF(CH$_3$)$_2$-Ph, 3-OCH$_2$CH$_2$CH$_2$CH$_2$F-Ph, 4-OCH$_2$F-Ph, 4-OCHF$_2$-Ph, 4-OCF$_3$-Ph, 4-OCClF$_2$-Ph, 4-OCBrF$_2$-Ph, 4-OCF$_2$CHF$_2$-Ph, 4-OCH$_2$CH$_2$F-Ph, 4-OCH$_2$CH$_2$Cl-Ph, 4-OCH$_2$CH$_2$Br-Ph, 4-OCH$_2$CH$_2$I-Ph, 4-OCH$_2$CF$_3$-Ph, 4-OCH$_2$CCl$_3$-Ph, 4-OCF(CH$_3$)$_2$-Ph, 4-OCH$_2$CH$_2$CH$_2$CH$_2$F-Ph, 3-Me$_2$N-Ph, 4-Me$_2$N-Ph, 3,5-(Me$_2$N)$_2$-Ph, 4-F-3,5-(Me$_2$N)$_2$-Ph, 4-Cl-3,5-(Me$_2$N)$_2$-Ph, 4-Br-3,5-(Me$_2$N)$_2$-Ph, 3-Et$_2$N-Ph, 4-(Pr-n)$_2$N-Ph, 3-(Bu-n)$_2$N-Ph, 3-(Pr-iso)$_2$N-Ph, 3-NO$_2$-Ph, 4-NO$_2$-Ph, 3,5-(NO$_2$)$_2$-Ph, 4-F-3,5-(NO$_2$)$_2$-Ph, 4-Cl-3,5-(NO$_2$)$_2$-Ph, 4-Br-3,5-(NO$_2$)$_2$-Ph, 4-Me-3-NO$_2$-Ph, 4-Cl-3-NO$_2$-Ph, 4-MeO-3-NO$_2$-Ph, 3-CN-Ph, 4-CN-Ph, 4-F-3-CN-Ph, 4-Cl-3-CN-Ph, 3,5-(CN)$_2$-Ph, 4-F-3,5-(CN)$_2$-Ph, 4-Cl-3,5-(CN)$_2$-Ph, 4-Br-3,5-(CN)$_2$-Ph, 3-CO$_2$Me-Ph, 4-CO$_2$Me-Ph, 4-F-3-CO$_2$Me-Ph, 4-Cl-3-CO$_2$Me-Ph, 4-F-3,5-(CO$_2$Me)$_2$-Ph, 4-Cl-3,5-(CO$_2$Me)$_2$-Ph, 3-Ph-Ph, 4-Ph-Ph, 3,5-Ph$_2$-Ph, 4-F-3-Ph-Ph, 3-F-4-Ph-Ph, 4-Cl-3-Ph-Ph, 3-Cl-4-Ph-Ph, 4-Br-3-Ph-Ph, 3-Br-4-Ph-Ph, 4-F-3,5-Ph$_2$-Ph, 4-Cl-3,5-Ph$_2$-Ph, 4-Br-3,5-Ph$_2$-Ph, 3-PhO-Ph, 4-PhO-Ph, 3,5-(PhO)$_2$-Ph, 4-Cl-3-PhO-Ph, 4-F-3-PhO-Ph, 3-F-4-PhO-Ph, 4-Cl-3-PhO-Ph, 3-Cl-4-PhO-Ph, 4-Br-3-PhO-Ph, 3-Br-4-PhO-Ph, 4-F-3,5-(PhO)$_2$-Ph, 4-Cl-3,5-(PhO)$_2$-Ph and 4-Br-3,5-(PhO)$_2$-Ph.

Preferable examples of the substituent $R^3$ include Ph and thiophen-2-yl.

[Examples of $R^4$ of the compounds of the present invention]

Examples of the substituent $R^4$ specifically include H, F, Cl, Br, I, Me, Et, Pr-n, Pr-iso, Bu-n, Bu-iso, Bu-sec, Bu-tert, OMe, OEt, OPr-n, OPr-iso, OBu-n, OBu-iso, OBu-sec, OBu-tert, SMe, SEt, SPr-n, SPr-iso, SBu-n, SBu-iso, SBu-sec and SBu-tert.

The compounds of the present invention can be applied as a herbicide for upland field, paddy field and non-arable land through either soil treatment or foliage treatment.

Examples of the weed which can be controlled by using the compounds of the present invention include broad-leaved weeds, such as *Solanum nigrum, Datura stramonium, Abutilon theophrasti, Sida spinosa, Ipomoea purpurea, Amaranthus lividus, Amaranthus retroflexus, Xanthium pensylvanicum, Ambrosia artemisiaefolia, Helianthus annuus, Galinsoga ciliata, Cirsium arvense, Senecio vulgaris, Erigeron annuus, Rorippa indica, Sinapis arvensis, Capsella Bursa-pastoris, Polygonum Blumei, Polygonum convolvulus, Portulaca oleracea, Chenopodium album, Chenopodium ficifolium, Kochias coparia, Stellaria media, Veronica persica, Commelina communis, Lamium amplexicaule, Lamium purpureum, Euphorbia supina, Euphorbia maculata, Galium aparine, Rubia akane, viola arvensis, Sesbania exaltata, Cassia obtusifolia, Bidens pilosa*; Graminaceous weeds such as *Sorghum bicolor, Panicum dichotomiflorum, Sorghum halepense, Echinochloa crus-galli, Digitaria adscendens, Avena fatua, Eleusine indica, Setaria viridis, Alopecurus aequalis*; Cyperaceous weeds such as *Cyperus rotundus*; various paddy weeds such as *Alisma canaliculatum, Sagittaria trifolia, Sagittaria pygmaea, Cyperus difformis, Cyperus serotinus, Scirpus juncoides, Eleocharis kuroguwai, Lindernia pyxidaria, Monochoria vaginalis, Potamogeton distinctus, Rotala indica, Echinochloa crus-galli.*

The compounds of the present invention include compounds which can be harmlessly applied to the important crops such as wheat, corn, barley, soybean, rice, cotton, sugar beet and sorghum.

Further, the compounds of the present invention are also useful as a defoliant.

The compounds of the present invention can be synthesized according to the process (Scheme 1) illustrated in *J. Heterocyclic Chem.*, 19, 1355 (1982) and the process (Scheme 2) described hereinafter. ($R^1$, $R^2$, $R^3$ and $R^4$ have the same meanings as defined above and A represents a hydroxy, methoxy, ethoxy or dimethylamino group in Schemes 1 and 2.)

Scheme 1

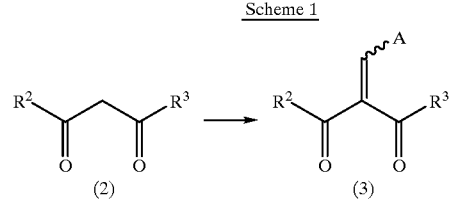

-continued

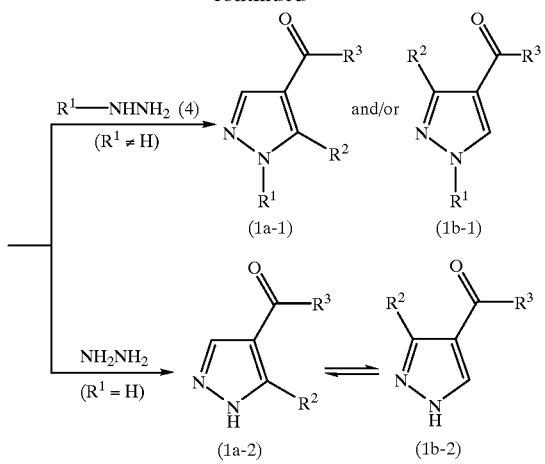

Scheme 1 illustrates the process for preparing the compounds (1a-1) and (1b-1), which are included in the compounds of the present invention, wherein a compound represented by the formula (3) which can be obtained by formylating, methoxymethylenating, ethoxymethylenating or dimethylaminomethylenating the active methylene group of β-diketone represented by the formula (2), is reacted with a hydrazine derivative (4).

A combination of formic ester (such as methyl formate and ethyl formate) or oxalic ester (such as methyl oxalate and ethyl oxalate) with a base can be used as a formylating agent. A combination of methyl or ethyl orthoformate with acetic anhydride, optionally added with a Lewis acid such as anhydrous zinc chloride, and the like can be used as a methoxymethylenating or ethoxymethylenating agent respectively. N,N-dimethylformamide dimethylacetal or tert-butoxy bis-dimethylaminomethane and the like can be used as a dimethylaminating agent.

The compounds (1a-1) and (1b-1) included in the compounds of the present invention can be prepared by the reaction of a compound represented by the formula (3) with a hydrazine derivative (4), and the hydrazine derivative (4) to be used can also be used in the form of a salt with mineral acid or a hydrate. In addition, when the hydrazine derivative is used in the form of a salt of mineral oil, it can also be used with a form neutralized by a base in the reaction system. When hydrazine hydrate or a salt of hydrazine with mineral acid is used ($R^1$=H), the resulting compounds (1a-2) and (1b-2) included in the compounds of the present invention are tautomers, which can be reacted with $R^1$-Z (wherein Z represents a halogen atom, and $R^1$ represents the same meaning as defined above, with the proviso that $R^1$ is not a hydrogen atom) in the presence or absence of a base to prepare the compounds (1a-1) and (1b-1) included in the compounds of the present invention. Provided that, when $R^1$ is a $C_{1-4}$ alkylcarbamoyl group, isocyanates ($R^1$NCO) are reacted.

Examples of the base to be used in the said reaction include alkali metal alkoxides such as sodium ethoxide, sodium methoxide and potassium t-butoxide, alkali metal hydroxides such as sodium hydroxide and potassium hydroxide, alkali metal carbonates such as sodium carbonate and potassium carbonate, an organic bases such as triethylamine, pyridine and 4-dimethylaminopyridine, and sodium hydride.

The reaction represented by the Scheme 1 can be carried out using no solvent or in a solvent which is inactive to the reaction. Such inactive solvents include lower alcohols such as methanol and ethanol, aromatic hydrocarbons such as benzene and toluene, ethers such as diethyl ether, tetrahydrofuran, 1,4-dioxane, 1,2-dimethoxyethane and 1,2-diethoxyethane, halogenated hydrocarbons such as methylene chloride, chloroform and 1,2-dichloroethane, amides such as dimethylformamide and dimethylacetamide, acetonitrile, dimethylsulfoxide, and the mixture solvent thereof. Mixture solvents of the said solvents with water can optionally be used. In some cases, good results may be obtained by adding to the reaction with a quaternary ammonium salt such as tetra-n-butylammonium bromide as a catalyst.

The reaction temperature may be set to any temperature between −30° C. and 200° C., preferably between 0° C. and 150° C. When a solvent is used, the reaction temperature is preferably in the range between 0° C. and a boiling point of the solvent.

The base is used in an amount of 0.8 to 10 equivalents, preferably 0.8 to 3 equivalents based on the reaction substrate.

The reaction period to be needed is 0.5 to 72 hours, preferably 1 to 24 hours.

Scheme 2

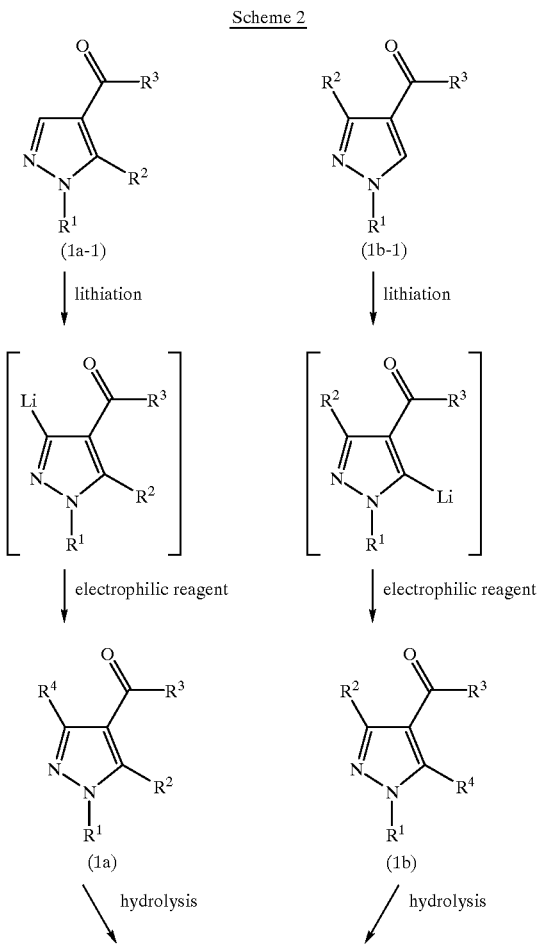

-continued

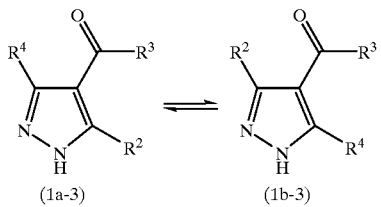

Scheme 2 illustrates the process for preparing the compound (1a-3) or (1b-3) included in the compounds of the present invention, wherein the compound (1a-1) or (1b-1) included in the compounds of the present invention, which is prepared according to Scheme 1, is lithiated on 3 or 5 position of the pyrazole ring with a lithiating agent such as lithium diisopropylamide and then reacted with a suitable electrophilic reagent to prepare the compound (1a) or (1b) of the present invention, followed by cleaving the substituent on 1-position of the pyrazole ring by hydrolysis under an acidic or basic condition to synthesize the compound (1a-3) or (1b-3). The compounds (1a-3) and (1b-3) are tautomers.

Examples of the electrophilic reagent to be used include electrophilic halogenating agents such as halogenated alkyls ($C_{1-4}$ alkyl-Z, wherein Z represents a halogen atom), disulfides ($C_{1-4}$ alkyl-S-S-$C_{1-4}$ alkyl) and N-chloro- or N-bromo-succinimide.

A compound of the present invention prepared according to Scheme 1 or 2 can be obtained from a reaction mixture using a conventional method, and, if necessary, can be separated and purified using any purification method such as recrystallization and column chromatography.

When a compound according to the present invention comprises an asymmetric carbon atom, both the optically active isomers, i.e. (+)-isomer and (−)-isomer, are included within the scope of the present invention.

The following Examples specifically illustrate the process for preparing the compound of the present invention. However, it should be recognized that the scope of the present invention is not limited to these Examples. In this connection, although one of the tautomers is described in the following when a compound according to the present invention can exist in the form of tautomer, all of the tautomers are included within the scope of the present invention.

EXAMPLE 1

Synthesis of 4-(2-chlorobenzoyl)-3-phenylpyrazole (Compound No. 1)

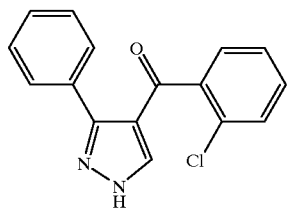

Sodium hydride (3.15 g) which had been washed with n-hexane was suspended in tetrahydrofuran (100 ml), and to this methyl benzoate (8.58 g) and 18-crown-6-ether (0.07 g) were added at room temperature and then a solution of o-chloroacetophenone (5.03 g) and three drops of methanol was added dropwise. After stirring for 10 minutes at room temperature, the temperature of the reaction mixture was allowed to increase gradually, and then the mixture was refluxed for 2 hours. After allowing the reaction mixture to cool, it was poured into ice-water, acidified by adding diluted hydrochloric acid, extracted with ethyl acetate, washed with aqueous saturated sodium chloride and dried on anhydrous sodium sulfate, and then the solvent was distilled off. The resulting residue was added with n-hexane (50 ml), diethyl ether (50 ml) and a solution of sodium hydroxide and vigorously stirred for 30 minutes. The organic layer was removed and the aqueous layer was washed with a n-hexane/diethyl ether mixture solvent. This was acidified by adding diluted hydrochloric acid, extracted with benzene, dried on anhydrous sodium sulfate, and then the solvent was distilled off. The resulting residue was dissolved in benzene and filtrated through silica gel, and then the solvent was distilled off to give the compound of interest, 1-(2-chlorophenyl)-3-phenyl-1,3-propanedione (6.14 g) as a reddish brown solid.

NMR (CDCl$_3$, δppm) 6.75(s, 1H), 7.53(m, 6H), 7.95(m, 2H), 16.5(m, 1H).

1-(2-Chlorophenyl)-3-phenyl-1,3-propanedione (3.84 g) was dissolved in N,N-dimethlyformamide dimethylacetal (6 ml) and heated to reflux for 3 hours. After allowing the reaction mixture to cool, the solvent was distilled off and the residue was then purified by column chromatography on silica gel (eluent: benzene/ethyl acetate=3/1) to give the compound of interest, 1-(2-chlorophenyl)-3-(N,N-dimethylaminomethylene)-3-phenyl-1,3-propanedione (2.98 g) as a yellow crystal. M.P.: 125–126.5° C.

1-(2-Chlorophenyl)-3-(N,N-dimethylaminomethylene)-3-phenyl-1,3-propanedione (2.63 g) and hydrazine hydrate (0.85 g) were dissolved in ethanol (40 ml) and stirred for 2 days at room temperature. After ethanol was distilled off, the residue was added with diethyl ether, washed with aqueous saturated sodium chloride and dried on anhydrous sodium sulfate, and then the solvent was distilled off. The resulting residue was washed with acetonitrile to give the compound of interest (0.96 g) as a colorless crystal. M.P.: 182–186° C.

EXAMPLE 2

Synthesis of 3-(3-chlorophenyl)-4-benzoylpyrazole (Compound No. 2)

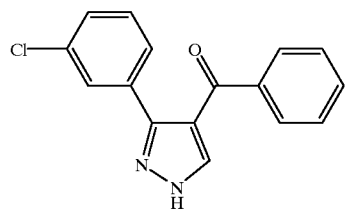

1-(3-Chlorophenyl)-2-(N,N-dimethylaminomethylene)-3-phenyl-1,3-propanedione (11.25 g) synthesized in accordance with Example 1 was dissolved in ethanol (150 ml) and added with hydrazine hydrate (1.98 g). After heating at reflux temperature for 3 hours, the solvent was distilled off, and then the resulting residue was added with diisopropyl ether and stirred. The resulting solid was then filtered off, recrystallized from acetonitrile to give the compound of interest (3.0 g). M.P.: 161.3–164.1° C.

EXAMPLE 3

Synthesis of 3-(3,4-dichlorophenyl)-4-(thiophen-2-ylcarbonyl)-pyrazole (Compound No. 3) and 4-(3,4-dichlorobenzoyl)-3-(thiophen-2-yl)pyrazole (Compound No. 4)

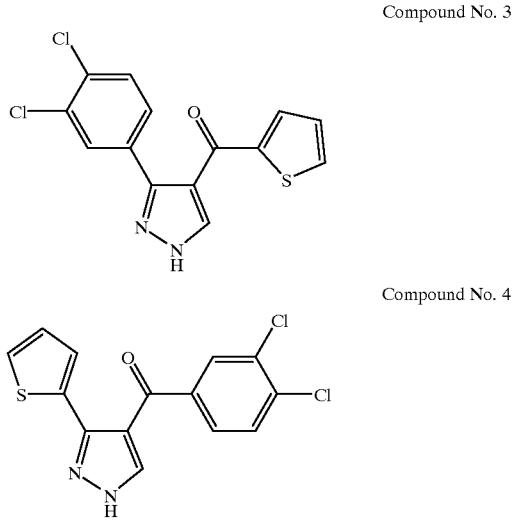

Compound No. 3

Compound No. 4

1-(3,4-Dichlorophenyl)-2-(N,N-dimethylaminomethylene)-3-(thiophen-2-yl)-1,3-propanedione (0.93 g) synthesized in accordance with Example 1 was dissolved in ethanol (20 ml) and added with hydrazine hydrate (0.23 g). After heating at reflux temperature for 3 hours, the solvent was distilled off, and then the resulting residue was added with diisopropyl ether and stirred. The resulting solid was then filtered off to give the compound of interest (Compound No. 3; 0.4 g). M.P.: 165.5–169.9° C.

The thus obtained filtrate was subjected to HPLC (ODS column; $CH_3CN/H_2O=3/1$) to isolate the other compound of interest (Compound No. 4; 50 mg).

EXAMPLE 4

Synthesis of 4-benzoyl-3-(3-chlorophenyl)-1-methoxymethylpyrazole (Compound No. 5)

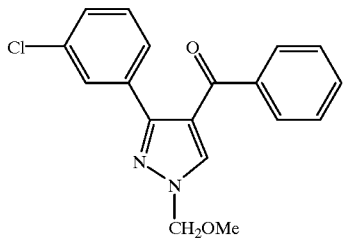

To 55% sodium hydride (1.9 g) was added N,N-dimethylformamide (3 ml) and stirred while cooled with ice. To this was then added dropwise a solution of 4-benzoyl-3-(3-chlorophenyl)pyrazole (1.24 g) in N,N-dimethylformamide. The reaction mixture was stirred for 20 minutes at room temperature after the vigorous foaming ceased. The reaction mixture was added with chloromethyl methyl ether (0.59 g) and stirred for 5 hours at room temperature, which was then poured into ice-water, extracted with ethyl acetate, washed with water and dried on anhydrous sodium sulfate, and the solvent was then distilled off under reduced pressure. The thus obtained residue was purified by column chromatography (silica gel; ethyl acetate/n-hexane=3/1) and recrystallized from acetonitrile to give the compound of interest (620 mg). M.P.: 105.5–107.9° C.

EXAMPLE 5

Synthesis of 4-benzoyl-3-(3-chlorophenyl)-1-(2-methoxyethoxymethyl)pyrazole (Compound No. 6) and 4-benzoyl-5-(3-chlorophenyl)-1-(2-methoxyethoxymethyl)pyrazole (Compound No. 7)

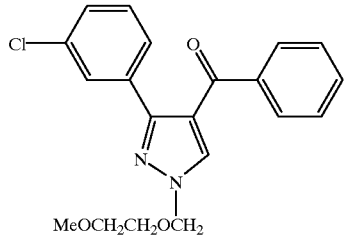

Compound No. 6

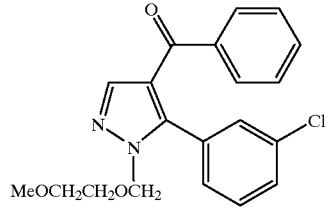

Compound No. 7

4-Benzoyl-3-(3-chlorophenyl)pyrazole (0.5 g) was dissolved in N,N-dimethylformamide (20 ml), which was added with potassium carbonate anhydride (0.37 g) and 2-methoxyethoxymethyl chloride (0.24 g) and stirred for 6 hours at 80° C. After allowing the reaction mixture to cool, it was added with water, extracted with ethyl acetate, washed with water and dried on anhydrous sodium sulfate, and the solvent was then distilled off under reduced pressure. The thus obtained residue was purified by thin-layer chromatography (silica gel; ethyl acetate/n-hexane=1/3) and subjected to liquid chromatography (ODS column; acetonitrile/water=2/1) to isolate Compound No. 6 (resinous material; 30 mg) and Compound No. 7 (M.P.: 77.0–80.3° C.; 200 mg).

NMR spectrum for Compound No. 7 ($CDCl_3$, δppm) 3.38(3H, s), 3.36–3.57(2H, m), 3.82–3.84(2H, m), 5.43(2H, s), 7.26–7.75(9H, m), 7.91(1H, s).

EXAMPLE 6

Synthesis of 1-acetyl-4-benzoyl-3-(4-bromophenyl) pyrazole (Compound No. 75) and 1-acetyl-4-benzoyl-5-(4-bromophenyl)pyrazole (Compound No. 76)

Compound No. 75

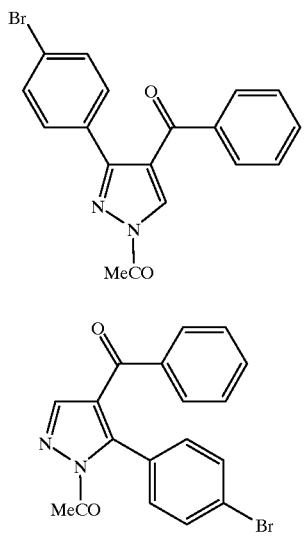

Compound No. 76

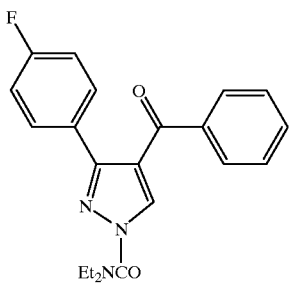

4-Benzoyl-3-(4-bromophenyl)pyrazole (0.1 g) synthesized in accordance with Example 2 was dissolved in tetrahydrofuran (5 ml) and added with triethylamine (0.06 g) and acetyl chloride (0.04 g) followed by stirring for 0.5 hour at room temperature. The reaction mixture was added with water, extracted with ethyl acetate, washed with aqueous saturated sodium chloride and dried on anhydrous sodium sulfate, and then the solvent was distilled off under reduced pressure. The resulting residue was purified by chromatography (silica gel; chloroform) to give the compound of interest (resinous material; 0.07 g).

NMR spectrum for Compound No. 75 or Compound No. 76 (CDCl$_3$, δ ppm) 2.79(3H, s), 7.24–8.01(9H, m), 8.53(1H, s).

EXAMPLE 7

Synthesis of 1-diethylcarbamoyl-3-(4-fluorophenyl)-4-benzoylpyrazole (Compound No. 77) and 1-diethylcarbamoyl-5-(4-fluorophenyl)-4-benzoylpyrazole (Compound No. 78)

Compound No. 77

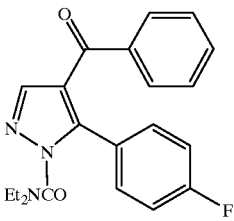

Compound No. 78

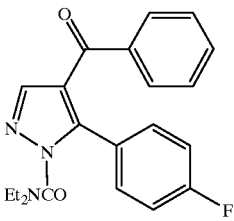

4-Benzoyl-3-(4-fluorophenyl)pyrazole (0.54 g) synthesized in accordance with Example 2 was dissolved in tetrahydrofuran (3 ml) and added with 4-dimethylaminopyridine (0.28 g) and diethylcarbamoyl chloride (0.27 g) followed by stirring for 5 hours at room temperature. The reaction mixture was added with water, extracted with ethyl acetate, washed with aqueous saturated sodium chloride and dried on anhydrous sodium sulfate, and then the solvent was distilled off under reduced pressure. The resulting residue was purified by chromatography (silica gel; chloroform) to give the mixture of the compounds of interest (Compound No. 77/Compound No. 78=1/1; 0.47 g).

EXAMPLE 8

Synthesis of 4-benzoyl-3-(3-chloro-4-methoxyphenyl)-1-methylsulfonylpyrazole (Compound No. 79) and 4-benzoyl-5-(3-chloro-4-methoxyphenyl)-1-methylsulfonylpyrazole (Compound No. 80)

Compound No. 79

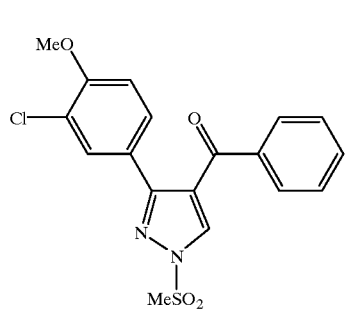

Compound No. 80

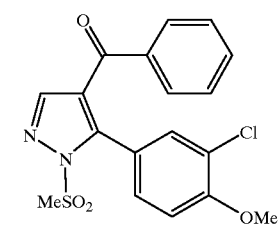

4-Benzoyl-3-(3-chloro-4-methoxyphenyl)pyrazole (0.38 g) synthesized in accordance with Example 2 was dissolved in tetrahydrofuran (10 ml) and added with triethylamine (0.14 g) and methanesulfonyl chloride (0.18 g) followed by stirring for 3 hours at room temperature. The reaction mixture was added with water, extracted with ethyl acetate, washed with aqueous saturated sodium chloride and dried on anhydrous sodium sulfate, and then the solvent was distilled off under reduced pressure. The resulting residue was purified by chromatography (silica gel; chloroform/ethyl acetate=2/1) to give the mixture of the compounds of interest (Compound No. 79/Compound No. 80=1/1; 0.50 g).

EXAMPLE 9

Synthesis of 4-benzoyl-3-(3-chloro-4-methoxyphenyl)-1-dimethylsulfamoylpyrazole (Compound 81) and 4-benzoyl-5-(3-chloro-4-methoxyphenyl)-1-dimethylsulfamoylpyrazole (Compound 82)

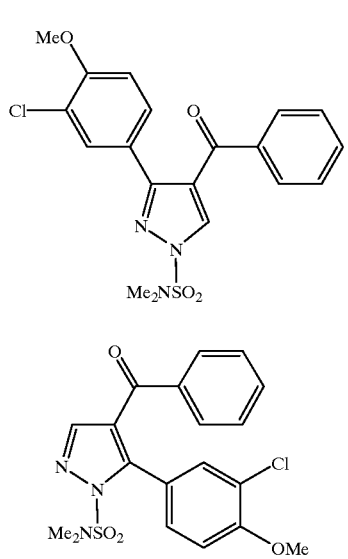

Compound No. 81

Compound No. 82

4-Benzoyl-3-(3-chloro-4-methoxyphenyl)pyrazole (0.37 g) was dissolved in tetrahydrofuran (10 ml) and added with potassium carbonate (0.20 g) and dimethylsulfamoyl chloride (0.20 g) followed by stirring for 1 hour at 80° C. The reaction mixture was added with water, extracted with ethyl acetate, washed with aqueous saturated sodium chloride and dried on anhydrous sodium sulfate, and then the solvent was distilled off under reduced pressure. The resulting residue was purified by chromatography (silica gel; chloroform/ethyl acetate=2/1) to give the mixture of the compounds of interest (Compound No. 81/Compound No. 82=1/1; 0.50 g).

The structures and melting points of the compounds of the present invention synthesized in accordance with the aforementioned Schemes or Examples are listed in Table 1. In Table 1, Ph represents a phenyl group.

TABLE 1

| Compound No. | $R^2$ | $R^3$ | M.P. (° C.) |
| --- | --- | --- | --- |
| 8 | Ph | Ph | 140–141 |
| 9 | 4-F-Ph | 4-F-pH | 180–182 |
| 10 | 4-Cl-Ph | 4-Cl-Ph | 182–183 |
| 11 | 3-Cl-Ph | 3-Cl-Ph | 103–105 |
| 12 | 4-Cl-Ph | Ph | 170–172 |
| 13 | 3-$CF_3$-Ph | Ph | 150.2–157.9 |
| 14 | 4-$CF_3$-Ph | Ph | 182.3–188.3 |
| 15 | 3-CN-Ph | Ph | 183.5–185.2 |
| 16*[1] | 3-$CHF_2$O-Ph | Ph | 91.8–95.0 |
| 17*[1] | Ph | 3-$CHF_2$O-Ph | 91.8–95.0 |

TABLE 1-continued

| Compound No. | $R^2$ | $R^3$ | M.P. (° C.) |
| --- | --- | --- | --- |
| 18*[2] | Ph | 3-$CH_3$O-Ph | 91.6–107.9 |
| 19*[2] | 3-$CH_3$O-Ph | Ph | 91.6–107.9 |
| 20*[3] | 3-$CH_3$-Ph | Ph | 134.9–138.7 |
| 21*[3] | Ph | 3-$CH_3$-Ph | 134.9–138.7 |
| 22 | 3-I-Ph | Ph | 152–155 |
| 23 | 4-I-Ph | Ph | 195–199 |
| 24 | 3-Br-Ph | Ph | 164–167.5 |
| 25 | Ph | thiophen-2-yl | 125–140 |
| 26 | 3-F-Ph | Ph | 132.5–134.6 |
| 27 | 4-F-Ph | Ph | 147–149.3 |
| 28 | 3,4-$Cl_2$-Ph | Ph | 191.8–192.5 |
| 29 | Ph | 2,5-$Cl_2$-Ph | 143–143.7 |
| 30 | Ph | 2,4-$Cl_2$-Ph | 139–139.5 |
| 31 | 3-$NO_2$-Ph | Ph | 181–182.5 |
| 32 | 3-Cl-Ph | thiophen-2-yl | 119–120 |
| 33 | thiophen-2-yl | 3-Cl-Ph | resinous |
| 34 | 3,5-$Cl_2$-Ph | Ph | 167–168 |
| 35 | 3-Cl-4-F-Ph | Ph | 168–182 |
| 36*[4] | 3-$Me_3$N-Ph | Ph | — |
| 37*[4] | Ph | 3-$Me_2$N-Ph | — |
| 38 | 4-Cl-Ph | thiophen-2-yl | 186–188 |
| 39 | thiophen-2-yl | 4-Cl-Ph | 152–153 |
| 40 | thiophen-2-yl | 2-Cl-Ph | 160–162 |
| 41 | thiophen-2-yl | thiophen-2-yl | 133–134 |
| 42 | 2-naphthyl | thiophen-2-yl | 178–179 |
| 43 | 2-naphthyl | Ph | 160–161 |
| 44 | 3,4-$Cl_2$-Ph | furan-2-yl | 212–213 |
| 45 | 2-naphthyl | furan-2-yl | 156–157 |
| 46 | furan-2-yl | 2-naphthyl | 180–181 |
| 47 | thiophen-2-yl | 1-naphthyl | resinous |
| 48 | 3,4,5-$Cl_3$-Ph | Ph | 200–201 |
| 49 | pyridin-3-yl | thiophen-2-yl | 140–141 |
| 50 | thiophen-2-yl | pyridin-3-yl | 182–184 |
| 51 | Ph | 1-Me-3,5-$Cl_2$-pyrazol-4-yl | 108–109 |
| 52 | thiophen-2-yl | 5-Cl-thiophen-2-yl | resinous |
| 53 | 5-Cl-thiophen-2-yl | 5-Cl-thiophen-2-yl | resinous |
| 54 | 4-Br-3,5-$Cl_2$-Ph | Ph | 218–220 |
| 55 | 4-Br-Ph | Ph | 183–189 |
| 56 | 3,4-$Cl_2$-Ph | 2-Cl-Ph | 140–150 |
| 57 | 3,5-$Cl_2$-4-I-Ph | Ph | 192–217 |
| 58 | 3,5-$(CF_3)_2$-Ph | Ph | 173–174 |
| 59 | 3,5-$F_2$-Ph | Ph | 155–157 |
| 60 | Ph | 3,5-$F_2$-Ph | 140–142 |
| 61 | 3,5-$Cl_2$-4-F-Ph | Ph | 168–174 |
| 62 | 3,4-$Me_2$-Ph | Ph | 148–150 |
| 63*[5] | 3-PhO-Ph | Ph | resinous |
| 64*[5] | Ph | 3-PhO-Ph | resinous |
| 65 | 3,5-$Br_2$-4-Cl-Ph | Ph | 210–214 |
| 66 | 3,4,5-$F_3$-Ph | Ph | 180–181 |
| 67*[6] | 3,4-$F_2$-Ph | Ph | 136–139 |
| 68*[6] | Ph | 3,4-$F_2$-Ph | 136–139 |
| 69 | 3,5-$Br_2$-Ph | Ph | 161–162 |
| 70 | 3-Br-5-I-Ph | Ph | 172–178 |
| 71 | 3,4,5-$Br_3$-Ph | Ph | 222–225 |
| 72 | 3-Cl-4-MeO-Ph | Ph | 200–202 |
| 73 | Ph | 2,6-$Cl_2$-pyridin-4-yl | resinous |
| 74 | 3,5-$Me_2$-Ph | Ph | 165–170 |

*[1]Mixture of No. 16/No. 17 = 3/1 determined by $^1$H-NMR.
*[2]Mixture of No. 18/No. 19 = 1/1 determined by $^1$H-NMR.
*[3]Mixture of No. 20/No. 21 = 5/1 determined by $^1$H-NMR.
*[4]Mixture of No. 36/No. 37 = 1/1 determined by $^1$H-NMR.
*[5]Mixture of No. 63/No. 64 = 6/4 determined by $^1$H-NMR.
*[6]Mixture of No. 67/No. 68 = 7/3 determined by $^1$H-NMR.

Examples of the compounds of the present invention including the aforementioned compounds which are synthesized in accordance with the aforementioned Schemes or Examples are listed in the following tables. In this connection, the abbreviations described in the tables have the meanings as defined above.

TABLE 2

[Structures shown: four pyrazole-based compounds with Bq, Ak substituents and $R^1$ on nitrogen]

| $R^1$ | $A_k$ | $B_q$ |
|---|---|---|
| H | H | H |
| H | 2-F | H |
| H | 3-F | H |
| H | 4-F | H |
| H | 2-Cl | H |
| H | 3-Cl | H |
| H | 4-Cl | H |
| H | 2-Br | H |
| H | 3-Br | H |
| H | 4-Br | H |
| H | 2-I | H |
| H | 3-I | H |
| H | 4-I | H |
| H | 2-Me | H |
| H | 3-Me | H |
| H | 4-Me | H |
| H | 2-Et | H |
| H | 3-Et | H |
| H | 4-Et | H |
| H | 2-(Pr-n) | H |
| H | 3-(Pr-n) | H |
| H | 4-(Pr-n) | H |
| H | 3-(Pr-iso) | H |
| H | 4-(Pr-iso) | H |
| H | 4-(Bu-tert) | H |
| H | 3-(Bu-tert) | H |
| H | 4-(Bu-n) | H |
| H | 3-(Bu-iso) | H |
| H | 3-(Bu-sec) | H |
| H | 3-OMe | H |
| H | 4-OMe | H |
| H | 3-OEt | H |
| H | 3-O(Pr-iso) | H |
| H | 4-O(Pr-iso) | H |
| H | 3-O(Bu-n) | H |
| H | 4-O(Bu-n) | H |

TABLE 2-continued

| $R^1$ | $A_k$ | $B_q$ |
|---|---|---|
| H | 3-O(Bu-iso) | H |
| H | 3-O(Bu-tert) | H |
| H | 2-CN | H |
| H | 3-CN | H |
| H | 4-CN | H |
| H | 3-OPh | H |
| H | 4-OPh | H |
| H | 3-$NO_2$ | H |
| H | 4-$NO_2$ | H |
| H | 3-$CF_3$ | H |
| H | 4-$CF_3$ | H |
| H | 3-$CH_2F$ | H |
| H | 3-$CH_2Cl$ | H |
| H | 3-$CH_2Br$ | H |
| H | 3-$CH_2I$ | H |
| H | 3-$CHF_2$ | H |
| H | 3-$CHCl_2$ | H |
| H | 3-$CCl_3$ | H |
| H | 3-$CH_2CH_2F$ | H |
| H | 3-$CH_2CH_2Cl$ | H |
| H | 3-$CH_2CH_2Br$ | H |
| H | 3-$CF_2Cl$ | H |
| H | 3-$CH_2CF_3$ | H |
| H | 3-$CF_2CF_2CF_3$ | H |
| H | 3-$CF_2CF_2CF_2CF_3$ | H |
| H | 4-$CH_2F$ | H |
| H | 4-$CH_2Cl$ | H |
| H | 4-$CH_2Br$ | H |
| H | 4-$CH_2I$ | H |
| H | 4-$CHF_2$ | H |
| H | 4-$CHCl_2$ | H |
| H | 4-$CCl_3$ | H |
| H | 4-$CH_2CH_2F$ | H |
| H | 4-$CH_2CH_2Cl$ | H |
| H | 4-$CH_2CH_2Br$ | H |
| H | 4-$CF_2Cl$ | H |
| H | 4-$CH_2CF_3$ | H |
| H | 4-$CF_2CF_2CF_3$ | H |
| H | 4-$CF_2CF_2CF_2CF_3$ | H |
| H | 3-$OCHF_2$ | H |
| H | 3-$OCF_3$ | H |
| H | 3-$OCClF_2$ | H |
| H | 3-$OCBrF_2$ | H |
| H | 3-$OCF_2CHF_2$ | H |
| H | 3-$OCH_2CH_2F$ | H |
| H | 3-$OCH_2CH_2Cl$ | H |
| H | 3-$OCH_2CH_2Br$ | H |
| H | 3-$OCH_2CH_2I$ | H |
| H | 3-$OCH_2CF_3$ | H |
| H | 3-$OCH_2CCl_3$ | H |
| H | 3-$OCF(CH_3)_2$ | H |
| H | 3-$OCH_2CH_2CH_2CH_2F$ | H |
| H | 4-$OCHF_2$ | H |
| H | 4-$OCF_3$ | H |
| H | 4-$OCClF_2$ | H |
| H | 4-$OCBrF_2$ | H |
| H | 4-$OCF_2CHF_2$ | H |
| H | 4-$OCH_2CH_2F$ | H |
| H | 4-$OCH_2CH_2Cl$ | H |
| H | 4-$OCH_2CH_2Br$ | H |
| H | 4-$OCH_2CH_2I$ | H |
| H | 4-$OCH_2CF_3$ | H |
| H | 4-$OCH_2CCl_3$ | H |
| H | 4-$OCF(CH_3)_2$ | H |
| H | 4-$OCH_2CH_2CH_2CH_2F$ | H |
| H | 3-$NMe_2$ | H |
| H | 3-$NEt_2$ | H |
| H | 4-$N(nPr)_2$ | H |
| H | 3-$N(nBu)_2$ | H |
| H | 3-$N(iPr)_2$ | H |
| H | 2,4-$Cl_2$ | H |
| H | 2,3-$Cl_2$ | H |
| H | 2,5-$Cl_2$ | H |
| H | 2,6-$Cl_2$ | H |
| H | 3,4-$Cl_2$ | H |
| H | 3,5-$Cl_2$ | H |
| H | 2,4-$F_2$ | H |
| H | 2,3-$F_2$ | H |
| H | 2,5-$F_2$ | H |

TABLE 2-continued

| | | |
|---|---|---|
| H | 2,6-F$_2$ | H |
| H | 3,4-F$_2$ | H |
| H | 3,5-F$_2$ | H |
| H | 2,4-Br$_2$ | H |
| H | 2,3-Br$_2$ | H |
| H | 2,5-Br$_2$ | H |
| H | 2,6-Br$_2$ | H |
| H | 3,4-Br$_2$ | H |
| H | 3,5-Br$_2$ | H |
| H | 2,4-Me$_2$ | H |
| H | 2,3-Me$_2$ | H |
| H | 2,5-Me$_2$ | H |
| H | 2,6-Me$_2$ | H |
| H | 3,4-Me$_2$ | H |
| H | 3,5-Me$_2$ | H |
| H | 2-F-4-Cl | H |
| H | 3-F-4-Cl | H |
| H | 3-Cl-4-F | H |
| H | 2-Cl-4-F | H |
| H | 2-Cl-6-F | H |
| H | 2-F-4-Br | H |
| H | 2-Br-4-F | H |
| H | 3-Br-4-F | H |
| H | 2-F-5-Br | H |
| H | 4-Me-3-NO$_2$ | H |
| H | 2-OMe-4-Cl | H |
| H | 2-OMe-5-Cl | H |
| H | 3,4-(OMe)$_2$ | H |
| H | 2-Cl-3-NO$_2$ | H |
| H | 2-Cl-4-NO$_2$ | H |
| H | 4-Cl-2-NO$_2$ | H |
| H | 5-Cl-2-NO$_2$ | H |
| H | 4-Cl-3-NO$_2$ | H |
| H | 4-Cl-3-OPh | H |
| H | 4-OMe-3-NO$_2$ | H |
| H | 2,3,5-Cl$_3$ | H |
| H | 2,4,6-Cl$_3$ | H |
| H | 3,4,5-Cl$_3$ | H |
| H | 2,3,4-F$_3$ | H |
| H | 2,3,6-F$_3$ | H |
| H | 2,4,5-F$_3$ | H |
| H | 3,4,5-F$_3$ | H |
| H | 3,4,5-(OMe)$_3$ | H |
| H | 3,4,5-(OEt)$_3$ | H |
| H | 2,4-Cl$_2$-5-F | H |
| H | 2,4-Cl$_2$-3,5-NO$_2$ | H |
| H | 2,3,4,5,6-F$_5$ | H |
| H | 2-Cl-3,5-(NO$_2$)$_2$ | H |
| H | 4-Cl-3,5-(NO$_2$)$_2$ | H |
| CH$_2$OMe | H | H |
| CH$_2$OMe | 2-F | H |
| CH$_2$OMe | 3-F | H |
| CH$_2$OMe | 4-F | H |
| CH$_2$OMe | 2-Cl | H |
| CH$_2$OMe | 3-Cl | H |
| CH$_2$OMe | 4-Cl | H |
| CH$_2$OMe | 2-Br | H |
| CH$_2$OMe | 3-Br | H |
| CH$_2$OMe | 4-Br | H |
| CH$_2$OMe | 2-I | H |
| CH$_2$OMe | 3-I | H |
| CH$_2$OMe | 4-I | H |
| CH$_2$OMe | 2-Me | H |
| CH$_2$OMe | 3-Me | H |
| CH$_2$OMe | 3-OCF$_3$ | H |
| CH$_2$OMe | 3-OCClF$_2$ | H |
| CH$_2$OMe | 3-OCBrF$_2$ | H |
| CH$_2$OMe | 4-CF$_3$ | H |
| CH$_2$OMe | 3,4-Cl$_2$ | H |
| CH$_2$OMe | 3-Cl-4-F | H |
| CH$_2$OMe | 3-CF$_3$ | H |
| CH$_2$OEt | 2-Cl | H |
| CH$_2$OEt | 3-Cl | H |
| CH$_2$OEt | 4-Cl | H |
| CH$_2$OEt | 2-Br | H |
| CH$_2$OEt | 3-Br | H |
| CH$_2$OEt | 4-Br | H |
| CH$_2$OEt | 2-I | H |
| CH$_2$OEt | 3-I | H |
| CH$_2$OEt | 4-I | H |
| CH$_2$O(Pr-n) | 3-Cl | H |
| CH$_2$O(Pr-n) | 4-Cl | H |
| CH$_2$O(Pr-n) | 3-Br | H |
| CH$_2$O(Pr-n) | 4-Br | H |
| CH$_2$O(Pr-n) | 3-I | H |
| CH$_2$O(Pr-n) | 4-I | H |
| CH$_2$O(Pr-n) | 3,4-Cl$_2$ | H |
| CH$_2$O(Pr-iso) | 4-Cl | H |
| CH$_2$O(Pr-iso) | 3-Cl | H |
| CH$_2$O(Pr-iso) | 3-Br | H |
| CH$_2$O(Pr-iso) | 3-I | H |
| CH$_2$O(Pr-iso) | 3,4-Cl$_2$ | H |
| CH$_2$O(Pr-iso) | 3-CF$_3$ | H |
| CH$_2$O(Pr-iso) | 3-Cl-4-CF$_3$ | H |
| CH$_2$OC$_2$H$_4$OMe | 3-Cl | H |
| CH$_2$OC$_2$H$_4$OMe | 3-Br | H |
| CH$_2$OC$_2$H$_4$OMe | 3-I | H |
| CH$_2$OC$_2$H$_4$OMe | 3,4-Cl$_2$ | H |
| CH$_2$OC$_2$H$_4$OMe | 3-CF$_3$ | H |
| CH$_2$OC$_2$H$_4$OMe | 3-Cl-4-CF$_3$ | H |
| CH$_2$OC$_2$H$_4$OEt | 3-Cl | H |
| CH$_2$OC$_2$H$_4$OEt | 3-Br | H |
| CH$_2$OC$_2$H$_4$OEt | 3-I | H |
| CH$_2$OC$_2$H$_4$OEt | 3,4-Cl$_2$ | H |
| CH$_2$OC$_2$H$_4$OEt | 3-CF$_3$ | H |
| CH$_2$OC$_2$H$_4$OEt | 3-Cl-4-CF$_3$ | H |
| H | 2-F | 2-F |
| H | 3-F | 3-F |
| H | 4-F | 4-F |
| H | 2-Cl | 2-Cl |
| H | 2-Cl | 3-Cl |
| H | 2-Cl | 4-Cl |
| H | 3-Cl | 2-Cl |
| H | 3-Cl | 3-Cl |
| H | 3-Cl | 4-Cl |
| H | 3-Cl | 2-F |
| H | 3-Cl | 3-F |
| H | 3-Cl | 4-F |
| H | 3-Cl | 3-Br |
| H | 3-Cl | 4-Br |
| H | 3-Cl | 3-Me |
| H | 3-Cl | 3-CF$_3$ |
| H | 3-Cl | 3-OCF$_3$ |
| H | 3-Cl | 3-NO$_2$ |
| H | 3-Cl | 4-OPh |
| H | 3-Cl | 3,4-Cl$_2$ |
| H | 4-Cl | 3-NMe$_2$ |
| H | 3-Br | 3-OMe |
| H | 3-CF$_3$ | 3-Cl |
| H | 4-CF$_3$ | 3-CN |
| H | 3-CN | 3-Me |
| H | 3-CN | 4-OMe |
| H | 3,4-Cl$_2$ | 3-F |
| H | 3,4-Cl$_2$ | 3-Cl |
| H | 3,4-Cl$_2$ | 4-Me |
| H | 3,4-Cl$_2$ | 3,4-Cl$_2$ |
| H | 3-Cl-4-CF$_3$ | 4-NMe$_2$ |
| H | 4-Cl-3-CF$_3$ | 2-F |
| H | 3,5-Cl$_2$ | 3-OPh |
| H | 3,4,5-Cl$_3$ | 3-OMe |
| CH$_2$OMe | 3-Cl | 3,4-Cl$_2$ |
| CH$_2$OMe | 2,3,4,5,6-F$_5$ | 4-OCHF$_2$ |
| CH$_2$OC$_2$H$_4$OMe | 3,5-Cl$_2$ | 4-Et |
| H | 2,4,6-F$_3$ | H |
| H | 2,3,5-F$_3$ | H |
| H | 2,3,4,5-F$_4$ | H |
| H | 2,3,4,6-F$_4$ | H |
| H | 2,3,5,6-F$_4$ | H |
| H | 2,3,4-Cl$_3$ | H |
| H | 2,4,5-Cl$_3$ | H |
| H | 2,3,6-Cl$_3$ | H |
| H | 2,3,4,5-Cl$_4$ | H |
| H | 2,3,4,6-Cl$_4$ | H |
| H | 2,3,5,6-Cl$_4$ | H |
| H | Cl$_5$ | H |
| H | 2,4,6-Br$_3$ | H |
| H | 2,3,5-Br$_3$ | H |
| H | 2,3,4-Br$_3$ | H |

TABLE 2-continued

| | | |
|---|---|---|
| H | 3,4,5-Br$_3$ | H |
| H | 2,4,5-Br$_3$ | H |
| H | 2,3,6-Br$_3$ | H |
| H | 2,4-I$_2$ | H |
| H | 3,4-I$_2$ | H |
| H | 3,5-I$_2$ | H |
| H | 2,6-I$_2$ | H |
| H | 2,3-I$_2$ | H |
| H | 2,5-I$_2$ | H |
| H | 2,4,6-I$_3$ | H |
| H | 2,3,5-I$_3$ | H |
| H | 2,3,4-I$_3$ | H |
| H | 3,4,5-I$_3$ | H |
| H | 2,4,5-I$_3$ | H |
| H | 2,3,6-I$_3$ | H |
| H | 2-Cl-3-F | H |
| H | 2-Cl-5-F | H |
| H | 3-Cl-2-F | H |
| H | 3-Cl-5-F | H |
| H | 3-Cl-6-F | H |
| H | 2-Br-3-F | H |
| H | 2-Br-5-F | H |
| H | 2-Br-6-F | H |
| H | 3-Br-2-F | H |
| H | 3-Br-5-F | H |
| H | 4-Br-2-F | H |
| H | 4-Br-3-F | H |
| H | 2-F-3-I | H |
| H | 2-F-4-I | H |
| H | 2-F-5-I | H |
| H | 2-F-6-I | H |
| H | 3-F-2-I | H |
| H | 3-F-4-I | H |
| H | 3-F-5-I | H |
| H | 3-F-6-I | H |
| H | 4-F-2-I | H |
| H | 4-F-3-I | H |
| H | 2-Br-3-Cl | H |
| H | 2-Br-4-Cl | H |
| H | 2-Br-5-Cl | H |
| H | 2-Br-6-Cl | H |
| H | 3-Br-2-Cl | H |
| H | 3-Br-4-Cl | H |
| H | 3-Br-5-Cl | H |
| H | 3-Br-6-Cl | H |
| H | 4-Br-2-Cl | H |
| H | 4-Br-3-Cl | H |
| H | 2-Br-3-I | H |
| H | 2-Br-4-I | H |
| H | 2-Br-5-I | H |
| H | 2-Br-6-I | H |
| H | 3-Br-2-I | H |
| H | 3-Br-4-I | H |
| H | 3-Br-5-I | H |
| H | 3-Br-6-I | H |
| H | 4-Br-2-I | H |
| H | 4-Br-3-I | H |
| H | 2-Cl-3,4-F$_2$ | H |
| H | 2-Cl-3,5-F$_2$ | H |
| H | 2-Cl-3,6-F$_2$ | H |
| H | 2-Cl-4,5-F$_2$ | H |
| H | 2-Cl-4,6-F$_2$ | H |
| H | 2-Cl-5,6-F$_2$ | H |
| H | 3-Cl-2,4-F$_2$ | H |
| H | 3-Cl-2,5-F$_2$ | H |
| H | 3-Cl-2,6-F$_2$ | H |
| H | 3-Cl-4,5-F$_2$ | H |
| H | 3-Cl-4,6-F$_2$ | H |
| H | 3-Cl-5,6-F$_2$ | H |
| H | 4-Cl-2,3-F$_2$ | H |
| H | 4-Cl-2,5-F$_2$ | H |
| H | 4-Cl-2,6-F$_2$ | H |
| H | 4-Cl-3,5-F$_2$ | H |
| H | 3,4-Cl$_2$-2-F | H |
| H | 3,5-Cl$_2$-2-F | H |
| H | 2,5-Cl$_2$-6-F | H |
| H | 3,4-Cl$_2$-6-F | H |
| H | 2,4-Cl$_2$-6-F | H |
| H | 2,3-Cl$_2$-6-F | H |
| H | 2,4-Cl$_2$-3-F | H |
| H | 2,5-Cl$_2$-3-F | H |
| H | 2,6-Cl$_2$-3-F | H |
| H | 3,4-Cl$_2$-5-F | H |
| H | 2,3-Cl$_2$-5-F | H |
| H | 2,3-Cl$_2$-4-F | H |
| H | 2,5-Cl$_2$-4-F | H |
| H | 2,6-Cl$_2$-4-F | H |
| H | 3,5-Cl$_2$-4-F | H |
| H | 2-Br-3,4-F$_2$ | H |
| H | 2-Br-3,5-F$_2$ | H |
| H | 2-Br-3,6-F$_2$ | H |
| H | 2-Br-4,5-F$_2$ | H |
| H | 2-Br-4,6-F$_2$ | H |
| H | 2-Br-5,6-F$_2$ | H |
| H | 3-Br-2,4-F$_2$ | H |
| H | 3-Br-2,5-F$_2$ | H |
| H | 3-Br-2,6-F$_2$ | H |
| H | 3-Br-4,5-F$_2$ | H |
| H | 3-Br-4,6-F$_2$ | H |
| H | 3-Br-5,6-F$_2$ | H |
| H | 4-Br-2,3-F$_2$ | H |
| H | 4-Br-2,5-F$_2$ | H |
| H | 4-Br-2,6-F$_2$ | H |
| H | 4-Br-3,5-F$_2$ | H |
| H | 3,4-Br$_2$-2-F | H |
| H | 3,5-Br$_2$-2-F | H |
| H | 2,5-Br$_2$-6-F | H |
| H | 3,4-Br$_2$-6-F | H |
| H | 2,4-Br$_2$-6-F | H |
| H | 2,3-Br$_2$-6-F | H |
| H | 2,4-Br$_2$-3-F | H |
| H | 2,5-Br$_2$-3-F | H |
| H | 2,6-Br$_2$-3-F | H |
| H | 3,4-Br$_2$-5-F | H |
| H | 2,4-Br$_2$-5-F | H |
| H | 2,3-Br$_2$-5-F | H |
| H | 2,3-Br$_2$-4-F | H |
| H | 2,5-Br$_2$-4-F | H |
| H | 2,6-Br$_2$-4-F | H |
| H | 3,5-Br$_2$-4-F | H |
| H | 3,4-F$_2$-2-I | H |
| H | 3,5-F$_2$-2-I | H |
| H | 2,5-F$_2$-6-I | H |
| H | 3,4-F$_2$-6-I | H |
| H | 2,4-F$_2$-6-I | H |
| H | 2,3-F$_2$-6-I | H |
| H | 2,4-F$_2$-3-I | H |
| H | 2,5-F$_2$-3-I | H |
| H | 2,6-F$_2$-3-I | H |
| H | 3,4-F$_2$-5-I | H |
| H | 2,4-F$_2$-5-I | H |
| H | 2,3-F$_2$-5-I | H |
| H | 2,3-F$_2$-4-I | H |
| H | 2,5-F$_2$-4-I | H |
| H | 2,6-F$_2$-4-I | H |
| H | 3,5-F$_2$-4-I | H |
| H | 2-F-3,4-I$_2$ | H |
| H | 2-F-3,5-I$_2$ | H |
| H | 2-F-3,6-I$_2$ | H |
| H | 2-F-4,5-I$_2$ | H |
| H | 2-F-4,6-I$_2$ | H |
| H | 2-F-5,6-I$_2$ | H |
| H | 3-F-2,4-I$_2$ | H |
| H | 3-F-2,5-I$_2$ | H |
| H | 3-F-2,6-I$_2$ | H |
| H | 5-F-3,4-I$_2$ | H |
| H | 5-F-2,4-I$_2$ | H |
| H | 5-F-2,3-I$_2$ | H |
| H | 4-F-2,3-I$_2$ | H |
| H | 4-F-2,5-I$_2$ | H |
| H | 4-F-2,6-I$_2$ | H |
| H | 4-F-3,5-I$_2$ | H |
| H | 2-Br-3,4-Cl$_2$ | H |
| H | 2-Br-3,5-Cl$_2$ | H |
| H | 2-Br-3,6-Cl$_2$ | H |
| H | 2-Br-4,5-Cl$_2$ | H |
| H | 6-Br-2,4-Cl$_2$ | H |
| H | 6-Br-2,3-Cl$_2$ | H |

TABLE 2-continued

| | | |
|---|---|---|
| H | 3-Br-2,4-Cl$_2$ | H |
| H | 3-Br-2,5-Cl$_2$ | H |
| H | 3-Br-2,6-Cl$_2$ | H |
| H | 3-Br-4,5-Cl$_2$ | H |
| H | 5-Br-2,4-Cl$_2$ | H |
| H | 5-Br-2,3-Cl$_2$ | H |
| H | 4-Br-2,3-Cl$_2$ | H |
| H | 4-Br-2,5-Cl$_2$ | H |
| H | 4-Br-2,6-Cl$_2$ | H |
| H | 4-Br-3,5-Cl$_2$ | H |
| H | 3,4-Br$_2$-2-Cl | H |
| H | 3,5-Br$_2$-2-Cl | H |
| H | 2,5-Br$_2$-6-Cl | H |
| H | 3,4-Br$_2$-6-Cl | H |
| H | 2,4-Br$_2$-6-Cl | H |
| H | 2,3-Br$_2$-6-Cl | H |
| H | 2,4-Br$_2$-3-Cl | H |
| H | 2,5-Br$_2$-3-Cl | H |
| H | 2,6-Br$_2$-3-Cl | H |
| H | 3,4-Br$_2$-5-Cl | H |
| H | 2,4-Br$_2$-5-Cl | H |
| H | 2,3-Br$_2$-5-Cl | H |
| H | 2,3-Br$_2$-4-Cl | H |
| H | 2,5-Br$_2$-4-Cl | H |
| H | 2,6-Br$_2$-4-Cl | H |
| H | 3,5-Br$_2$-4-Cl | H |
| H | 3,4-Cl$_2$-2-I | H |
| H | 3,5-Cl$_2$-2-I | H |
| H | 2,5-Cl$_2$-6-I | H |
| H | 3,4-Cl$_2$-6-I | H |
| H | 2,4-Cl$_2$-6-I | H |
| H | 2,3-Cl$_2$-6-I | H |
| H | 2,4-Cl$_2$-3-I | H |
| H | 2,5-Cl$_2$-3-I | H |
| H | 2,6-Cl$_2$-3-I | H |
| H | 3,4-Cl$_2$-5-I | H |
| H | 2,4-Cl$_2$-5-I | H |
| H | 2,3-Cl$_2$-5-I | H |
| H | 2,3-Cl$_2$-4-I | H |
| H | 2,5-Cl$_2$-4-I | H |
| H | 2,6-Cl$_2$-4-I | H |
| H | 3,5-Cl$_2$-4-I | H |
| H | 2-Cl-3,4-I$_2$ | H |
| H | 2-Cl-3,5-I$_2$ | H |
| H | 2-Cl-3,6-I$_2$ | H |
| H | 2-Cl-4,5-I$_2$ | H |
| H | 2-Cl-4,6-I$_2$ | H |
| H | 2-Cl-5,6-I$_2$ | H |
| H | 3-Cl-2,4-I$_2$ | H |
| H | 3-Cl-2,5-I$_2$ | H |
| H | 3-Cl-2,6-I$_2$ | H |
| H | 3-Cl-4,5-I$_2$ | H |
| H | 3-Cl-4,6-I$_2$ | H |
| H | 3-Cl-5,6-I$_2$ | H |
| H | 4-Cl-2,3-I$_2$ | H |
| H | 4-Cl-2,5-I$_2$ | H |
| H | 4-Cl-2,6-I$_2$ | H |
| H | 4-Cl-3,5-I$_2$ | H |
| H | 3,4-Br$_2$-2-I | H |
| H | 3,5-Br$_2$-2-I | H |
| H | 2,5-Br$_2$-6-I | H |
| H | 3,4-Br$_2$-6-I | H |
| H | 2,4-Br$_2$-6-I | H |
| H | 2,3-Br$_2$-6-I | H |
| H | 2,4-Br$_2$-3-I | H |
| H | 2,5-Br$_2$-3-I | H |
| H | 2,6-Br$_2$-3-I | H |
| H | 3,4-Br$_2$-5-I | H |
| H | 2,4-Br$_2$-5-I | H |
| H | 2,3-Br$_2$-5-I | H |
| H | 2,3-Br$_2$-4-I | H |
| H | 2,5-Br$_2$-4-I | H |
| H | 2,6-Br$_2$-4-I | H |
| H | 3,5-Br$_2$-4-I | H |
| H | 2-Br-3,4-I$_2$ | H |
| H | 2-Br-3,5-I$_2$ | H |
| H | 2-Br-3,6-I$_2$ | H |
| H | 2-Br-4,5-I$_2$ | H |
| H | 2-Br-4,6-I$_2$ | H |
| H | 2-Br-5,6-I$_2$ | H |
| H | 3-Br-2,4-I$_2$ | H |
| H | 3-Br-2,5-I$_2$ | H |
| H | 3-Br-2,6-I$_2$ | H |
| H | 3-Br-4,5-I$_2$ | H |
| H | 3-Br-4,6-I$_2$ | H |
| H | 3-Br-5,6-I$_2$ | H |
| H | 4-Br-2,3-I$_2$ | H |
| H | 4-Br-2,5-I$_2$ | H |
| H | 4-Br-2,6-I$_2$ | H |
| H | 4-Br-3,5-I$_2$ | H |
| H | 2-Cl-3,4,5-F$_3$ | H |
| H | 2-Cl-3,4,6-F$_3$ | H |
| H | 2-Cl-3,5,6-F$_3$ | H |
| H | 6-Cl-2,3,4-F$_3$ | H |
| H | 3-Cl-2,4,5-F$_3$ | H |
| H | 3-Cl-2,4,6-F$_3$ | H |
| H | 5-Cl-2,3,6-F$_3$ | H |
| H | 5-Cl-2,3,4-F$_3$ | H |
| H | 4-Cl-2,3,5-F$_3$ | H |
| H | 4-Cl-2,3,6-F$_3$ | H |
| H | 2,3-Cl$_2$-4,5-F$_2$ | H |
| H | 2,3-Cl$_2$-5,6-F$_2$ | H |
| H | 2,3-Cl$_2$-4,6-F$_2$ | H |
| H | 2,4-Cl$_2$-3,5-F$_2$ | H |
| H | 2,4-Cl$_2$-3,6-F$_2$ | H |
| H | 4,6-Cl$_2$-2,3-F$_2$ | H |
| H | 2,5-Cl$_2$-3,4-F$_2$ | H |
| H | 2,5-Cl$_2$-3,6-F$_2$ | H |
| H | 3,6-Cl$_2$-2,4-F$_2$ | H |
| H | 2,6-Cl$_2$-3,4-F$_2$ | H |
| H | 2,6-Cl$_2$-3,5-F$_2$ | H |
| H | 3,5-Cl$_2$-2,4-F$_2$ | H |
| H | 3,5-Cl$_2$-2,6-F$_2$ | H |
| H | 3,4,5-Cl$_3$-2-F | H |
| H | 3,4,6-Cl$_3$-2-F | H |
| H | 3,5,6-Cl$_3$-2-F | H |
| H | 2,3,4-Cl$_3$-6-F | H |
| H | 2,4,5-Cl$_3$-3-F | H |
| H | 2,4,6-Cl$_3$-3-F | H |
| H | 2,5,6-Cl$_3$-3-F | H |
| H | 2,3,4-Cl$_3$-5-F | H |
| H | 2,3,5-Cl$_3$-4-F | H |
| H | 2,3,6-Cl$_3$-4-F | H |
| H | 2-Br-3,4,5-F$_3$ | H |
| H | 2-Br-3,4,6-F$_3$ | H |
| H | 2-Br-3,5,6-F$_3$ | H |
| H | 6-Br-2,3,4-F$_3$ | H |
| H | 3-Br-2,4,5-F$_3$ | H |
| H | 3-Br-2,4,6-F$_3$ | H |
| H | 5-Br-2,3,6-F$_3$ | H |
| H | 5-Br-2,3,4-F$_3$ | H |
| H | 4-Br-2,3,5-F$_3$ | H |
| H | 4-Br-2,3,6-F$_3$ | H |
| H | 2,3-Br$_2$-4,5-F$_2$ | H |
| H | 2,3-Br$_2$-5,6-F$_2$ | H |
| H | 2,3-Br$_2$-4,6-F$_2$ | H |
| H | 2,4-Br$_2$-3,5-F$_2$ | H |
| H | 2,4-Br$_2$-3,6-F$_2$ | H |
| H | 4,6-Br$_2$-2,3-F$_2$ | H |
| H | 2,5-Br$_2$-3,4-F$_2$ | H |
| H | 2,5-Br$_2$-3,6-F$_2$ | H |
| H | 3,6-Br$_2$-2,4-F$_2$ | H |
| H | 2,6-Br$_2$-3,4-F$_2$ | H |
| H | 2,6-Br$_2$-3,5-F$_2$ | H |
| H | 3,5-Br$_2$-2,4-F$_2$ | H |
| H | 3,5-Br$_2$-2,6-F$_2$ | H |
| H | 3,4,6-Br$_3$-2-F | H |
| H | 3,5,6-Br$_3$-2-F | H |
| H | 2,3,4-Br$_3$-6-F | H |
| H | 2,4,5-Br$_3$-3-F | H |
| H | 2,4,6-Br$_3$-3-F | H |
| H | 2,5,6-Br$_3$-3-F | H |
| H | 2,3,4-Br$_3$-5-F | H |
| H | 2,3,5-Br$_3$-4-F | H |
| H | 2,3,6-Br$_3$-4-F | H |
| H | 3,4,5-F$_3$-2-I | H |
| H | 3,4,6-F$_3$-2-I | H |
| H | 3,5,6-F$_3$-2-I | H |

TABLE 2-continued

| | | |
|---|---|---|
| H | 2,3,4-F$_3$-6-I | H |
| H | 2,4,5-F$_3$-3-I | H |
| H | 2,4,6-F$_3$-3-I | H |
| H | 2,5,6-F$_3$-3-I | H |
| H | 2,3,4-F$_3$-5-I | H |
| H | 2,3,5-F$_3$-4-I | H |
| H | 2,3,6-F$_3$-4-I | H |
| H | 2,3-F$_2$-4,5-I$_2$ | H |
| H | 2,3-F$_2$-5,6-I$_2$ | H |
| H | 2,3-F$_2$-4,6-I$_2$ | H |
| H | 2,4-F$_2$-3,5-I$_2$ | H |
| H | 2,4-F$_2$-3,6-I$_2$ | H |
| H | 4,6-F$_2$-2,3-I$_2$ | H |
| H | 2,5-F$_2$-3,4-I$_2$ | H |
| H | 2,5-F$_2$-3,6-I$_2$ | H |
| H | 3,6-F$_2$-2,4-I$_2$ | H |
| H | 2,6-F$_2$-3,4-I$_2$ | H |
| H | 2,6-F$_2$-3,5-I$_2$ | H |
| H | 3,5-F$_2$-2,4-I$_2$ | H |
| H | 3,5-F$_2$-2,6-I$_2$ | H |
| H | 2-F-3,4,5-I$_3$ | H |
| H | 2-F-3,5,6-I$_3$ | H |
| H | 6-F-2,3,4-I$_3$ | H |
| H | 3-F-2,4,5-I$_3$ | H |
| H | 3-F-2,4,6-I$_3$ | H |
| H | 5-F-2,3,6-I$_3$ | H |
| H | 5-F-2,3,4-I$_3$ | H |
| H | 4-F-2,3,5-I$_3$ | H |
| H | 4-F-2,3,6-I$_3$ | H |
| H | 2-Br-3,4,5-Cl$_3$ | H |
| H | 2-Br-3,4,6-Cl$_3$ | H |
| H | 2-Br-3,5,6-Cl$_3$ | H |
| H | 6-Br-2,3,4-Cl$_3$ | H |
| H | 3-Br-2,4,5-Cl$_3$ | H |
| H | 3-Br-2,4,6-Cl$_3$ | H |
| H | 5-Br-2,3,6-Cl$_3$ | H |
| H | 5-Br-2,3,4-Cl$_3$ | H |
| H | 4-Br-2,3,5-Cl$_3$ | H |
| H | 4-Br-2,3,6-Cl$_3$ | H |
| H | 2,3-Br$_2$-4,5-Cl$_2$ | H |
| H | 2,3-Br$_2$-5,6-Cl$_2$ | H |
| H | 2,3-Br$_2$-4,6-Cl$_2$ | H |
| H | 2,4-Br$_2$-3,5-Cl$_2$ | H |
| H | 2,4-Br$_2$-3,6-Cl$_2$ | H |
| H | 4,6-Br$_2$-2,3-Cl$_2$ | H |
| H | 2,5-Br$_2$-3,4-Cl$_2$ | H |
| H | 2,5-Br$_2$-3,6-Cl$_2$ | H |
| H | 3,6-Br$_2$-2,4-Cl$_2$ | H |
| H | 2,6-Br$_2$-3,4-Cl$_2$ | H |
| H | 2,6-Br$_2$-3,5-Cl$_2$ | H |
| H | 3,5-Br$_2$-2,4-Cl$_2$ | H |
| H | 3,5-Br$_2$-2,6-Cl$_2$ | H |
| H | 3,4,5-Br$_3$-2-Cl | H |
| H | 3,4,6-Br$_3$-2-Cl | H |
| H | 3,5,6-Br$_3$-2-Cl | H |
| H | 2,3,4-Br$_3$-6-Cl | H |
| H | 2,4,5-Br$_3$-3-Cl | H |
| H | 2,4,6-Br$_3$-3-Cl | H |
| H | 2,5,6-Br$_3$-3-Cl | H |
| H | 2,3,4-Br$_3$-5-Cl | H |
| H | 2,3,5-Br$_3$-4-Cl | H |
| H | 2,3,6-Br$_3$-4-Cl | H |
| H | 3,4,5-Cl$_3$-2-I | H |
| H | 3,4,6-Cl$_3$-2-I | H |
| H | 3,5,6-Cl$_3$-2-I | H |
| H | 2,3,4-Cl$_3$-6-I | H |
| H | 2,4,5-Cl$_3$-3-I | H |
| H | 2,4,6-Cl$_3$-3-I | H |
| H | 2,5,6-Cl$_3$-3-I | H |
| H | 2,3,4-Cl$_3$-5-I | H |
| H | 2,3,5-Cl$_3$-4-I | H |
| H | 2,3,6-Cl$_3$-4-I | H |
| H | 2,3-Cl$_2$-4,5-I$_2$ | H |
| H | 2,3-Cl$_2$-5,6-I$_2$ | H |
| H | 2,3-Cl$_2$-4,6-I$_2$ | H |
| H | 2,4-Cl$_2$-3,5-I$_2$ | H |
| H | 2,4-Cl$_2$-3,6-I$_2$ | H |
| H | 4,6-Cl$_2$-2,3-I$_2$ | H |
| H | 2,5-Cl$_2$-3,4-I$_2$ | H |
| H | 2,5-Cl$_2$-3,6-I$_2$ | H |
| H | 3,6-Cl$_2$-2,4-I$_2$ | H |
| H | 2,6-Cl$_2$-3,4-I$_2$ | H |
| H | 2,6-Cl$_2$-3,5-I$_2$ | H |
| H | 3,5-Cl$_2$-2,4-I$_2$ | H |
| H | 3,5-Cl$_2$-2,6-I$_2$ | H |
| H | 3,4,5-Br$_3$-2-I | H |
| H | 3,4,6-Br$_3$-2-I | H |
| H | 3,5,6-Br$_3$-2-I | H |
| H | 2,3,4-Br$_3$-6-I | H |
| H | 2,4,5-Br$_3$-3-I | H |
| H | 2,4,6-Br$_3$-3-I | H |
| H | 2,5,6-Br$_3$-3-I | H |
| H | 2,3,4-Br$_3$-5-I | H |
| H | 2,3,5-Br$_3$-4-I | H |
| H | 2,3,6-Br$_3$-4-I | H |
| H | 2,3-Br$_2$-4,5-I$_2$ | H |
| H | 2,3-Br$_2$-5,6-I$_2$ | H |
| H | 2,3-Br$_2$-4,6-I$_2$ | H |
| H | 2,4-Br$_2$-3,5-I$_2$ | H |
| H | 2,4-Br$_2$-3,6-I$_2$ | H |
| H | 4,6-Br$_2$-2,3-I$_2$ | H |
| H | 2,5-Br$_2$-3,4-I$_2$ | H |
| H | 2,5-Br$_2$-3,6-I$_2$ | H |
| H | 3,6-Br$_2$-2,4-I$_2$ | H |
| H | 2,6-Br$_2$-3,4-I$_2$ | H |
| H | 2,6-Br$_2$-3,5-I$_2$ | H |
| H | 3,5-Br$_2$-2,4-I$_2$ | H |
| H | 3,5-Br$_2$-2,6-I$_2$ | H |
| H | 2-Cl-3,4,5,6-F$_4$ | H |
| H | 3-Cl-2,4,5,6-F$_4$ | H |
| H | 4-Cl-2,3,5,6-F$_4$ | H |
| H | 2,4-Cl$_2$-3,5,6-F$_3$ | H |
| H | 3,4-Cl$_2$-2,5,6-F$_3$ | H |
| H | 3,5-Cl$_2$-2,4,6-F$_3$ | H |
| H | 2,6-Cl$_2$-3,4,5-F$_3$ | H |
| H | 2,3-Cl$_2$-4,5,6-F$_3$ | H |
| H | 2,5-Cl$_2$-3,4,6-F$_3$ | H |
| H | 2,4,6-Cl$_3$-3,5-F$_2$ | H |
| H | 2,3,5-Cl$_3$-4,6-F$_2$ | H |
| H | 2,3,4-Cl$_3$-5,6-F$_2$ | H |
| H | 3,4,5-Cl$_3$-2,6-F$_2$ | H |
| H | 2,4,5-Cl$_3$-3,6-F$_2$ | H |
| H | 2,3,6-Cl$_3$-4,5-F$_2$ | H |
| H | 2,3,4,5-Cl$_4$-6-F | H |
| H | 2,3,4,6-Cl$_4$-5-F | H |
| H | 2,3,5,6-Cl$_4$-4-F | H |
| H | 2-Br-3,4,5,6-F$_4$ | H |
| H | 3-Br-2,4,5,6-F$_4$ | H |
| H | 4-Br-2,3,5,6-F$_4$ | H |
| H | 2,4-Br$_2$-3,5,6-F$_3$ | H |
| H | 3,4-Br$_2$-2,5,6-F$_3$ | H |
| H | 3,5-Br$_2$-2,4,6-F$_3$ | H |
| H | 2,6-Br$_2$-3,4,5-F$_3$ | H |
| H | 2,3-Br$_2$-4,5,6-F$_3$ | H |
| H | 2,5-Br$_2$-3,4,6-F$_3$ | H |
| H | 2,4,6-Br$_3$-3,5-F$_2$ | H |
| H | 2,3,5-Br$_3$-4,6-F$_2$ | H |
| H | 2,3,4-Br$_3$-5,6-F$_2$ | H |
| H | 3,4,5-Br$_3$-2,6-F$_2$ | H |
| H | 2,4,5-Br$_3$-3,6-F$_2$ | H |
| H | 2,3,6-Br$_3$-4,5-F$_2$ | H |
| H | 2,3,4,5-Br$_4$-6-F | H |
| H | 2,3,4,6-Br$_4$-5-F | H |
| H | 2,3,5,6-Br$_4$-4-F | H |
| H | 2-I-3,4,5,6-F$_4$ | H |
| H | 3-I-2,4,5,6-F$_4$ | H |
| H | 4-I-2,3,5,6-F$_4$ | H |
| H | 2-Br-3,4,5,6-Cl$_4$ | H |
| H | 3-Br-2,4,5,6-Cl$_4$ | H |
| H | 4-Br-2,3,5,6-Cl$_4$ | H |
| H | 2,4-Br$_2$-3,5,6-Cl$_3$ | H |
| H | 3,4-Br$_2$-2,5,6-Cl$_3$ | H |
| H | 3-Br-4-Me | H |
| H | 4-F-3,5-Me$_2$ | H |
| H | 4-Cl-3,5-Me$_2$ | H |
| H | 4-Br-3,5-Me$_2$ | H |
| H | 2-MeO | H |
| H | 4-F-3-MeO | H |

TABLE 2-continued

| | | |
|---|---|---|
| H | 3-F-4-MeO | H |
| H | 4-Cl-3-MeO | H |
| H | 3-Cl-4-MeO | H |
| H | 4-Br-3-MeO | H |
| H | 3-Br-4-MeO | H |
| H | 4-F-3,5-(MeO)$_2$ | H |
| H | 4-Cl-3,5-(MeO)$_2$ | H |
| H | 4-Br-3,5-(MeO)$_2$ | H |
| H | 2-CF$_3$ | H |
| H | 3-F-5-CF$_3$ | H |
| H | 3-Cl-4-CF$_3$ | H |
| H | 2,4-(CF$_3$)$_2$ | H |
| H | 3,5-(CF$_3$)$_2$ | H |
| H | 2,6-(CF$_3$)$_2$ | H |
| H | 2,3-(CF$_3$)$_2$ | H |
| H | 2,5-(CF$_3$)$_2$ | H |
| H | 4-F-3,5-(CF$_3$)$_2$ | H |
| H | 4-Cl-3,5-(CF$_3$)$_2$ | H |
| H | 4-Br-3,5-(CF$_3$)$_2$ | H |
| H | 3-OCH$_2$F | H |
| H | 4-OCH$_2$F | H |
| H | 2-Me$_2$N | H |
| H | 4-Me$_2$N | H |
| H | 3,5-(Me$_2$N)$_2$ | H |
| H | 4-F-3,5-(Me$_2$N)$_2$ | H |
| H | 4-Cl-3,5-(Me$_2$N)$_2$ | H |
| H | 4-Br-3,5-(Me$_2$N)$_2$ | H |
| H | 2-NO$_2$ | H |
| H | 3,5-(NO$_2$)$_2$ | H |
| H | 4-F-3,5-(NO$_2$)$_2$ | H |
| H | 4-Br-3,5-(NO$_2$)$_2$ | H |
| H | 4-F-3-CN | H |
| H | 3-CN | H |
| H | 3,5-(CN)$_2$ | H |
| H | 4-F-3,5-(CN)$_2$ | H |
| H | 4-Cl-3,5-(CN)$_2$ | H |
| H | 4-Br-3,5-(CN)$_2$ | H |
| H | 2-CO$_2$Me | H |
| H | 3-CO$_2$Me | H |
| H | 4-CO$_2$Me | H |
| H | 4-F-3-CO$_2$Me | H |
| H | 4-Cl-3-CO$_2$Me | H |
| H | 4-F-3,5-(CO$_2$Me)$_2$ | H |
| H | 4-Cl-3,5-(CO$_2$Me)$_2$ | H |
| H | 2-Ph | H |
| H | 3-Ph | H |
| H | 4-Ph | H |
| H | 2,4-Ph$_2$ | H |
| H | 3,5-Ph$_2$ | H |
| H | 2,6-Ph$_2$ | H |
| H | 2,3-Ph$_2$ | H |
| H | 2,5-Ph$_2$ | H |
| H | 4-F-3-Ph | H |
| H | 3-F-4-Ph | H |
| H | 4-Cl-3-Ph | H |
| H | 3-Cl-4-Ph | H |
| H | 4-Br-3-Ph | H |
| H | 3-Br-4-Ph | H |
| H | 4-F-3,5-Ph$_2$ | H |
| H | 4-Cl-3,5-Ph$_2$ | H |
| H | 4-Br-3,5-Ph$_2$ | H |
| H | 2-PhO | H |
| H | 2,4-(PhO)$_2$ | H |
| H | 3,5-(PhO)$_2$ | H |
| H | 2,6-(PhO)$_2$ | H |
| H | 2,3-(PhO)$_2$ | H |
| H | 2,5-(PhO)$_2$ | H |
| H | 4-F-3-PhO | H |
| H | 3-F-4-PhO | H |
| H | 4-Cl-3-PhO | H |
| H | 3-Cl-4-PhO | H |
| H | 4-Br-3-PhO | H |
| H | 3-Br-4-PhO | H |
| H | 4-F-3,5-(PhO)$_2$ | H |
| H | 4-Cl-3,5-(PhO)$_2$ | H |
| H | 4-Br-3,5-(PhO)$_2$ | H |
| CH$_2$OMe | 3,4-Cl$_2$ | H |
| CH$_2$OMe | 3-Cl-4-F | H |
| CH$_2$OMe | 3-CF$_3$ | H |
| CH$_2$OMe | 3,5-Cl$_2$ | H |
| CH$_2$OMe | 3-Cl-4-F | H |
| CH$_2$OMe | 3,4,5-Cl$_3$ | H |
| CH$_2$OMe | 3,5-Cl$_2$-4-Br | H |
| CH$_2$OMe | 3,5-Cl$_2$-4-I | H |
| CH$_2$OMe | 3,5-(CF$_3$)$_2$ | H |
| CH$_2$OMe | 3,5-F$_2$ | H |
| CH$_2$OMe | 3,5-Cl$_2$-4-F | H |
| CH$_2$OMe | 3,5-Br$_2$-4-Cl | H |
| CH$_2$OMe | 3,4,5-F$_3$ | H |
| CH$_2$OMe | 3,4-F$_2$ | H |
| CH$_2$OMe | 3,5-Br$_2$ | H |
| CH$_2$OMe | 3,5-Br$_2$-4-F | H |
| CH$_2$OMe | 3-Br-5-I | H |
| CH$_2$OMe | 3,4-Cl$_2$ | H |
| CH$_2$OMe | 3-Cl-4-F | H |
| CH$_2$OMe | 3-CF$_3$ | H |
| CH$_2$OEt | 3,5-Cl$_2$ | H |
| CH$_2$OEt | 3-Cl-4-F | H |
| CH$_2$OEt | 3,4,5-Cl$_2$ | H |
| CH$_2$OEt | 3,5-Cl$_2$-4-Br | H |
| CH$_2$OEt | 3,5-Cl$_2$-4-I | H |
| CH$_2$OEt | 3,5-(CF$_3$)$_2$ | H |
| CH$_2$OEt | 3,5-F$_2$ | H |
| CH$_2$OEt | 3,5-Cl$_2$-4-F | H |
| CH$_2$OEt | 3,5-Br$_2$-4-Cl | H |
| CH$_2$OEt | 3,4,5-F$_3$ | H |
| CH$_2$OEt | 3,4-F$_2$ | H |
| CH$_2$OEt | 3,5-Br$_2$ | H |
| CH$_2$OEt | 3,5-Br$_2$-4-F | H |
| CH$_2$OEt | 3-Br-5-I | H |
| CH$_2$O(Pr-n) | 3,5-Cl$_2$ | H |
| CH$_2$O(Pr-n) | 3-Cl-4-F | H |
| CH$_2$O(Pr-n) | 3,4,5-Cl$_3$ | H |
| CH$_2$O(Pr-n) | 3,5-Cl$_2$-4-Br | H |
| CH$_2$O(Pr-n) | 3,5-Cl$_2$-4-I | H |
| CH$_2$O(Pr-n) | 3,5-(CF$_3$)$_2$ | H |
| CH$_2$O(Pr-n) | 3,5-F$_2$ | H |
| CH$_2$O(Pr-n) | 3,5-Cl$_2$-4-F | H |
| CH$_2$O(Pr-n) | 3,5-Br$_2$-4-Cl | H |
| CH$_2$O(Pr-n) | 3,4,5-F$_3$ | H |
| CH$_2$O(Pr-n) | 3,4-F$_2$ | H |
| CH$_2$O(Pr-n) | 3,5-Br$_2$ | H |
| CH$_2$O(Pr-n) | 3,5-Br$_2$-4-F | H |
| CH$_2$O(Pr-n) | 3-Br-5-I | H |
| CH$_2$O(Pr-iso) | 3,5-Cl$_2$ | H |
| CH$_2$O(Pr-iso) | 3,4,5-Cl$_3$ | H |
| CH$_2$O(Pr-iso) | 3,5-F$_2$ | H |
| CH$_2$O(Pr-iso) | 3,5-Cl$_2$-4-F | H |
| CH$_2$O(Pr-iso) | 3,4-Cl$_2$ | H |
| CH$_2$O(Pr-iso) | 3,5-Br$_2$ | H |
| CH$_2$O(Pr-iso) | 3,5-Br$_2$-4-F | H |
| CH$_2$OC$_2$H$_4$OMe | 3,5-Cl$_2$ | H |
| CH$_2$OC$_2$H$_4$OMe | 3,4,5-Cl$_3$ | H |
| CH$_2$OC$_2$H$_4$OMe | 3,5-F$_2$ | H |
| CH$_2$OC$_2$H$_4$OMe | 3,5-Cl$_2$-4-F | H |
| CH$_2$OC$_2$H$_4$OMe | 3,4-Cl$_2$ | H |
| CH$_2$OC$_2$H$_4$OMe | 3,5-Br$_2$ | H |
| CH$_2$OC$_2$H$_4$OMe | 3,5-Br$_2$-4-F | H |
| CH$_2$OC$_2$H$_4$OEt | 3,5-Cl$_2$ | H |
| CH$_2$OC$_2$H$_4$OEt | 3,4,5-Cl$_2$ | H |
| CH$_2$OC$_2$H$_4$OEt | 3,5-F$_2$ | H |
| CH$_2$OC$_2$H$_4$OEt | 3,5-Cl$_2$-4-F | H |
| CH$_2$OC$_2$H$_4$OEt | 3,4-Cl$_2$ | H |
| CH$_2$OC$_2$H$_4$OEt | 3,5-Br$_2$ | H |
| CH$_2$OC$_2$H$_4$OEt | 3,5-Br$_2$-4-F | H |
| CH$_2$O(Bu-n) | 3,5-Cl$_2$ | H |
| CH$_2$O(Bi-iso) | 3,5-Cl$_2$ | H |
| CH$_2$O(Bu-sec) | 3,5-Cl$_2$ | H |
| CH$_2$O(Bu-tert) | 3,5-Cl$_2$ | H |
| CH$_2$OCH$_2$CH$_2$O(Pr-n) | 3,5-Cl$_2$ | H |
| CH$_2$OCH$_2$CH$_2$O(Pr-iso) | 3,5-Cl$_2$ | H |
| MeCO | 3,5-Cl$_2$ | H |
| MeCO | 3,4-Cl$_2$ | H |
| MeCO | 3,4,5-Cl$_2$ | H |
| MeCO | 3,5-F$_2$ | H |
| MeCO | 3,5-Cl$_2$-4-F | H |
| MeCO | 3,5-Br$_2$ | H |
| MeCO | 3,5-Br$_2$-4-F | H |

TABLE 2-continued

| | | |
|---|---|---|
| MeCO | 4-Br | H |
| EtCO | 3,5-Cl$_2$ | H |
| EtCO | 3,4-Cl$_2$ | H |
| EtCO | 3,4,5-Cl$_3$ | H |
| EtCO | 3,5-F$_2$ | H |
| EtCO | 3,5-Cl$_2$-4-F | H |
| EtCO | 3,5-Br$_2$ | H |
| EtCO | 3,5-Br$_2$-4-F | H |
| (Pr-n)CO | 3,5-Cl$_2$ | H |
| (Bu-n)CO | 3,5-Cl$_2$ | H |
| PhCO | 3,5-Cl$_2$ | H |
| PhCO | 3,4-Cl$_2$ | H |
| PhCO | 3,4,5-Cl$_3$ | H |
| PhCO | 3,5-F$_2$ | H |
| PhCO | 3,5-Cl$_2$-4-F | H |
| PhCO | 3,5-Br$_2$ | H |
| PhCO | 3,5-Br$_2$-4-F | H |
| MeOCO | 3,5-Cl$_2$ | H |
| MeOCO | 3,4-Cl$_2$ | H |
| MeOCO | 3,4,5-Cl$_3$ | H |
| MeOCO | 3,5-F$_2$ | H |
| MeOCO | 3,5-Cl$_2$-4-F | H |
| MeOCO | 3,5-Br$_2$ | H |
| MeOCO | 3,5-Br$_2$-4-F | H |
| EtOCO | 3,5-Cl$_2$ | H |
| (Pr-n)OCO | 3,5-Cl$_2$ | H |
| (Bu-n)OCO | 3,5-Cl$_2$ | H |
| MeSO$_2$ | 3,5-Cl$_2$ | H |
| MeSO$_2$ | 3,4-Cl$_2$ | H |
| MeSO$_2$ | 3,4,5-Cl$_3$ | H |
| MeSO$_2$ | 3,5-F$_2$ | H |
| MeSO$_2$ | 3,5-Cl$_2$-4-F | H |
| MeSO$_2$ | 3,5-Br$_2$ | H |
| MeSO$_2$ | 3,5-Br$_2$-4-F | H |
| MeSO$_2$ | 3-Cl-4-MeO | H |
| EtSO$_2$ | 3,5-Cl$_2$ | H |
| (Pr-n)SO$_2$ | 3,5-Cl$_2$ | H |
| (Bu-n)SO$_2$ | 3,5-Cl$_2$ | H |
| Me$_2$NSO$_2$ | 3,5-Cl$_2$ | H |
| Me$_2$NSO$_2$ | 3,4-Cl$_2$ | H |
| Me$_2$NSO$_2$ | 3,4,5-Cl$_3$ | H |
| Me$_2$NSO$_2$ | 3,5-F$_2$ | H |
| Me$_2$NSO$_2$ | 3,5-Cl$_2$-4-F | H |
| Me$_2$NSO$_2$ | 3,5-Br$_2$ | H |
| Me$_2$NSO$_2$ | 3,5-Br$_2$-4-F | H |
| Me$_2$NSO$_2$ | 3-Cl-4-MeO | H |
| Et$_2$NSO$_2$ | 3,5-Cl$_2$ | H |
| (Pr-n)$_2$NSO$_2$, | 3,5-Cl$_2$ | H |
| (Bu-n)$_2$NSO$_2$, | 3,5-Cl$_2$ | H |
| Me$_2$NCO | 3,5-Cl$_2$ | H |
| Me$_2$NCO | 3,4-Cl$_2$ | H |
| Me$_2$NCO | 3,4,5-Cl$_3$ | H |
| Me$_2$NCO | 3,5-F$_2$ | H |
| Me$_2$NCO | 3,5-Cl$_2$-4-F | H |
| Me$_2$NCO | 3,5-Br$_2$ | H |
| Me$_2$NCO | 3,5-Br$_2$-4-F | H |
| Et$_2$NCO | 3,5-Cl$_2$ | H |
| Et$_2$NCO | 4-F | H |
| (Pr-n)$_2$NCO | 3,5-Cl$_2$ | H |
| (Bu-n)$_2$NCO | 3,5-Cl$_2$ | H |
| MeNHCO | 3,5-Cl$_2$ | H |
| MeNHCO | 3,4-Cl$_2$ | H |
| MeNHCO | 3,4,5-Cl$_3$ | H |
| MeNHCO | 3,5-F$_2$ | H |
| MeNHCO | 3,5-Cl$_2$-4-F | H |
| MeNHCO | 3,5-Br$_2$ | H |
| MeNHCO | 3,5-Br$_2$-4-F | H |
| EtNHCO | 3,5-Cl$_2$ | H |
| (Pr-n)NHCO | 3,5-Cl$_2$ | H |
| (Bu-n)NHCO | 3,5-Cl$_2$ | H |

TABLE 3

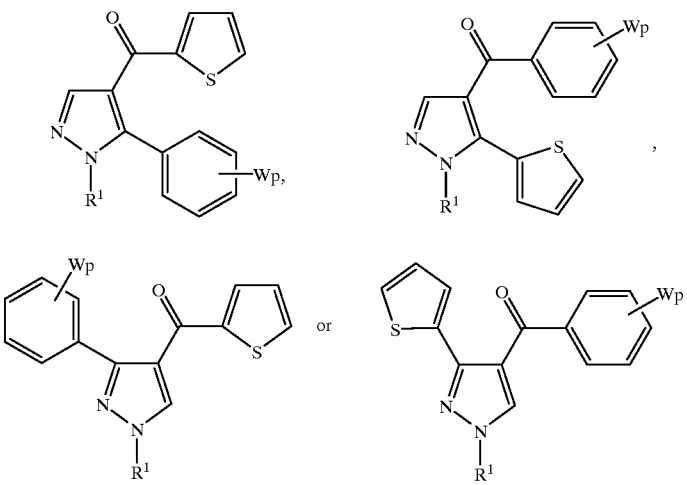

| $R^1$ | $W_P$ | $R^1$ | $W_P$ |
|---|---|---|---|
| H | H | H | 3-OMe |
| H | 2-F | H | 4-OMe |
| H | 3-F | H | 3-OEt |
| H | 4-F | H | 3-O(Pr-iso) |
| H | 2-Cl | H | 4-O(Pr-iso) |
| H | 3-Cl | H | 3-O(Bu-n) |
| H | 4-Cl | H | 4-O(Bu-n) |

TABLE 3-continued

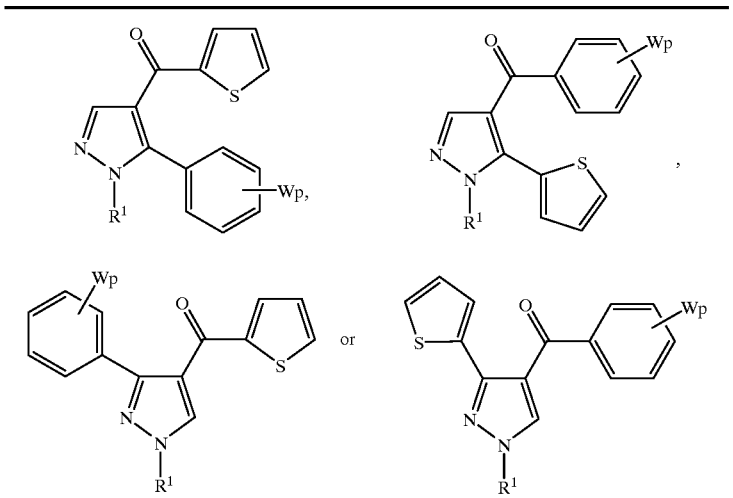

| R¹ | W_P | R¹ | W_P |
|---|---|---|---|
| H | 2-Br | H | 3-O(Bu-iso) |
| H | 3-Br | H | 3-O(Bu-tert) |
| H | 4-Br | H | 2-CN |
| H | 2-I | H | 3-CN |
| H | 3-I | H | 4-CN |
| H | 4-I | H | 3-OPh |
| H | 2-Me | H | 4-OPh |
| H | 3-Me | H | 3-NO₂ |
| H | 4-Me | H | 4-NO₂ |
| H | 2-Et | H | 3-CF₃ |
| H | 3-Et | H | 4-CF₃ |
| H | 4-Et | H | 3-CH₂F |
| H | 2-nPr | H | 3-CH₂Cl |
| H | 3-nPr | H | 3-CH₂Br |
| H | 4-nPr | H | 3-CH₂I |
| H | 3-iPr | H | 3-CHF₂ |
| H | 4-(pr-iso) | H | 3-CHCl₂ |
| H | 4-(Bu-tert) | H | 3-CCl₃ |
| H | 3-(Bu-tert) | H | 3-CH₂CH₂F |
| H | 4-(Bu-n) | H | 3-CH₂CH₂Cl |
| H | 3-(Bu-iso) | H | 3-CH₂CH₂Br |
| H | 3-(Bu-sec) | H | 3-CF₂Cl |
| H | 3-CH₂CF₃ | H | 3-OCH₂CH₂CH₂CH₂F |
| H | 3-CF₂CF₂CF₃ | H | 4-OCHF₂ |
| H | 3-CF₂CF₂CF₂CF₃ | H | 4-OCF₃ |
| H | 4-CH₂F | H | 4-OCClF₂ |
| H | 4-CH₂Cl | H | 4-OCBrF₂ |
| H | 4-CH₂Br | H | 4-OCF₂CHF₂ |
| H | 4-CH₂I | H | 4-OCH₂CH₂F |
| H | 4-CHF₂ | H | 4-OCH₂CH₂Cl |
| H | 4-CHCl₂ | H | 4-OCH₂CH₂Br |
| H | 4-CCl₃ | H | 4-OCH₂CH₂I |
| H | 4-CH₂CH₂F | H | 4-OCH₂CF₃ |
| H | 4-CH₂CH₂Cl | H | 4-OCH₂CCl₃ |
| H | 4-CH₂CH₂Br | H | 4-OCF(CH₃)₂ |
| H | 4-CF₂Cl | H | 4-OCH₂CH₂CH₂CH₂F |
| H | 4-CH₂CF₃ | H | 3-NMe₂ |
| H | 4-CF₂CF₂CF₃ | H | 3-NEt₂ |
| H | 4-CF₂CF₂CF₂CF₃ | H | 4-N(Pr-n)₂ |
| H | 3-OCHF₂ | H | 3-N(Bu-n)₂ |
| H | 3-OCF₃ | H | 3-N(Pr-iso)₂ |
| H | 3-OCClF₂ | H | 2,4-Cl₂ |
| H | 3-OCBrF₂ | H | 2,3-Cl₂ |
| H | 3-OCF₂CHF₂ | H | 2,5-Cl₂ |
| H | 3-OCH₂CH₂F | H | 2,6-Cl₂ |
| H | 3-OCH₂CH₂Cl | H | 3,4-Cl₂ |
| H | 3-OCH₂CH₂Br | H | 3,5-Cl₂ |
| H | 3-OCH₂CH₂I | H | 2,4-F |
| H | 3-OCH₂CF₃ | H | 2,3-F |
| H | 3-OCH₂CCl₃ | H | 2,5-F |
| H | 3-OCF(CH₃)₂ | H | 2,6-F |
| H | 3,4-F | H | 4-Cl-2-NO₂ |
| H | 3,5-F | H | 5-Cl-2-NO₂ |

TABLE 3-continued

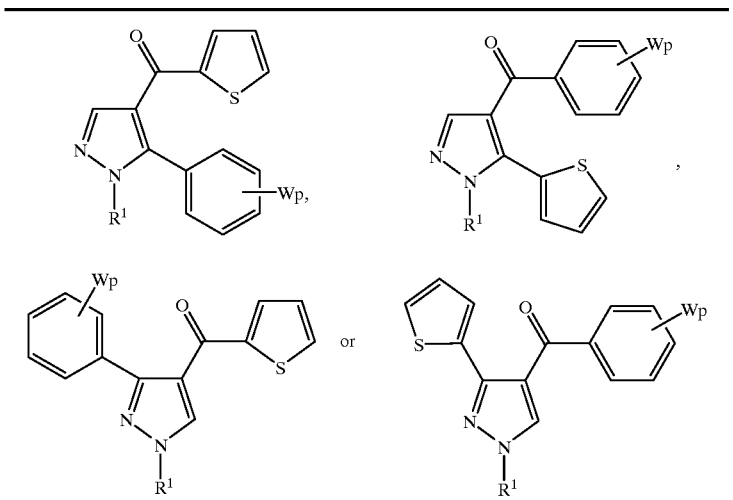

| R¹ | W_P | R¹ | W_P |
|---|---|---|---|
| H | 2,4-Br$_2$ | H | 4-Cl-3-NO$_2$ |
| H | 2,3-Br$_2$ | H | 4-Cl-3-OPh |
| H | 2,5-Br$_2$ | H | 4-OMe-3-NO$_2$ |
| H | 2,6-Br$_2$ | H | 2,3,5-Cl$_3$ |
| H | 3,4-Br$_2$ | H | 2,4,6-Cl$_3$ |
| H | 3,5-Br$_2$ | H | 3,4,5-Cl$_3$ |
| H | 2,4-Me | H | 2,3,4-F$_3$ |
| H | 2,3-Me | H | 2,3,6-F$_3$ |
| H | 2,5-Me | H | 2,4,5-F$_3$ |
| H | 2,6-Me | H | 3,4,5-F$_3$ |
| H | 3,4-Me | H | 3,4,5-(OMe)$_3$ |
| H | 3,5-Me | H | 3,4,5-(OEt)$_3$ |
| H | 2-F-4-Cl | H | 2,4-Cl$_2$-5-F |
| H | 3-F-4-Cl | H | 2,4-Cl$_2$-3,5-NO$_2$ |
| H | 3-Cl-4-F | H | 2,3,4,5,6-F$_5$ |
| H | 2-Cl-4-F | H | 2-Cl-3,5-(NO$_2$)$_2$ |
| H | 2-Cl-6-F | H | 4-Cl-3,5-(NO$_2$)$_2$ |
| H | 2-F-4-Br | CH$_2$OMe | H |
| H | 2-Br-4-F | CH$_2$OMe | 2-F |
| H | 3-Br-4-F | CH$_2$OMe | 3-F |
| H | 2-F-5-Br | CH$_2$OMe | 4-F |
| H | 4-Me-3-NO$_2$ | CH$_2$OMe | 2-Cl |
| H | 2-OMe-4-Cl | CH$_2$OMe | 3-Cl |
| H | 2-OMe-5-Cl | CH$_2$OMe | 4-Cl |
| H | 3,4-(OMe)$_2$ | CH$_2$OMe | 2-Br |
| H | 2-Cl-3-NO$_2$ | CH$_2$OMe | 3-Br |
| H | 2-Cl-4-NO$_2$ | CH$_2$OMe | 4-Br |
| CH$_2$OMe | 2-I | CH$_2$O(Pr-iso) | 3-Cl |
| CH$_2$OMe | 3-I | CH$_2$O(Pr-iso) | 3-Br |
| CH$_2$OMe | 4-I | CH$_2$O(Pr-iso) | 3-I |
| CH$_2$OMe | 2-Me | CH$_2$O(Pr-iso) | 3,4-Cl$_2$ |
| CH$_2$OMe | 3-Me | CH$_2$O(Pr-iso) | 3-CF$_3$ |
| CH$_2$OMe | 3-OCF$_3$ | CH$_2$O(Pr-iso) | 3-Cl-4-CF$_3$ |
| CH$_2$OMe | 3-OCClF$_2$ | CH$_2$OC$_2$H$_4$OMe | 3-Cl |
| CH$_2$OMe | 3-OCBrF$_2$ | CH$_2$OC$_2$H$_4$OMe | 3-Br |
| CH$_2$OMe | 4-CF$_3$ | CH$_2$OC$_2$H$_4$OMe | 3-I |
| CH$_2$OMe | 3,4-Cl$_2$ | CH$_2$OC$_2$H$_4$OMe | 3,4-Cl$_2$ |
| CH$_2$OMe | 3-Cl-4-F | CH$_2$OC$_2$H$_4$OMe | 3-CF$_3$ |
| CH$_2$OMe | 3-CF$_3$ | CH$_2$OC$_2$H$_4$OMe | 3-Cl-4-CF$_3$ |
| CH$_2$OEt | 2-Cl | CH$_2$OC$_2$H$_4$OEt | 3-Cl |
| CH$_2$OEt | 3-Cl | CH$_2$OC$_2$H$_4$OEt | 3-Br |
| CH$_2$OEt | 4-Cl | CH$_2$OC$_2$H$_4$OEt | 3-I |
| CH$_2$OEt | 2-Br | CH$_2$OC$_2$H$_4$OEt | 3,4-Cl$_2$ |
| CH$_2$OEt | 3-Br | CH$_2$OC$_2$H$_4$OEt | 3-CF$_3$ |
| CH$_2$OEt | 4-Br | CH$_2$OC$_2$H$_4$OEt | 3-Cl-4-CF$_3$ |
| CH$_2$OEt | 2-I | H | 2,4,6-F$_3$ |
| CH$_2$OEt | 3-I | H | 2,3,5-F$_3$ |
| CH$_2$OEt | 4-I | H | 2,3,4,5-F$_4$ |
| CH$_2$O(Pr-n) | 3-Cl | H | 2,3,4,6-F$_4$ |
| CH$_2$O(Pr-n) | 4-Cl | H | 2,3,5,6-F$_4$ |
| CH$_2$O(Pr-n) | 3-Br | H | 2,3,4-Cl$_3$ |
| CH$_2$O(Pr-n) | 4-Br | H | 2,4,5-Cl$_3$ |
| CH$_2$O(Pr-n) | 3-I | H | 2,3,6-Cl$_3$ |

TABLE 3-continued

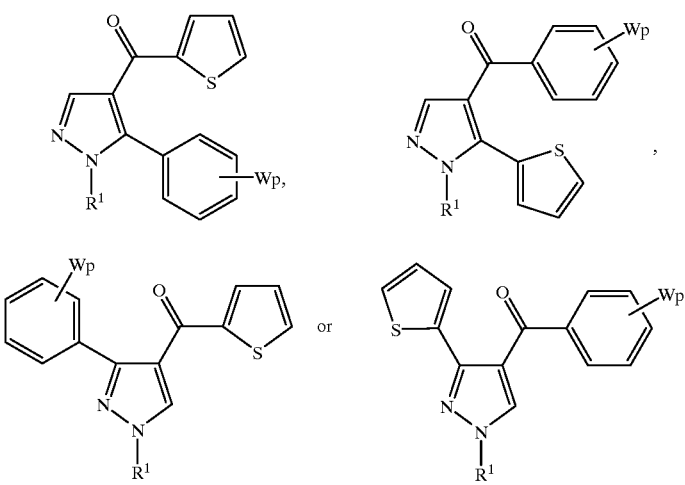

| R¹ | W_P | R¹ | W_P |
|---|---|---|---|
| CH₂O(Pr-n) | 4-I | H | 2,3,4,5-Cl₄ |
| CH₂O(Pr-n) | 3,4-Cl₂ | H | 2,3,4,6-Cl₄ |
| CH₂O(Pr-iso) | 4-Cl | H | 2,3,5,6-Cl₄ |
| H | Cl₅ | H | 4-Br-2-F |
| H | 2,4,6-Br₃ | H | 4-Br-3-F |
| H | 2,3,5-Br₃ | H | 2-F-3-I |
| H | 2,3,4-Br₃ | H | 2-F-4-I |
| H | 3,4,5-Br₃ | H | 2-F-5-I |
| H | 2,4,5-Br₃ | H | 2-F-6-I |
| H | 2,3,6-Br₃ | H | 3-F-2-I |
| H | 2,4-I₂ | H | 3-F-4-I |
| H | 3,4-I₂ | H | 3-F-5-I |
| H | 3,5-I₂ | H | 3-F-6-I |
| H | 2,6-I₂ | H | 4-F-2-I |
| H | 2,3-I₂ | H | 4-F-3-I |
| H | 2,5-I₂ | H | 2-Br-3-Cl |
| H | 2,4,6-I₃ | H | 2-Br-4-Cl |
| H | 2,3,5-I₃ | H | 2-Br-5-Cl |
| H | 2,3,4-I₃ | H | 2-Br-6-Cl |
| H | 3,4,5-I₃ | H | 3-Br-2-Cl |
| H | 2,4,5-I₃ | H | 3-Br-4-Cl |
| H | 2,3,6-I₃ | H | 3-Br-5-Cl |
| H | 2-Cl-3-F | H | 3-Br-6-Cl |
| H | 2-Cl-5-F | H | 4-Br-2-Cl |
| H | 3-Cl-2-F | H | 4-Br-3-Cl |
| H | 3-Cl-5-F | H | 2-Br-3-I |
| H | 3-Cl-6-F | H | 2-Br-4-I |
| H | 2-Br-3-F | H | 2-Br-5-I |
| H | 2-Br-5-F | H | 2-Br-6-I |
| H | 2-Br-6-F | H | 3-Br-2-I |
| H | 3-Br-2-F | H | 3-Br-4-I |
| H | 3-Br-5-F | H | 3-Br-5-I |
| H | 3-Br-6-I | H | 2,3-Cl₂-5-F |
| H | 4-Br-2-I | H | 2,3-Cl₂-4-F |
| H | 4-Br-3-I | H | 2,5-Cl₂-4-F |
| H | 2-Cl-3,4-F₂ | H | 2,6-Cl₂-4-F |
| H | 2-Cl-3,5-F₂ | H | 3,5-Cl₂-4-F |
| H | 2-Cl-3,6-F₂ | H | 2-Br-3,4-F₂ |
| H | 2-Cl-4,5-F₂ | H | 2-Br-3,5-F₂ |
| H | 2-Cl-4,6-F₂ | H | 2-Br-3,6-F₂ |
| H | 2-Cl-5,6-F₂ | H | 2-Br-4,5-F₂ |
| H | 3-Cl-2,4-F₂ | H | 2-Br-4,6-F₂ |
| H | 3-Cl-2,5-F₂ | H | 2-Br-5,6-F₂ |
| H | 2-Cl-2,6-F₂ | H | 3-Br-2,4-F₂ |
| H | 3-Cl-4,5-F₂ | H | 3-Br-2,5-F₂ |
| H | 3-Cl-4,6-F₂ | H | 3-Br-2,6-F₂ |
| H | 3-Cl-5,6-F₂ | H | 3-Br-4,5-F₂ |
| H | 4-Cl-2,3-F₂ | H | 3-Br-4,6-F₂ |
| H | 4-Cl-2,5-F₂ | H | 3-Br-5,6-F₂ |
| H | 4-Cl-2,6-F₂ | H | 4-Br-2,3-F₂ |
| H | 4-Cl-3,5-F₂ | H | 4-Br-2,5-F₂ |
| H | 3,4-Cl₂-2-F | H | 4-Br-2,6-F₂ |
| H | 3,5-Cl₂-2-F | H | 4-Br-3,5-F₂ |

TABLE 3-continued

| R¹ | W_P | R¹ | W_P |
|---|---|---|---|
| H | 2,5-Cl₂-6-F | H | 3,4-Br₂-2-F |
| H | 3,4-Cl₂-6-F | H | 3,5-Br₂-2-F |
| H | 2,4-Cl₂-6-F | H | 2,5-Br₂-6-F |
| H | 2,3-Cl₂-6-F | H | 3,4-Br₂-6-F |
| H | 2,4-Cl₂-3-F | H | 2,4-Br₂-6-F |
| H | 2,5-Cl₂-3-F | H | 2,3-Br₂-6-F |
| H | 2,6-Cl₂-3-F | H | 2,4-Br₂-3-F |
| H | 3,4-Cl₂-5-F | H | 2,5-Br₂-3-F |
| H | 2,6-Br₂-3-F | H | 2-F-5,6-I₂ |
| H | 3,4-Br₂-5-F | H | 3-F-2,4-I₂ |
| H | 2,4-Br₂-5-F | H | 3-F-2,5-I₂ |
| H | 2,3-Br₂-5-F | H | 3-F-2,6-I₂ |
| H | 2,3-Br₂-4-F | H | 5-F-3,4-I₂ |
| H | 2,5-Br₂-4-F | H | 5-F-2,4-I₂ |
| H | 2,6-Br₂-4-F | H | 5-F-2,3-I₂ |
| H | 3,5-Br₂-4-F | H | 4-F-2,3-I₂ |
| H | 3,4-F₂-2-I | H | 4-F-2,5-I₂ |
| H | 3,5-F₂-2-I | H | 4-F-2,6-I₂ |
| H | 2,5-F₂-6-I | H | 4-F-3,5-I₂ |
| H | 3,4-F₂-6-I | H | 2-Br-3,4-Cl₂ |
| H | 2,4-F₂-6-I | H | 2-Br-3,5-Cl₂ |
| H | 2,3-F₂-6-I | H | 2-Br-3,6-Cl₂ |
| H | 2,4-F₂-3-I | H | 2-Br-4,5-Cl₂ |
| H | 2,5-F₂-3-I | H | 6-Br-2,4-Cl₂ |
| H | 2,6-F₂-3-I | H | 6-Br-2,3-Cl₂ |
| H | 3,4-F₂-5-I | H | 3-Br-2,4-Cl₂ |
| H | 2,4-F₂-5-I | H | 3-Br-2,5-Cl₂ |
| H | 2,3-F₂-5-I | H | 3-Br-2,6-Cl₂ |
| H | 2,3-F₂-4-I | H | 3-Br-4,5-Cl₂ |
| H | 2,5-F₂-4-I | H | 5-Br-2,4-Cl₂ |
| H | 2,6-F₂-4-I | H | 5-Br-2,3-Cl₂ |
| H | 3,5-F₂-4-I | H | 4-Br-2,3-Cl₂ |
| H | 2-F-3,4-I₂ | H | 4-Br-2,5-Cl₂ |
| H | 2-F-3,5-I₂ | H | 4-Br-2,6-Cl₂ |
| H | 2-F-3,6-I₂ | H | 4-Br-3,5-Cl₂ |
| H | 2-F-4,5-I₂ | H | 3,4-Br₂-2-Cl |
| H | 2-F-4,6-I₂ | H | 3,5-Br₂-2-Cl |
| H | 2,5-Br₂-6-Cl | H | 3,5-Cl₂-4-I |
| H | 3,4-Br₂-6-Cl | H | 2-Cl-3,4-I₂ |
| H | 2,4-Br₂-6-Cl | H | 2-Cl-3,5-I₂ |
| H | 2,3-Br₂-6-Cl | H | 2-Cl-3,6-I₂ |
| H | 2,4-Br₂-3-Cl | H | 2-Cl-4,5-I₂ |
| H | 2,5-Br₂-3-Cl | H | 2-Cl-4,6-I₂ |
| H | 2,6-Br₂-3-Cl | H | 2-Cl-5,6-I₂ |
| H | 3,4-Br₂-5-Cl | H | 3-Cl-2,4-I₂ |
| H | 2,4-Br₂-5-Cl | H | 3-Cl-2,5-I₂ |
| H | 2,3-Br₂-5-Cl | H | 3-Cl-2,6-I₂ |
| H | 2,3-Br₂-4-Cl | H | 3-Cl-4,5-I₂ |
| H | 2,5-Br₂-4-Cl | H | 3-Cl-4,6-I₂ |
| H | 2,6-Br₂-4-Cl | H | 3-Cl-5,6-I₂ |
| H | 3,5-Br₂-4-Cl | H | 4-Cl-2,3-I₂ |
| H | 3,4-Cl₂-2-I | H | 4-Cl-2,5-I₂ |
| H | 3,5-Cl₂-2-I | H | 4-Cl-2,6-I₂ |

TABLE 3-continued

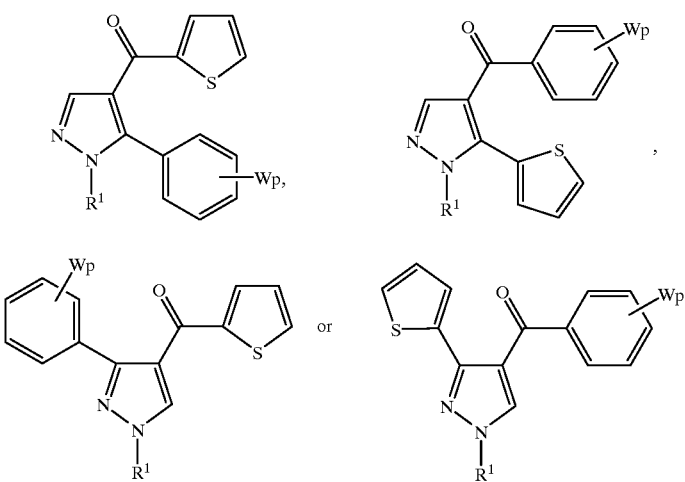

| R¹ | W_P | R¹ | W_P |
|---|---|---|---|
| H | 2,5-Cl$_2$-6-I | H | 4-Cl-3,5-I$_2$ |
| H | 3,4-Cl$_2$-6-I | H | 3,4-Br$_2$-2-I |
| H | 2,4-Cl$_2$-6-I | H | 3,5-Br$_2$-2-I |
| H | 2,3-Cl$_2$-6-I | H | 2,5-Br$_2$-6-I |
| H | 2,4-Cl$_2$-3-I | H | 3,4-Br$_2$-6-I |
| H | 2,5-Cl$_2$-3-I | H | 2,4-Br$_2$-6-I |
| H | 2,6-Cl$_2$-3-I | H | 2,3-Br$_2$-6-I |
| H | 3,4-Cl$_2$-5-I | H | 2,4-Br$_2$-3-I |
| H | 2,4-Cl$_2$-5-I | H | 2,5-Br$_2$-3-I |
| H | 2,3-Cl$_2$-5-I | H | 2,6-Br$_2$-3-I |
| H | 2,3-Cl$_2$-4-I | H | 3,4-Br$_2$-5-I |
| H | 2,5-Cl$_2$-4-I | H | 2,4-Br$_2$-5-I |
| H | 2,6-Cl$_2$-4-I | H | 2,3-Br$_2$-5-I |
| H | 2,3-Br$_2$-4-I | H | 4-Cl-2,3,6-F$_3$ |
| H | 2,5-Br$_2$-4-I | H | 2,3-Cl$_2$-4,5-F$_2$ |
| H | 2,6-Br$_2$-4-I | H | 2,3-Cl$_2$-5,6-F$_2$ |
| H | 3,5-Br$_2$-4-I | H | 2,3-Cl$_2$-4,6-F$_2$ |
| H | 2-Br-3,4-I$_2$ | H | 2,4-Cl$_2$-3,5-F$_2$ |
| H | 2-Br-3,5-I$_2$ | H | 2,4-Cl$_2$-3,6-F$_2$ |
| H | 2-Br-3,6-I$_2$ | H | 4,6-Cl$_2$-2,3-F$_2$ |
| H | 2-Br-4,5-I$_2$ | H | 2,5-Cl$_2$-3,4-F$_2$ |
| H | 2-Br-4,6-I$_2$ | H | 2,5-Cl$_2$-3,6-F$_2$ |
| H | 2-Br-5,6-I$_2$ | H | 3,6-Cl$_2$-2,4-F$_2$ |
| H | 3-Br-2,4-I$_2$ | H | 2,6-Cl$_2$-3,4-F$_2$ |
| H | 3-Br-2,5-I$_2$ | H | 2,6-Cl$_2$-3,5-F$_2$ |
| H | 3-Br-2,6-I$_2$ | H | 3,5-Cl$_2$-2,4-F$_2$ |
| H | 3-Br-4,5-I$_2$ | H | 3,5-Cl$_2$-2,6-F$_2$ |
| H | 3-Br-4,6-I$_2$ | H | 3,4,5-Cl$_3$-2-F |
| H | 3-Br-5,6-I$_2$ | H | 3,4,6-Cl$_3$-2-F |
| H | 4-Br-2,3-I$_2$ | H | 3,5,6-Cl$_3$-2-F |
| H | 4-Br-2,5-I$_2$ | H | 2,3,4-Cl$_3$-6-F |
| H | 4-Br-2,6-I$_2$ | H | 2,4,5-Cl$_3$-3-F |
| H | 4-Br-3,5-I$_2$ | H | 2,4,6-Cl$_3$-3-F |
| H | 2-Cl-3,4,5-F$_3$ | H | 2,5,6-Cl$_3$-3-F |
| H | 2-Cl-3,4,6-F$_3$ | H | 2,3,4-Cl$_3$-5-F |
| H | 2-Cl-3,5,6-F$_3$ | H | 2,3,5-Cl$_3$-4-F |
| H | 6-Cl-2,3,4-F$_3$ | H | 2,3,6-Cl$_3$-4-F |
| H | 3-Cl-2,4,5-F$_3$ | H | 2-Br-3,4,5-F$_3$ |
| H | 3-Cl-2,4,6-F$_3$ | H | 2-Br-3,4,6-F$_3$ |
| H | 5-Cl-2,3,6-F$_3$ | H | 2-Br-3,5,6-F$_3$ |
| H | 5-Cl-2,3,4-F$_3$ | H | 6-Br-2,3,4-F$_3$ |
| H | 4-Cl-2,3,5-F$_3$ | H | 3-Br-2,4,5-F$_3$ |
| H | 3-Br-2,4,6-F$_3$ | H | 3,5,6-F$_3$-2-I |
| H | 5-Br-2,3,6-F$_3$ | H | 2,3,4-F$_3$-6-I |
| H | 5-Br-2,3,4-F$_3$ | H | 2,4,5-F$_3$-3-I |
| H | 4-Br-2,3,5-F$_3$ | H | 2,4,6-F$_3$-3-I |
| H | 4-Br-2,3,6-F$_3$ | H | 2,5,6-F$_3$-3-I |
| H | 2,3-Br$_2$-4,5-F$_2$ | H | 2,3,4-F$_3$-5-I |
| H | 2,3-Br$_2$-5,6-F$_2$ | H | 2,3,5-F$_3$-4-I |
| H | 2,3-Br$_2$-4,6-F$_2$ | H | 2,3,6-F$_3$-4-I |
| H | 2,4-Br$_2$-3,5-F$_2$ | H | 2,3-F$_2$-4,5-I$_2$ |
| H | 2,4-Br$_2$-3,6-F$_2$ | H | 2,3-F$_2$-5,6-I$_2$ |
| H | 4,6-Br$_2$-2,3-F$_2$ | H | 2,3-F$_2$-4,6-I$_2$ |

TABLE 3-continued

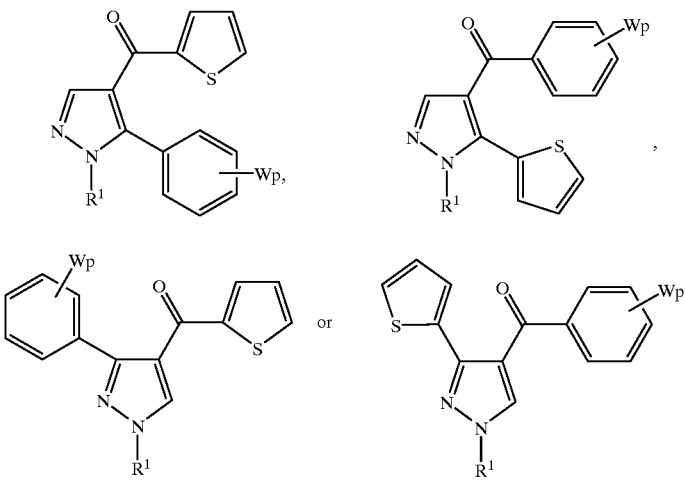

| R[1] | W$_P$ | R[1] | W$_P$ |
|---|---|---|---|
| H | 2,5-Br$_2$-3,4-F$_2$ | H | 2,4-F$_2$-3,5-I$_2$ |
| H | 2,5-Br$_2$-3,6-F$_2$ | H | 2,4-F$_2$-3,6-I$_2$ |
| H | 3,6-Br$_2$-2,4-F$_2$ | H | 4,6-F$_2$-2,3-I$_2$ |
| H | 2,6-Br$_2$-3,4-F$_2$ | H | 2,5-F$_2$-3,4-I$_2$ |
| H | 2,6-Br$_2$-3,5-F$_2$ | H | 2,5-F$_2$-3,6-I$_2$ |
| H | 3,5-Br$_2$-2,4-F$_2$ | H | 3,6-F$_2$-2,4-I$_2$ |
| H | 3,5-Br$_2$-2,6-F$_2$ | H | 2,6-F$_2$-3,4-I$_2$ |
| H | 3,4,6-Br$_3$-2-F | H | 2,6-F$_2$-3,5-I$_2$ |
| H | 3,5,6-Br$_3$-2-F | H | 3,5-F$_2$-2,4-I$_2$ |
| H | 2,3,4-Br$_3$-6-F | H | 3,5-F$_2$-2,6-I$_2$ |
| H | 2,4,5-Br$_3$-3-F | H | 2-F-3,4,5-I$_3$ |
| H | 2,4,6-Br$_3$-3-F | H | 2-F-3,5,6-I$_3$ |
| H | 2,5,6-Br$_3$-3-F | H | 6-F-2,3,4-I$_3$ |
| H | 2,3,4-Br$_3$-5-F | H | 3-F-2,4,5-I$_3$ |
| H | 2,3,5-Br$_3$-4-F | H | 3-F-2,4,6-I$_3$ |
| H | 2,3,6-Br$_3$-4-F | H | 5-F-2,3,6-I$_3$ |
| H | 3,4,5-F$_2$-2-I | H | 5-F-2,3,4-I$_3$ |
| H | 3,4,6-F$_3$-2-I | H | 4-F-2,3,5-I$_3$ |
| H | 4-F-2,3,6-I$_3$ | H | 2,4,6-Br$_3$-3-Cl |
| H | 2-Br-3,4,5-Cl$_3$ | H | 2,5,6-Br$_3$-3-Cl |
| H | 2-Br-3,4,6-Cl$_3$ | H | 2,3,4-Br$_3$-5-Cl |
| H | 2-Br-3,5,6-Cl$_3$ | H | 2,3,5-Br$_3$-4-Cl |
| H | 6-Br-2,3,4-Cl$_3$ | H | 2,3,6-Br$_3$-4-Cl |
| H | 3-Br-2,4,5-Cl$_3$ | H | 3,4,5-Cl$_3$-2-I |
| H | 3-Br-2,4,6-Cl$_3$ | H | 3,4,6-Cl$_3$-2-I |
| H | 5-Br-2,3,6-Cl$_3$ | H | 3,5,6-Cl$_3$-2-I |
| H | 5-Br-2,3,4-Cl$_3$ | H | 2,3,4-Cl$_3$-6-I |
| H | 4-Br-2,3,5-Cl$_3$ | H | 2,4,5-Cl$_3$-3-I |
| H | 4-Br-2,3,6-Cl$_3$ | H | 2,4,6-Cl$_3$-3-I |
| H | 2,3-Br$_2$-4,5-Cl$_2$ | H | 2,5,6-Cl$_3$-3-I |
| H | 2,3-Br$_2$-5,6-Cl$_2$ | H | 2,3,4-Cl$_3$-5-I |
| H | 2,3-Br$_2$-4,6-Cl$_2$ | H | 2,3,5-Cl$_3$-4-I |
| H | 2,4-Br$_2$-3,5-Cl$_2$ | H | 2,3,6-Cl$_3$-4-I |
| H | 2,4-Br$_2$-3,6-Cl$_2$ | H | 2,3-Cl$_2$-4,5-I$_2$ |
| H | 4,6-Br$_2$-2,3-Cl$_2$ | H | 2,3-Cl$_2$-5,6-I$_2$ |
| H | 2,5-Br$_2$-3,4-Cl$_2$ | H | 2,3-Cl$_2$-4,6-I$_2$ |
| H | 2,5-Br$_2$-3,6-Cl$_2$ | H | 2,4-Cl$_2$-3,5-I$_2$ |
| H | 3,6-Br$_2$-2,4-Cl$_2$ | H | 2,4-Cl$_2$-3,6-I$_2$ |
| H | 2,6-Br$_2$-3,4-Cl$_2$ | H | 4,6-Cl$_2$-2,3-I$_2$ |
| H | 2,6-Br$_2$-3,5-Cl$_2$ | H | 2,5-Cl$_2$-3,4-I$_2$ |
| H | 3,5-Br$_2$-2,4-Cl$_2$ | H | 2,5-Cl$_2$-3,6-I$_2$ |
| H | 3,5-Br$_2$-2,6-Cl$_2$ | H | 3,6-Cl$_2$-2,4-I$_2$ |
| H | 3,4,5-Br$_3$-2-Cl | H | 2,6-Cl$_2$-3,4-I$_2$ |
| H | 3,4,6-Br$_3$-2-Cl | H | 2,6-Cl$_2$-3,5-I$_2$ |
| H | 3,5,6-Br$_3$-2-Cl | H | 3,5-Cl$_2$-2,4-I$_2$ |
| H | 2,3,4-Br$_3$-6-Cl | H | 3,5-Cl$_2$-2,6-I$_2$ |
| H | 2,4,5-Br$_3$-3-Cl | H | 3,4,5-Br$_3$-2-I |
| H | 3,4,6-Br$_3$-2-I | H | 2,3-Cl$_2$-4,5,6-F$_3$ |
| H | 3,5,6-Br$_3$-2-I | H | 2,5-Cl$_2$-3,4,6-F$_3$ |
| H | 2,3,4-Br$_3$-6-I | H | 2,4,6-Cl$_3$-3,5-F$_2$ |
| H | 2,4,5-Br$_3$-3-I | H | 2,3,5-Cl$_3$-4,6-F$_2$ |
| H | 2,4,6-Br$_3$-3-I | H | 2,3,4-Cl$_3$-5,6-F$_2$ |
| H | 2,5,6-Br$_3$-3-I | H | 3,4,5-Cl$_3$-2,6-F$_2$ |

TABLE 3-continued

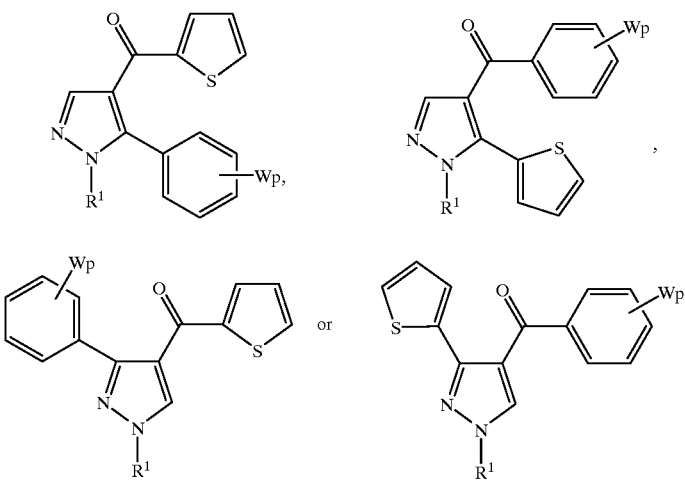

| R¹ | W$_P$ | R¹ | W$_P$ |
|---|---|---|---|
| H | 2,3,4-Br$_3$-5-I | H | 2,4,5-Cl$_3$-3,6-F$_2$ |
| H | 2,3,5-Br$_3$-4-I | H | 2,3,6-Cl$_3$-4,5-F$_2$ |
| H | 2,3,6-Br$_3$-4-I | H | 2,3,4,5-Cl$_4$-6-F |
| H | 2,3-Br$_2$-4,5-I$_2$ | H | 2,3,4,6-Cl$_4$-5-F |
| H | 2,3-Br$_2$-5,6-I$_2$ | H | 2,3,5,6-Cl$_4$-4-F |
| H | 2,3-Br$_2$-4,6-I$_2$ | H | 2-Br-3,4,5,6-F$_4$ |
| H | 2,4-Br$_2$-3,5-I$_2$ | H | 3-Br-2,4,5,6-F$_4$ |
| H | 2,4-Br$_2$-3,6-I$_2$ | H | 4-Br-2,3,5,6-F$_4$ |
| H | 4,6-Br$_2$-2,3-I$_2$ | H | 2,4-Br$_2$-3,5,6-F$_3$ |
| H | 2,5-Br$_2$-3,4-I$_2$ | H | 3,4-Br$_2$-2,5,6-F$_3$ |
| H | 2,5-Br$_2$-3,6-I$_2$ | H | 3,5-Br$_2$-2,4,6-F$_3$ |
| H | 3,6-Br$_2$-2,4-I$_2$ | H | 2,6-Br$_2$-3,4,5-F$_3$ |
| H | 2,6-Br$_2$-3,4-I$_2$ | H | 2,3-Br$_2$-4,5,6-F$_3$ |
| H | 2,6-Br$_2$-3,5-I$_2$ | H | 2,5-Br$_2$-3,4,6-F$_3$ |
| H | 3,5-Br$_2$-2,4-I$_2$ | H | 2,4,6-Br$_3$-3,5-F$_2$ |
| H | 3,5-Br$_2$-2,6-I$_2$ | H | 2,3,5-Br$_3$-4,6-F$_2$ |
| H | 2-Cl-3,4,5,6-F$_4$ | H | 2,3,4-Br$_3$-5,6-F$_2$ |
| H | 3-Cl-2,4,5,6-F$_4$ | H | 3,4,5-Br$_3$-2,6-F$_2$ |
| H | 4-Cl-2,3,5,6-F$_4$ | H | 2,4,5-Br$_3$-3,6-F$_2$ |
| H | 2,4-Cl$_2$-3,5,6-F$_3$ | H | 2,3,6-Br$_3$-4,5-F$_2$ |
| H | 3,4-Cl$_2$-2,5,6-F$_3$ | H | 2,3,4,5-Br$_4$-6-F |
| H | 3,5-Cl$_2$-2,4,6-F$_3$ | H | 2,3,4,6-Br$_4$-5-F |
| H | 2,6-Cl$_2$-3,4,5-F$_3$ | H | 2,3,5,6-Br$_4$-4-F |
| H | 3,4-Br$_2$-2,5,6-Cl$_3$ | H | 2,5-(CF$_3$)$_2$ |
| H | 2-I-3,4,5,6-F$_4$ | H | 4-F-3,5-(CF$_3$)$_2$ |
| H | 3-I-2,4,5,6-F$_4$ | H | 4-Cl-3,5-(CF$_3$)$_2$ |
| H | 4-I-2,3,5,6-F$_4$ | H | 4-Br-3,5-(CF$_3$)$_2$ |
| H | 2-Br-3,4,5,6-Cl$_4$ | H | 3-OCH$_2$F |
| H | 3-Br-2,4,5,6-Cl$_4$ | H | 4-OCH$_2$F |
| H | 4-Br-2,3,5,6-Cl$_4$ | H | 2-Me$_2$N |
| H | 2,4-Br$_2$-3,5,6-Cl$_3$ | H | 4-Me$_2$N |
| H | 3-Br-4-Me | H | 3,5-(Me$_2$N)$_2$ |
| H | 4-F-3,5-Me$_2$ | H | 4-F-3,5-(Me$_2$N)$_2$ |
| H | 4-Cl-3,5-Me$_2$ | H | 4-Cl-3,5-(Me$_2$N)$_2$ |
| H | 4-Br-3,5-Me$_2$ | H | 4-Br-3,5-(Me$_2$N)$_2$ |
| H | 2-MeO | H | 2-NO$_2$ |
| H | 4-F-3-MeO | H | 3,5-(NO$_2$)$_2$ |
| H | 3-F-4-MeO | H | 4-F-3,5-(NO$_2$)$_2$ |
| H | 4-Cl-3-MeO | H | 4-Br-3,5-(NO$_2$)$_2$ |
| H | 3-Cl-4-MeO | H | 4-F-3-CN |
| H | 4-Br-3-MeO | H | 3-CN |
| H | 3-Br-4-MeO | H | 3,5-(CN)$_2$ |
| H | 4-F-3,5-(MeO)$_2$ | H | 4-F-3,5-(CN)$_2$ |
| H | 4-Cl-3,5-(MeO)$_2$ | H | 4-Cl-3,5-(CN)$_2$ |
| H | 4-Br-3,5-(MeO)$_2$ | H | 4-Br-3,5-(CN)$_2$ |
| H | 2-CF$_3$ | H | 2-CO$_2$Me |
| H | 3-F-5-CF$_3$ | H | 3-CO$_2$Me |
| H | 3-Cl-4-CF$_3$ | H | 4-CO$_2$Me |
| H | 2,4-(CF$_3$)$_2$ | H | 4-F-3-CO$_2$Me |
| H | 3,5-(CF$_3$)$_2$ | H | 4-Cl-3-CO$_2$Me |
| H | 2,6-(CF$_3$)$_2$ | H | 4-F-3,5-(CO$_2$Me)$_2$ |
| H | 2,3-(CF$_3$)$_2$ | H | 4-Cl-3,5-(CO$_2$Me)$_2$ |
| H | 2-Ph | H | 4-F-3,5-(PhO)$_2$ |

TABLE 3-continued

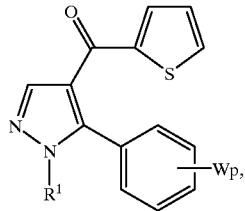

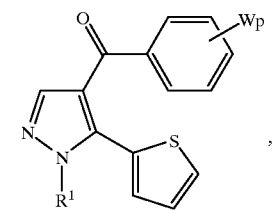

| R¹ | W_P | R¹ | W_P |
|---|---|---|---|
| H | 3-Ph | H | 4-Cl-3,5-(PhO)₂ |
| H | 4-PH | H | 4-Br-3,5-(PhO)₂ |
| H | 2,4-Ph₂ | CH₂OMe | 3,4-Cl₂ |
| H | 3,5-Ph₂ | CH₂OMe | 3-Cl-4-F |
| H | 2,6-Ph₂ | CH₂OMe | 3-CF₃ |
| H | 2,3-Ph₂ | CH₂OMe | 3,5-Cl₂ |
| H | 2,5-Ph₂ | CH₂OMe | 3-Cl-4-F |
| H | 4-F-3-Ph | CH₂OMe | 3,4,5-Cl₃ |
| H | 3-F-4-Ph | CH₂OMe | 3,5-Cl₂-4-Br |
| H | 4-Cl-3-Ph | CH₂OMe | 3,5-Cl₂-4-I |
| H | 3-Cl-4-Ph | CH₂OMe | 3,5-(CF₃)₂ |
| H | 4-Br-3-Ph | CH₂OMe | 3,5-F₂ |
| H | 3-Br-4-Ph | CH₂OMe | 3,5-Cl₂-4-F |
| H | 4-F-3,5-Ph₂ | CH₂OMe | 3,5-Br₂-4-Cl |
| H | 4-Cl-3,5-Ph₂ | CH₂OMe | 3,4,5-F₃ |
| H | 4-Br-3,5-Ph₂ | CH₂OMe | 3,4-F₂ |
| H | 2-PhO | CH₂OMe | 3,5-Br₂ |
| H | 2,4-(PhO)₂ | CH₂OMe | 3,5-Br₂-4-F |
| H | 3,5-(PhO)₂ | CH₂OMe | 3-Br-5-I |
| H | 2,6-(PhO)₂ | CH₂OMe | 3,4-Cl₂ |
| H | 2,3-(PhO)₂ | CH₂OMe | 3-Cl-4-F |
| H | 2,5-(PhO)₂ | CH₂OMe | 3-CF₃ |
| H | 4-F-3-PhO | CH₂OEt | 3,5-Cl₂ |
| H | 3-F-4-PhO | CH₂OEt | 3-Cl-4-F |
| H | 4-Cl-3-PhO | CH₂OEt | 3,4,5-Cl₃ |
| H | 3-Cl-4-PhO | CH₂OEt | 3,5-Cl₂-4-Br |
| H | 4-Br-3-PhO | CH₂OEt | 3,5-Cl₂-4-I |
| H | 3-Br-4-PhO | CH₂OEt | 3,5-(CF₃)₂ |
| CH₂OEt | 3,5-F₂ | CH₂OC₂H₄OMe | 3,5-Cl₂ |
| CH₂OEt | 3,5-Cl₂-4-F | CH₂OC₂H₄OMe | 3,4,5-Cl₃ |
| CH₂OEt | 3,5-Br₂-4-Cl | CH₂OC₂H₄OMe | 3,5-F₂ |
| CH₂OEt | 3,4,5-F₃ | CH₂OC₂H₄OMe | 3,5-Cl₂-4-F |
| CH₂OEt | 3,4-F₂ | CH₂OC₂H₄OMe | 3,4-Cl₂ |
| CH₂OEt | 3,5-Br₂ | CH₂OC₂H₄OMe | 3,5-Br₂ |
| CH₂OEt | 3,5-Br₂-4-F | CH₂OC₂H₄OMe | 3,5-Br₂-4-F |
| CH₂OEt | 3-Br-5-I | CH₂OC₂H₄OEt | 3,5-Cl₂ |
| CH₂O(Pr-n) | 3,5-Cl₂ | CH₂OC₂H₄OEt | 3,4,5-Cl₃ |
| CH₂O(Pr-n) | 3-Cl-4-F | CH₂OC₂H₄OEt | 3,5-F₂ |
| CH₂O(Pr-n) | 3,4,5-Cl₃ | CH₂OC₂H₄OEt | 3,5-Cl₂-4-F |
| CH₂O(Pr-n) | 3,5-Cl₂-4-Br | CH₂OC₂H₄OEt | 3,4-Cl₂ |
| CH₂OP(r-n) | 3,5-Cl₂-4-I | CH₂OC₂H₄OEt | 3,5-Br₂ |
| CH₂O(Pr-n) | 3,5-(CF₃)₂ | CH₂OC₂H₄OEt | 3,5-Br₂-4-F |
| CH₂O(Pr-n) | 3,5-F₂ | CH₂O(Bu-n) | 3,5-Cl₂ |
| CH₂O(Pr-n) | 3,5-Cl₂-4-F | CH₂O(Bu-iso) | 3,5-Cl₂ |
| CH₂O(Pr-n) | 3,5-Br₂-4-Cl | CH₂O(Bu-sec) | 3,5-Cl₂ |
| CH₂O(Pr-n) | 3,4,5-F₃ | CH₂O(Bu-tert) | 3,5-Cl₂ |
| CH₂O(Pr-n) | 3,4-F₂ | CH₂OCH₂CH₂O(Pr-n) | 3,5-Cl₂ |
| CH₂O(Pr-n) | 3,5-Br₂ | CH₂OCH₂CH₂O(Pr-iso) | 3,5-Cl₂ |
| CH₂O(Pr-n) | 3,5-Br₂-4-F | MeCO | 3,5-Cl₂ |
| CH₂O(Pr-n) | 3-Br-5-I | MeCO | 3,4-Cl₂ |
| CH₂O(Pr-iso) | 3,5-Cl₂ | MeCO | 3,4,5-Cl₃ |
| CH₂O(Pr-iso) | 3,4,5-Cl₃ | MeCO | 3,5-F₂ |
| CH₂O(Pr-iso) | 3,5-F₂ | MeCO | 3,5-Cl₂-4-F |

TABLE 3-continued

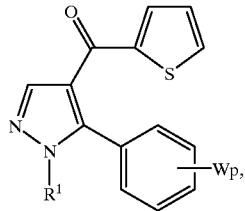

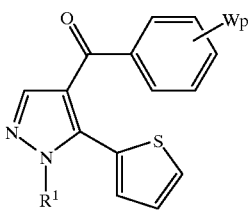
or

| $R^1$ | $W_P$ | $R^1$ | $W_P$ |
|---|---|---|---|
| CH$_2$O(Pr-iso) | 3,5-Cl$_2$-4-F | MeCO | 3,5-Br$_2$ |
| CH$_2$O(Pr-iso) | 3,4-Cl$_2$ | MeCO | 3,5-Br$_2$-4-F |
| CH$_2$O(Pr-iso) | 3,5-Br$_2$ | MeCO | 4-Br |
| CH$_2$O(Pr-iso) | 3,5-Br$_2$-4-F | EtCO | 3,5-Cl$_2$ |
| EtCO | 3,4-Cl$_2$ | MeSO$_2$ | 3,5-Cl$_2$-4-F |
| EtCO | 3,4,5-Cl$_3$ | MeSO$_2$ | 3,5-Br$_2$ |
| EtCO | 3,5-F$_2$ | MeSO$_2$ | 3,5-Br$_2$-4-F |
| EtCO | 3,5-Cl$_2$-4-F | MeSO$_2$ | 3-Cl-4-MeO |
| EtCO | 3,5-Br$_2$ | EtSO$_2$ | 3,5-Cl$_2$ |
| EtCO | 3,5-Br$_2$-4-F | (Pr-n)SO$_2$ | 3,5-Cl$_2$ |
| (Pr-n)CO | 3,5-Cl$_2$ | (Bu-n)SO$_2$ | 3,5-Cl$_2$ |
| (Bu-n)CO | 3,5-Cl$_2$ | Me$_2$NSO$_2$ | 3,5-Cl$_2$ |
| PhCO | 3,5-Cl$_2$ | Me$_2$NSO$_2$ | 3,4-Cl$_2$ |
| PhCO | 3,4-Cl$_2$ | Me$_2$NSO$_2$ | 3,4,5-Cl$_3$ |
| PhCO | 3,4,5-Cl$_3$ | Me$_2$NSO$_2$ | 3,5-F$_2$ |
| PhCO | 3,5-F$_2$ | Me$_2$NSO$_2$ | 3,5-Cl$_2$-4-F |
| PhCO | 3,5-Cl$_2$-4-F | Me$_2$NSO$_2$ | 3,5-Br$_2$ |
| PhCO | 3,5-Br$_2$ | Me$_2$NSO$_2$ | 3,5-Br$_2$-4-F |
| PhCO | 3,5-Br$_2$-4-F | Me$_2$NSO$_2$ | 3-Cl-4-MeO |
| MeOCO | 3,5-Cl$_2$ | Et$_2$NSO$_2$ | 3,5-Cl$_2$ |
| MeOCO | 3,4-Cl$_2$ | (Pr-n)$_2$NSO$_2$ | 3,5-Cl$_2$ |
| MeOCO | 3,4,5-Cl$_3$ | (Bu-n)$_2$NSO$_2$ | 3,5-Cl$_2$ |
| MeOCO | 3,5-F$_2$ | Me$_2$NCO | 3,5-Cl$_2$ |
| MeOCO | 3,5-Cl$_2$-4-F | Me$_2$NCO | 3,4-Cl$_2$ |
| MeOCO | 3,5-Br$_2$ | Me$_2$NCO | 3,4,5-Cl$_3$ |
| MeOCO | 3,5-Br$_2$-4-F | Me$_2$NCO | 3,5-F$_2$ |
| EtOCO | 3,5-Cl$_2$ | Me$_2$NCO | 3,5-Cl$_2$-4-F |
| (Pr-n)OCO | 3,5-Cl$_2$ | Me$_2$NCO | 3,5-Br$_2$ |
| (Bu-n)OCO | 3,5-Cl$_2$ | Me$_2$NCO | 3,5-Br$_2$-4-F |
| MeSO$_2$ | 3,5-Cl$_2$ | Et$_2$NCO | 3,5-Cl$_2$ |
| MeSO$_2$ | 3,4-Cl$_2$ | Et$_2$NCO | 4-F |
| MeSO$_2$ | 3,4,5-Cl$_3$ | (Pr-n)$_2$NCO | 3,5-Cl$_2$ |
| MeSO$_2$ | 3,5-F$_2$ | (Bu-n)$_2$NCO | 3,5-Cl$_2$ |
| MeNHCO | 3,5-Cl$_2$ | | |
| MeNHCO | 3,4-Cl$_2$ | | |
| MeNHCO | 3,4,5-Cl$_3$ | | |
| MeNHCO | 3,5-F$_2$ | | |
| MeNHCO | 3,5-Cl$_2$-4-F | | |
| MeNHCO | 3,5-Br$_2$ | | |
| MeNHCO | 3,5-Br$_2$-4-F | | |
| EtNHCO | 3,5-Cl$_2$ | | |
| (Pr-n)NHCO | 3,5-Cl$_2$ | | |
| (Bu-n)NHCO | 3,5-Cl$_2$ | | |

TABLE 4

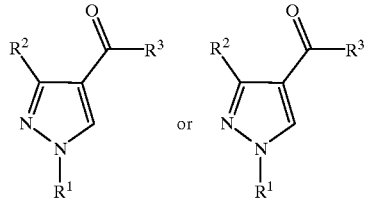

| R¹ | R² | R³ |
|---|---|---|
| H | 1-naphthyl | Ph |
| H | 2-naphthyl | Ph |
| H | thiophen-3-yl | Ph |
| H | 5-chlorothiophen-2-yl | Ph |
| H | furan-2-yl | Ph |
| H | furan-3-yl | Ph |
| H | pyrrol-1-yl | Ph |
| H | pyrrol-2-yl | Ph |
| H | pyrrol-3-yl | Ph |
| H | oxazol-2-yl | Ph |
| H | oxazol-4-yl | Ph |
| H | oxazol-5-yl | Ph |
| H | thizaol-2-yl | Ph |
| H | thiazol-4-yl | Ph |
| H | thiazol-5-yl | Ph |
| H | imidazol-1-yl | Ph |
| H | imidazol-2-yl | Ph |
| H | imidazol-4-yl | Ph |
| H | imidazol-5-yl | Ph |
| H | isoxazol-3-yl | Ph |
| H | isoxazol-4-yl | Ph |
| H | isoxazol-5-yl | Ph |
| H | isothiazol-3-yl | Ph |
| H | isothiazol-4-yl | Ph |
| H | isothiazol-5-yl | Ph |
| H | pyrazol-1-yl | Ph |
| H | pyrazol-3-yl | Ph |
| H | pyrazol-4-yl | Ph |
| H | pyrazol-5-yl | Ph |
| H | 1,3,4-oxadiazol-2-yl | Ph |
| H | 1,3,4-thiadiazol-2-yl | Ph |
| H | 1,3,4-triazol-1-yl | Ph |
| H | 1,3,4-triazol-2-yl | Ph |
| H | 1,2,4-oxadiazol-3-yl | Ph |
| H | 1,2,4-oxadiazol-5-yl | Ph |
| H | 1,2,4-thiadiazol | Ph |
| H | 1,2,4-thiadiazol-5-yl | Ph |
| H | 1,2,4-triazol-1-yl | Ph |
| H | 1,2,4-triazol-3-yl | Ph |
| H | 1,2,4-triazol-5-yl | Ph |
| H | 1,2,3-oxadiazol-4-yl | Ph |
| H | 1,2,3-oxadiazol-5-yl | Ph |
| H | 1,2,3-thiadiazol-3-yl | Ph |
| H | 1,2,3-thiadiazol-5-yl | Ph |
| H | 1,2,3,4-tetrazol-1-yl | Ph |
| H | 1,2,3,4-tetrazol-5-yl | Ph |
| H | 1,2,3,5-tetrazol-1-yl | Ph |
| H | 1,2,3,5-tetrazol-4-yl | Ph |
| H | pyridin-2-yl | Ph |
| H | pyridin-3-yl | Ph |
| H | pyridin-4-yl | Ph |
| H | pyrimidin-2-yl | Ph |
| H | pyrimidin-5-yl | Ph |
| H | pyrimidin-4-yl | Ph |
| H | pyrazin-2-yl | Ph |
| H | pyridazin-3-yl | Ph |
| H | pyridazin-4-yl | Ph |
| H | 1,3,5-triazin-2-yl | Ph |
| H | 1,2,4-triazin-3-yl | Ph |
| H | 1,2,4-triazin-5-yl | Ph |
| H | 1,2,4-triazin-6-yl | Ph |
| H | benzothiophen-2-yl | Ph |
| H | benzothiophen-3-yl | Ph |
| H | benzothiophen-4-yl | Ph |
| H | benzothiophen-5-yl | Ph |
| H | benzothiophen-6-yl | Ph |

TABLE 4-continued

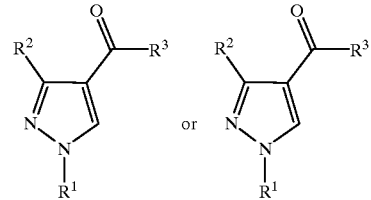

| R¹ | R² | R³ |
|---|---|---|
| H | benzothiophen-7-yl | Ph |
| H | benzofuran-2-yl | Ph |
| H | benzofuran-3-yl | Ph |
| H | benzofuran-4-yl | Ph |
| H | benzofuran-5-yl | Ph |
| H | benzofuran-6-yl | Ph |
| H | benzofuran-7-yl | Ph |
| H | indol-1-yl | Ph |
| H | indol-2-yl | Ph |
| H | indol-3-yl | Ph |
| H | indol-4-yl | Ph |
| H | indol-5-yl | Ph |
| H | indol-6-yl | Ph |
| H | indol-7-yl | Ph |
| H | benzoxazol-2-yl | Ph |
| H | benzoxazol-4-yl | Ph |
| H | benzoxazol-5-yl | Ph |
| H | benzoxazol-6-yl | Ph |
| H | benzoxazol-7-yl | Ph |
| H | benzothiazol-2-yl | Ph |
| H | benzothiazol-4-yl | Ph |
| H | benzothiazol-5-yl | Ph |
| H | benzothiazol-6-yl | Ph |
| H | benzothiazol-7-yl | Ph |
| H | benzimidazol-1-yl | Ph |
| H | benzimidazol-2-yl | Ph |
| H | benzimidazol-4-yl | Ph |
| H | benzimidazol-5-yl | Ph |
| H | benzimidazol-6-yl | Ph |
| H | benzimidazol-7-yl | Ph |
| H | benzisoxazol-3-yl | Ph |
| H | benzisoxazol-4-yl | Ph |
| H | benzisoxazol-5-yl | Ph |
| H | benzisoxazol-6-yl | Ph |
| H | benzisoxazol-7-yl | Ph |
| H | benzisothiazol-3-yl | Ph |
| H | benzisothiazol-4-yl | Ph |
| H | benzisothiazol-5-yl | Ph |
| H | benzisothiazol-6-yl | Ph |
| H | benzisothiazol-7-yl | Ph |
| H | indazol-1-yl | Ph |
| H | indazol-3-yl | Ph |
| H | indazol-4-yl | Ph |
| H | indazol-5-yl | Ph |
| H | indazol-6-yl | Ph |
| H | indazol-7-yl | Ph |
| H | quinolin-2-yl | Ph |
| H | quinolin-3-yl | Ph |
| H | quinolin-4-yl | Ph |
| H | quinolin-5-yl | Ph |
| H | quinolin-6-yl | Ph |
| H | quinolin-7-yl | Ph |
| H | quinolin-8-yl | Ph |
| H | isoquinolin-1-yl | Ph |
| H | isoquinolin-3-yl | Ph |
| H | isoquinolin-4-yl | Ph |
| H | isoquinolin-5-yl | Ph |
| H | isoquinolin-6-yl | Ph |
| H | isoquinolin-7-yl | Ph |
| H | isoquinolin-8-yl | Ph |
| H | quinazolin-2-yl | Ph |
| H | quinazolin-4-yl | Ph |
| H | quinazolin-5-yl | Ph |
| H | quinazolin-6-yl | Ph |
| H | quinazolin-7-yl | Ph |
| H | quinozolin-8-yl | Ph |

TABLE 4-continued

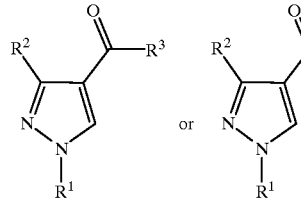

| R¹ | R² | R³ |
|---|---|---|
| H | quinoxalin-2-yl | Ph |
| H | quinoxalin-5-yl | Ph |
| H | quinoxalin-6-yl | Ph |
| H | phthalazin-1-yl | Ph |
| H | phthalazin-5-yl | Ph |
| H | phthalazin-6-yl | Ph |
| H | cinnolin-3-yl | Ph |
| H | cinnolin-4-yl | Ph |
| H | cinnolin-5-yl | Ph |
| H | cinnolin-6-yl | Ph |
| H | cinnolin-7-yl | Ph |
| H | cinnolin-8-yl | Ph |
| H | 1,2,4-benzotriazin-3-yl | Ph |
| H | 1,2,4-benzotriazin-5-yl | Ph |
| H | 1,2,4-benzotriazin-6-yl | Ph |
| H | 1,2,4-benzotriazin-7-yl | Ph |
| H | 1,2,4-benzotriazin-8-yl | Ph |
| H | 1-naphthyl | thiophen-2-yl |
| H | thiophen-2-yl | 1-naphthyl |
| H | 2-naphthyl | thiophen-2-yl |
| H | 2-naphthyl | furan-2-yl |
| H | furan-2-yl | 2-naphthyl |
| H | thiophen-2-yl | thiophen-2-yl |
| H | thiophen-3-yl | thiophen-2-yl |
| H | 5-chlorothiophen-2-yl | thiophen-2-yl |
| H | thiophen-2-yl | 5-chlorothiophen-2-yl |
| H | 5-chlorothiophen-2-yl | 5-chlorothiophen-2-yl |
| H | furan-2-yl | thiophen-2-yl |
| H | 3,4-Cl²—Ph | furan-2-yl |
| H | furan-3-yl | thiophen-2-yl |
| H | pyrrol-1-yl | thiophen-2-yl |
| H | pyrrol-2-yl | thiophen-2-yl |
| H | pyrrol-3-yl | thiophen-2-yl |
| H | oxazol-2-yl | thiophen-2-yl |
| H | oxazol-4-yl | thiophen-2-yl |
| H | oxazol-5-yl | thiophen-2-yl |
| H | thiazol-2-yl | thiophen-2-yl |
| H | thiazol-4-yl | thiophen-2-yl |
| H | thiazol-5-yl | thiophen-2-yl |
| H | imidazol-1-yl | thiophen-2-yl |
| H | imidazol-2-yl | thiophen-2-yl |
| H | imidazol-4-yl | thiophen-2-yl |
| H | imidazol-5-yl | thiophen-2-yl |
| H | isoxazol-3-yl | thiophen-2-yl |
| H | isoxazol-4-yl | thiophen-2-yl |
| H | isoxazol-5-yl | thiophen-2-yl |
| H | isothiazol-3-yl | thiophen-2-yl |
| H | isothiazol-4-yl | thiophen-2-yl |
| H | isothiazol-5-yl | thiophen-2-yl |
| H | pyrazol-1-yl | thiophen-2-yl |
| H | pyrazol-3-yl | thiophen-2-yl |
| H | pyrazol-4-yl | thiophen-2-yl |
| H | pyrazol-5-yl | thiophen-2-yl |
| H | 1,3,4-oxadiazol-2-yl | thiophen-2-yl |
| H | 1,3,4-thiadiazol-2-yl | thiophen-2-yl |
| H | 1,3,4-triazol-1-yl | thiophen-2-yl |
| H | 1,3,4-triazol-2-yl | thiophen-2-yl |
| H | 1,2,4-oxadiazol-3-yl | thiophen-2-yl |
| H | 1,2,4-oxadiazol-5-yl | thiophen-2-yl |
| H | 1,2,4,-thiadiazol-3-yl | thiophen-2-yl |
| H | 1,2,4-thiadiazol-5-yl | thiophen-2-yl |
| H | 1,2,4-triazol-1-yl | thiophen-2-yl |
| H | 1,2,4-triazol-3-yl | thiophen-2-yl |
| H | 1,2,4-triazol-5-yl | thiophen-2-yl |
| H | 1,2,3-oxadiazol-4-yl | thiophen-2-yl |
| H | 1,2,3-oxadiazol-5-yl | thiophen-2-yl |
| H | 1,2,3-thiadiazol-3-yl | thiophen-2-yl |
| H | 1,2,3-thiadiazol-5-yl | thiophen-2-yl |
| H | 1,2,3,4-tetrazol-1-yl | thiophen-2-yl |
| H | 1,2,3,4-tetrazol-5-yl | thiophen-2-yl |
| H | 1,2,3,5-tetrazol-1-yl | thiophen-2-yl |
| H | 1,2,3,5-tetrazol-4-yl | thiophen-2-yl |
| H | pyridin-2-yl | thiophen-2-yl |
| H | pyridin-3-yl | thiophen-2-yl |
| H | thiophen-2-yl | pyridin-3-yl |
| H | pyridin-4-yl | thiophen-2-yl |
| H | pyrimidin-2-yl | thiophen-2-yl |
| H | pyrimidin-5-yl | thiophen-2-yl |
| H | pyrimidin-4-yl | thiophen-2-yl |
| H | pyrazin-2-yl | thiophen-2-yl |
| H | pyridazin-3-yl | thiophen-2-yl |
| H | pyridazin-4-yl | thiophen-2-yl |
| H | 1,3,5-triazin-2-yl | thiophen-2-yl |
| H | 1,2,4-triazin-3-yl | thiophen-2-yl |
| H | 1,2,4-triazin-5-yl | thiophen-2-yl |
| H | 1,2,4-triazin-6-yl | thiophen-2-yl |
| H | benzothiophen-2-yl | thiophen-2-yl |
| H | benzothiophen-3-yl | thiophen-2-yl |
| H | benzothiophen-4-yl | thiophen-2-yl |
| H | benzothiophen-5-yl | thiophen-2-yl |
| H | benzothiophen-6-yl | thiophen-2-yl |
| H | benzothiophen-7-yl | thiophen-2-yl |
| H | benzofuran-2-yl | thiophen-2-yl |
| H | benzofuran-3-yl | thiophen-2-yl |
| H | benzofuran-4-yl | thiophen-2-yl |
| H | benzofuran-5-yl | thiophen-2-yl |
| H | benzofuran-6-yl | thiophen-2-yl |
| H | benzofuran-7-yl | thiophen-2-yl |
| H | indol-1-yl | thiophen-2-yl |
| H | indol-2-yl | thiophen-2-yl |
| H | indol-3-yl | thiophen-2-yl |
| H | indol-4-yl | thiophen-2-yl |
| H | indol-5-yl | thiophen-2-yl |
| H | indol-6-yl | thiophen-2-yl |
| H | indol-7-yl | thiophen-2-yl |
| H | benzoxazol-2-yl | thiophen-2-yl |
| H | benzoxazol-4-yl | thiophen-2-yl |
| H | benzoxazol-5-yl | thiophen-2-yl |
| H | benzoxazol-6-yl | thiophen-2-yl |
| H | benzoxazol-7-yl | thiophen-2-yl |
| H | benzothiazol-2-yl | thiophen-2-yl |
| H | benzothiazol-4-yl | thiophen-2-yl |
| H | benzothiazol-5-yl | thiophen-2-yl |
| H | benzothiazol-6-yl | thiophen-2-yl |
| H | benzothiazol-7-yl | thiophen-2-yl |
| H | benzimidazol-1-yl | thiophen-2-yl |
| H | benzimidazol-2-yl | thiophen-2-yl |
| H | benzimidazol-4-yl | thiophen-2-yl |
| H | benzimidazol-5-yl | thiophen-2-yl |
| H | benzimidazol-6-yl | thiophen-2-yl |
| H | benzimidazol-7-yl | thiophen-2-yl |
| H | benzisoxazol-3-yl | thiophen-2-yl |
| H | benzisoxazol-4-yl | thiophen-2-yl |
| H | benzisoxazol-5-yl | thiophen-2-yl |
| H | benzisoxazol-6-yl | thiophen-2-yl |
| H | benzisoxazol-7-yl | thiophen-2-yl |
| H | benzisothiazol-3-yl | thiophen-2-yl |
| H | benzisothiazol-4-yl | thiophen-2-yl |
| H | benzisothiazol-5-yl | thiophen-2-yl |
| H | benzisothiazol-6-yl | thiophen-2-yl |
| H | benzisothiazol-7-yl | thiophen-2-yl |
| H | indazol-1-yl | thiophen-2-yl |

TABLE 4-continued

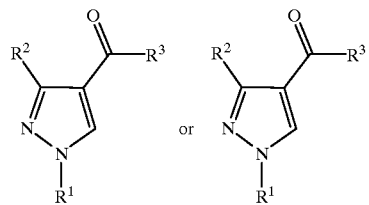

| R¹ | R² | R³ |
|---|---|---|
| H | indazol-3-yl | thiophen-2-yl |
| H | indazol-4-yl | thiophen-2-yl |
| H | indazol-5-yl | thiophen-2-yl |
| H | indazol-6-yl | thiophen-2-yl |
| H | indazol-7-yl | thiophen-2-yl |
| H | quinolin-2-yl | thiophen-2-yl |
| H | quinolin-3-yl | thiophen-2-yl |
| H | quinolin-4-yl | thiophen-2-yl |
| H | quinolin-5-yl | thiophen-2-yl |
| H | quinolin-6-yl | thiophen-2-yl |
| H | quinolin-7-yl | thiophen-2-yl |
| H | quinolin-8-yl | thiophen-2-yl |
| H | isoquinolin-1-yl | thiophen-2-yl |
| H | isoquinolin-3-yl | thiophen-2-yl |
| H | isoquinolin-4-yl | thiophen-2-yl |
| H | isoquinolin-5-yl | thiophen-2-yl |
| H | isoquinolin-6-yl | thiophen-2-yl |
| H | isoquinolin-7-yl | thiophen-2-yl |
| H | isoquinolin-8-yl | thiophen-2-yl |
| H | quinazolin-2-yl | thiophen-2-yl |
| H | quinazolin-4-yl | thiophen-2-yl |
| H | quinazolin-5-yl | thiophen-2-yl |
| H | quinazolin-6-yl | thiophen-2-yl |
| H | quinazolin-7-yl | thiophen-2-yl |
| H | quinazolin-8-yl | thiophen-2-yl |
| H | quinoxalin-2-yl | thiophen-2-yl |
| H | quinoxalin-5-yl | thiophen-2-yl |
| H | quinoxalin-6-yl | thiophen-2-yl |
| H | phthalazin-1-yl | thiophen-2-yl |
| H | phthalazin-5-yl | thiophen-2-yl |
| H | phthalazin-6-yl | thiophen-2-yl |
| H | cinnolin-3-yl | thiophen-2-yl |
| H | cinnolin-4-yl | thiophen-2-yl |
| H | cinnolin-5-yl | thiophen-2-yl |
| H | cinnolin-6-yl | thiophen-2-yl |
| H | cinnolin-7-yl | thiophen-2-yl |
| H | cinnolin-8-yl | thiophen-2-yl |
| H | 1,2,4-benzotriazin-3-yl | thiophen-2-yl |
| H | 1,2,4-benzotriazin-5-yl | thiophen-2-yl |
| H | 1,2,4-benzotriazin-6-yl | thiophen-2-yl |
| H | 1,2,4-benzotriazin-7-yl | thiophen-2-yl |
| H | 1,2,4-benzotriazin-8-yl | thiophen-2-yl |
| H | 1-methyl-3,5-dichloropyrazol-4-yl | Ph |
| H | 1-methyl-3,5-dichloropyrazol-4-yl | thiophen-2-yl |
| H | Ph | 1-methyl-3,5-dichloropyrazol-4-yl |
| H | thiophen-2-yl | 1-methyl-3,5-dichloropyrazol-4-yl |
| H | 1-methyl-5-chloropyrazol-4-yl | Ph |
| H | 1-methyl-5-chloropyrazol-4-yl | thiophen-2-yl |
| H | Ph | 1-methyl-5-chloropyrazol-4-yl |
| H | thiophen-2-yl | 1-methyl-5-chloropyrazol-4-yl |
| H | 2,6-dichloropyridin-4-yl | Ph |
| H | 2,6-dichloropyridin-4-yl | thiophen-2-yl |
| H | Ph | 2,6-dichloropyridin-4-yl |
| H | thiophen-2-yl | 2,6-dichloropyridin-4-yl |
| MeCO | 2-naphthyl | Ph |
| MeCO | 2-naphthyl | thiophen-2-yl |
| MeSO² | 2-naphthyl | Ph |
| MeSO₂ | 2-naphthyl | thiophen-2-yl |

TABLE 4-continued

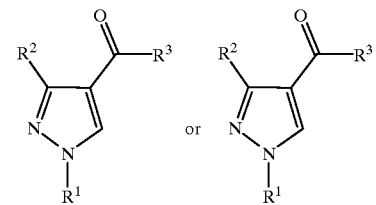

| R¹ | R² | R³ |
|---|---|---|
| Me²NCO | 2-naphthyl | Ph |
| Me₂NCO | 2-naphthyl | thiophen-2-yl |
| Me₂NSO₂ | 2-naphthyl | Ph |
| Me₂NSO₂ | 2-naphthyl | thiophen-2-yl |
| MeNHCO | 2-naphthyl | Ph |
| MeNHCO | 2-naphthyl | thiophen-2-yl |
| Et₂NSO₂ | 2-naphthyl | Ph |
| Et₂NSO₂ | 2-naphthyl | thiophen-2-yl |
| MeOCH₂ | 2-naphthyl | Ph |
| MeOCH₂ | 2-naphthyl | thiophen-2-yl |

TABLE 5

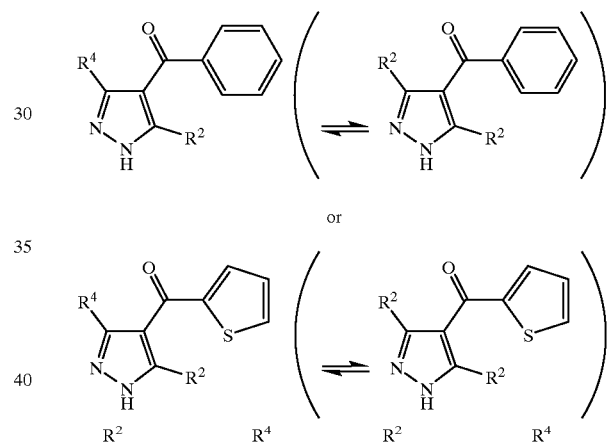

| R² | R⁴ | R² | R⁴ |
|---|---|---|---|
| 3-F | Cl | 3-Me | Me |
| 3-Cl | Cl | 3-OCF₃ | Me |
| 3-Br | Cl | 3-OCClF₂ | Me |
| 3-I | Cl | 3-OCBrF₂ | Me |
| 3-Me | Cl | 3,4-Cl₂ | Me |
| 3-OCF₃ | Cl | 3-Cl-4-F | Me |
| 3-OCClF₂ | Cl | 3-CF₃ | Me |
| 3-OCBrF₂ | Cl | 3,5-Cl₂ | Me |
| 3,4-Cl₂ | Cl | 3-Cl-4-F | Me |
| 3-Cl-4-F | Cl | 3,4,5-Cl₃ | Me |
| 3-CF₃ | Cl | 3,5-Cl₂-4-Br | Me |
| 3,5-Cl₂ | Cl | 3,5-Cl₂-4-I | Me |
| 3-Cl-4-F | Cl | 3,5-(CF₃)₂ | Me |
| 3,4,5-Cl₃ | Cl | 3,5-Cl₂-4-F | Me |
| 3,5-Cl₂-4-Br | Cl | 3,5-Br₂-4-Cl | Me |
| 3,5-Cl₂-4-I | Cl | 3,4,5-F₃ | Me |
| 3,5-(CF₃)₂ | Cl | 3,4-F₂ | Me |
| 3,5-F₂ | Cl | 3,5-Br₂ | Me |
| 3,5-Cl₂-4-F | Cl | 3,5-Br₂-4-F | Me |
| 3,5-Br₂-4-Cl | Cl | 3-Br-5-I | Me |
| 3,4,5-F₃ | Cl | 3-F | MeO |
| 3,4-F₂ | Cl | 3-Cl | MeO |
| 3,5-Br₂ | Cl | 3-Br | MeO |
| 3,5-Br₂-4-F | Cl | 3-I | MeO |
| 3-Br-5-I | Cl | 3-Me | MeO |
| 3-F | Me | 3-OCF₃ | MeO |
| 3-Cl | Me | 3-OCClF₂ | MeO |
| 3-Br | Me | 3-OCBrF₂ | MeO |
| 3-I | Me | | |

TABLE 5-continued

| $R^2$ | $R^4$ | $R^2$ | $R^4$ |
|---|---|---|---|
| 3,4-Cl$_2$ | MeO | 3-Cl-4-F | MeS |
| 3-Cl-4-F | MeO | 3,4,5-Cl$_3$ | MeS |
| 3-CF$_3$ | MeO | 3,5-Cl$_2$-4-Br | MeS |
| 3,5-Cl$_2$ | MeO | 3,5-Cl$_2$-4-I | MeS |
| 3-Cl-4-F | MeO | 3,5-(CF$_3$)$_2$ | MeS |
| 3,4,5-Cl$_3$ | MeO | 3,5-F$_2$ | MeS |
| 3,5-Cl$_2$-4-Br | MeO | 3,5-Cl$_2$-4-F | MeS |
| 3,5-Cl$_2$-4-I | MeO | 3,5-Br$_2$-4-Cl | MeS |
| 3,5-(CF$_3$)$_2$ | MeO | 3,4,5-F$_3$ | MeS |
| 3,5-F$_2$ | MeO | 3,4-F$_2$ | MeS |
| 3,5-Cl$_2$-4-F | MeO | 3,5-Br$_2$ | MeS |
| 3,5-Br$_2$-4-Cl | MeO | 3,5-Br$_2$-4-F | MeS |
| 3,4,5-F$_3$ | MeO | 3-Br-5-I | MeS |
| 3,4-F$_2$ | MeO | 3,5-Cl$_2$ | F |
| 3,5-Br$_2$ | MeO | 3,4,5-Cl$_3$ | F |
| 3,5-Br$_2$-4-F | MeO | 3,5-Cl$_2$-4-F | F |
| 3-Br-5-I | MeO | 3,5-Br$_2$-4-Cl | F |
| 3-F | MeS | 3,5-Br$_2$-4-F | F |
| 3-Cl | MeS | 3,5-Cl$_2$ | Br |
| 3-Br | MeS | 3,4,5-Cl$_3$ | Br |
| 3-I | MeS | 3,5-Cl$_2$-4-F | Br |
| 3-MeO | MeS | 3,5-Br$_2$-4-Cl | Br |
| 3-OCF$_3$ | MeS | 3,5-Br$_2$-4-F | Br |
| 3-OCClF$_2$ | MeS | 3,5-Cl$_2$ | I |
| 3-OCBrF$_2$ | MeS | 3,4,5-Cl$_3$ | I |
| 3,4-Cl$_2$ | MeS | 3,5-Cl$_2$-4-F | I |
| 3-Cl-4-F | MeS | 3,5-Br$_2$-4-Cl | I |
| 3-CF$_3$ | MeS | 3,5-Br$_2$-4-F | I |
| 3,5-Cl$_2$ | MeS | 3,5-Cl$_2$ | Et |
| 3,4,5-Cl$_3$ | Et | | |
| 3,5-Cl$_2$-4-F | Et | | |
| 3,5-Br$_2$-4-Cl | Et | | |
| 3,5-Br$_2$-4-F | Et | | |
| 3-F | Pr-n | | |
| 3-Cl | Pr-iso | | |
| 3-Br | Bu-n | | |
| 3-I | Bu-iso | | |
| 3-Me | Bu-sec | | |
| 3-OCF$_3$ | Bu-tert | | |
| 3-OCClF$_2$ | OEt | | |
| 3-OCBrF$_2$ | OPr-n | | |
| 3,4-Cl$_2$ | OPr-iso | | |
| 3-Cl-4-F | OBu-n | | |
| 3-CF$_3$ | OBu-iso | | |
| 3,5-Cl$_2$ | OBu-sec | | |
| 3-Cl-4-F | OBu-tert | | |
| 3,4,5-Cl$_3$ | SPr-n | | |
| 3,5-Cl$_2$-4-Br | SPr-iso | | |
| 3,5-Cl$_2$-4-I | SBu-n | | |
| 3,5-(CF$_3$)$_2$ | SBu-iso | | |
| 3,5-F$_2$ | SBu-sec | | |
| 3,5-Cl$_2$-4-F | SBu-tert | | |

In use of the compounds of the present invention as a herbicide, they may be usually mixed with an appropriate carrier, for example, a solid carrier such as clay, talc, bentonite, diatomaceous earth and white carbon; or a liquid carrier such as water, alcohols (isopropanol, butanol, benzyl alcohol, furfuryl alcohol, etc.), aromatic hydrocarbons (toluene, xylene, etc.), ethers (anisole, etc.), ketones (cyclohexanone, isophorone, etc.), esters (butyl acetate, etc.), acid amides (N-methylpyrrolidone, etc.), and halogenated hydrocarbons (chlorobenzene, etc.). Also, if necessary, they may be added with a suitable adjuvant such as surfactant, emulsifier, dispersant, penetrating agent, spreader, thickener, anti-freezing agent, coagulation preventing agent, stabilizer and the like, and can be practically used in various forms of formulation such as liquid formulation, emulsifiable concentrate, wettable powder, dry flowable, flowable, dust or granule.

The compounds of the present invention may be mixed, if necessary, with other kinds of herbicide, various kinds of insecticide, fungicide, plant growth regulator, synergist and the like in the course of formulating process or at the time of application.

In particular, combined application of the compound of the present invention with other herbicide(s) can result in reducing the cost through decrease of the application rate, expanding the weeding spectrum and improving herbicidal performance through synergistic effect between combined herbicides. In this connection, the compound of the present invention may be combined with two or more known herbicides. As the kinds of herbicides which can be combined with the compound of the present invention in use thereof, there can be mentioned, for instance, the compounds described in Farm Chemicals Handbook (1994).

The application rate of the compound of the present invention as a herbicide is variable depending on the place, time and method of its application, and the crop to be treated and the like. It is, however, generally appropriate to apply the compound of the present invention as the active ingredient in an amount of about 0.0001–50 kg/ha, preferably about 0.001–20 kg/ha.

Shown below are the examples of formulations using the compounds of the present invention. It should be understood, however, that the formulations coming within the concept of the present invention are not limited to shown below. In the following description of the examples of formulations, all "parts" are by weight unless otherwise noted.

Wettable Powder

|  | Parts |
|---|---|
| Compound of the present invention | 5–80 |
| Solid carrier | 10–85 |
| Surfactant | 1–10 |
| Others | 1–5 |

(Others include coagulation preventing agent and the like.)

Emulsifiable Concentrate

|  | Parts |
|---|---|
| Compound of the present invention | 1–30 |
| Liquid carrier | 55–95 |
| Surfactant | 5–15 |

Flowable

|  | Parts |
|---|---|
| Compound of the present invention | 5–70 |
| Liquid carrier | 15–65 |
| Surfactant | 5–12 |
| Others | 5–30 |

(Others include anti-freezing agent, thickener and the like.)

Granular Wettable Powder (Dry Flowable)

|  | Parts |
|---|---|
| Compound of the present invention | 20–90 |
| Solid carrier | 9–60 |
| Surfactant | 1–20 |

Granule

|  | Parts |
|---|---|
| Compound of the present invention | 0.01–10 |
| Solid carrier | 90–99.99 |
| Others | 0–5 |

Formulation Example 1; Wettable Powder

|  | Parts |
|---|---|
| Compound 1 of the present invention | 50 |
| Zeeklite PFP (trademark) | 43 |
| (kaolin type clay: mfd. by Zeeklite Industries Co., Ltd.) | |
| Sorpol 5050 (trademark) | 2 |
| (anionic surfactant: mfd. by Toho Chemical Co., Ltd.) | |
| Runox 1000 C (trademark) | 3 |
| (anionic surfactant: mfd. by Toho Chemical Co., Ltd.) | |
| Carplex #80 (trademark: coagulation preventing agent) | 2 |
| (white carbon: mfd. by Shionogi Pharmaceutical Co., Ltd.) | |

The above ingredients are homogeneously blended and ground to formulate a wettable powder.

Formulation Example 2: Emulsifiable Concentrate

|  | Parts |
|---|---|
| Compound 1 of the present invention | 3 |
| Xylene | 76 |
| Isophorone | 15 |
| Sorpol 3005 X (trademark) | 6 |

(mixture of nonionic and anionic surfactants: mfd. by Toho Chemical Co., Ltd.)

The above ingredients are homogeneously blended to formulate an emulsifiable concentrate.

Formulation Example 3; Flowable

|  | Parts |
|---|---|
| Compound 1 of the present invention | 35 |
| Agrizole S-711 (trademark) | 8 |
| (nonionic surfactant: mfd. by Kao Corporation) | |

-continued

|  | Parts |
|---|---|
| Runox 1000 C (trademark) | 0.5 |
| (anionic surfactant: mfd. by Toho Chemical Co., Ltd.) | |
| 1% Rodopol water (trademark) | 20 |
| (thickener: mfd. by Rhone-Poulenc) | |
| Ethylene glycol (anti-freezing agent) | 8 |
| Water | 28.5 |

The above ingredients are homogeneously blended to formulate a flowable.

Formulation Example 4; Granular Wettable Powder (Dry Flowable)

|  | Parts |
|---|---|
| Compound 1 of the present invention | 75 |
| Isobam No. 1 (trademark) | 10 |
| (anionic surfactant: mfd. by Kuraray Isoprene Chemical Co., Ltd.) | |
| Vanilex N (trademark) | 5 |
| (anionic surfactant: mfd. by Sanyo Kokusaku Pulp K.K.) | |
| Carplex #80 (trademark) | 10 |
| (white carbon: mfd. by Shionogi Pharmaceutical Co., Ltd.) | |

The above ingredients are homogeneously blended and pulverized to formulate a dry flowable.

Formulation Example 5; Granules

|  | Parts |
|---|---|
| Compound 1 of the present invention | 0.1 |
| Bentonite | 55.0 |
| Talc | 44.9 |

The above ingredients are homogeneously blended and ground, to which then a small amount of water is added, and the resulting mixture is kneaded with stirring, granulated by an extrusion granulator and dried to formulate granules.

In practical use of the above formulations, the wettable powder, emulsifiable concentrate, flowable and granular wettable powder are diluted 50–1000 times with water and then applied so that the active ingredient will be supplied at a level of 1 to 10,000 ppm, or at a rate of 0.0001 to 10 kg per hectare.

The following test examples specifically illustrate the utility of the compound of the present invention as an active ingredient of herbicides.

Test Example 1: Test on Herbicidal Effect by Soil Treatment

A sterilized diluvial soil was placed in a 21 cm×13 cm×7 cm plastic cases. Each of seeds of velvetleaf (*Abutilon theophrasti*), redroot (*Amaranthus retroflexus*), common chickweed (*Stellaria media*), corn, soybean, cotton and wheat was sown spotwise, and covered with soil to the depth of about 1.5 cm, and then a spray liquid of test compound was uniformly applied over the soil surface by a small-sized sprayer so that the active ingredient would be supplied at the predetermined rate. Each of the spray liquid was prepared by diluting with water a formulation suitably prepared according to the relevant Formulation Examples described above, and was applied all over the soil surface. Three weeks after the application of each compound, its herbicidal effects on the said crops and weeds were examined and evaluated according to the following standard ratings. The results are shown in Table 6.

Standard Rating

5: Growth control rate is more than 90%.
(or plants are almost completely withered)
4: Growth control rate is 70 to 90%.
3: Growth control rate is 40 to 70%.
2: Growth control rate is 20 to 40%.
1: Growth control rate is 5 to 20%.
0: Growth control rate is less than 5%.

Test Example 2: Test on Herbicidal Effect by Foliage Treatment

A sterilized diluvial soil was placed in a 21 cm×13 cm×7 cm plastic cases. Each of seeds of velvetleaf (*Abutilon theophrasti*), cocklebur (*Xanthium pensylvanicum*), redroot (*Amaranthus retroflexus*), common chickweed (*Stellaria media*), corn, soybean, cotton and wheat was sown spotwise and covered with soil to the depth of about 1.5 cm. When each of the plants grew to the 2- to 3-leaf stage, a spray liquid of test compound was uniformly applied to the foliage of the plants so that the active ingredient would be supplied at the predetermined rate. Each of the spray liquid was prepared by diluting with water a wettable powder suitably prepared according to the relevant Formula Examples described above, and was applied to the whole area of the foliage of the plants using a small-sized sprayer. Three weeks after the application of each compound, its herbicidal effects on the said crops and weeds were examined and evaluated according to the same standard ratings as used in Test Example 1. The results are shown in Table 7.

In Tables 6 and 7, the symbols represent the following; A: velvetleaf (*Abutilon theophrasti*), B: redroot (*Amaranthus retroflexus*), C: common chickweed (*Stellaria media*), D: cocklebur (*Xanthium pensylvanicum*), a: soybean, b: cotton, C: corn, and d: wheat.

TABLE 6

| Compound No. | Rate (kg/ha) | A | B | C | a | b | c | d |
|---|---|---|---|---|---|---|---|---|
| 2 | 5.0 | 5 | 5 | 5 | 0 | 0 | 0 | 0 |
| 8 | 5.0 | 5 | 5 | 5 | 0 | 0 | 0 | 0 |
| 11 | 5.0 | 5 | 5 | 5 | 0 | 0 | 0 | 0 |
| 13 | 5.0 | 5 | 5 | 5 | 0 | 0 | 0 | 0 |
| 15 | 5.0 | 5 | 5 | 5 | 0 | 0 | 0 | 0 |
| 16/17 (3/1) | 5.0 | 5 | 5 | 5 | 0 | 0 | 0 | 0 |
| 20/21 (5/1) | 5.0 | 5 | 5 | 5 | 0 | 0 | 0 | 0 |
| 22 | 5.0 | 5 | 5 | 5 | 0 | 0 | 0 | 0 |
| 24 | 5.0 | 5 | 5 | 5 | 0 | 0 | 0 | 0 |
| 26 | 5.0 | 5 | 5 | 5 | 0 | 0 | 0 | 0 |
| 32 | 2.5 | 4 | 5 | 5 | 0 | 0 | 0 | 0 |
| 34 | 2.5 | 4 | 5 | 5 | 0 | 0 | 0 | 0 |
| 35 | 2.5 | 2 | 4 | 5 | 0 | 0 | 0 | 0 |
| 38 | 2.5 | 2 | 5 | 5 | 0 | 0 | 0 | 0 |
| 42 | 2.5 | 0 | 3 | 3 | 0 | 0 | 0 | 0 |
| 48 | 2.5 | 3 | 5 | 5 | 0 | 0 | 0 | 0 |
| 54 | 2.5 | 3 | 5 | 5 | 0 | 0 | 0 | 0 |
| 56 | 5.0 | 0 | 5 | 5 | 0 | 0 | 0 | 0 |
| 57 | 2.5 | 1 | 3 | 3 | 0 | 0 | 0 | 0 |
| 58 | 2.5 | 2 | 3 | 2 | 0 | 0 | 0 | 0 |
| 59/60 (3/1) | 2.5 | 3 | 3 | 5 | 0 | 0 | 0 | 0 |
| 61 | 2.5 | 5 | 5 | 5 | 0 | 0 | 0 | 0 |
| 65 | 2.5 | 5 | 5 | 5 | 0 | 0 | 0 | 0 |
| 66 | 2.5 | 5 | 3 | 5 | 0 | 0 | 0 | 0 |
| 67/68 (7/3) | 2.5 | 3 | 2 | 5 | 0 | 0 | 0 | 0 |
| 69 | 2.5 | 5 | 5 | 5 | 0 | 0 | 0 | 0 |
| 70 | 2.5 | 0 | 5 | 5 | 0 | 0 | 0 | 0 |
| 71 | 2.5 | 1 | 5 | 2 | 0 | 0 | 0 | 0 |
| 74 | 2.5 | 4 | 0 | 5 | 0 | 0 | 0 | 0 |

TABLE 7

| Compound No. | Rate (kg/ha) | A | B | C | D | a | b | c | d |
|---|---|---|---|---|---|---|---|---|---|
| 2 | 5.0 | 5 | 5 | 5 | 5 | 0 | 0 | 0 | 0 |
| 3 | 5.0 | 5 | 5 | 5 | 5 | 0 | 0 | 0 | 0 |
| 4 | 5.0 | 5 | 0 | 5 | 5 | 0 | 0 | 0 | 0 |
| 5 | 5.0 | 4 | 5 | 5 | 0 | 0 | 0 | 0 | 0 |
| 8 | 5.0 | 5 | 5 | 5 | 5 | 0 | 0 | 0 | 0 |
| 11 | 5.0 | 5 | 5 | 5 | 5 | 0 | 0 | 0 | 0 |
| 12 | 5.0 | 0 | 0 | 5 | 0 | 0 | 0 | 0 | 0 |
| 13 | 5.0 | 5 | 5 | 5 | 5 | 0 | 0 | 0 | 0 |
| 14 | 5.0 | 0 | 2 | 3 | 1 | 0 | 0 | 0 | 0 |
| 15 | 5.0 | 5 | 5 | 5 | 5 | 0 | 0 | 0 | 0 |
| 16/17 (3/1) | 5.0 | 5 | 5 | 5 | 5 | 0 | 0 | 0 | 0 |
| 18/19 (1/1) | 5.0 | 3 | 2 | 5 | 3 | 0 | 0 | 0 | 0 |
| 20/21 (5/1) | 5.0 | 5 | 5 | 5 | 5 | 0 | 0 | 0 | 0 |
| 22 | 5.0 | 5 | 5 | 5 | 5 | 0 | 0 | 0 | 0 |
| 24 | 5.0 | 5 | 5 | 5 | 5 | 0 | 0 | 0 | 0 |
| 25 | 5.0 | 5 | 5 | 5 | 5 | 0 | 0 | 0 | 0 |
| 26 | 5.0 | 5 | 5 | 5 | 5 | 0 | 0 | 0 | 0 |
| 27 | 5.0 | 5 | 5 | 5 | 5 | 0 | 0 | 0 | 0 |
| 32 | 2.5 | 5 | 5 | 5 | 5 | 0 | 0 | 0 | 0 |
| 34 | 2.5 | 5 | 5 | 5 | 5 | 0 | 0 | 0 | 0 |
| 35 | 2.5 | 5 | 5 | 5 | 5 | 0 | 0 | 0 | 0 |
| 38 | 2.5 | 1 | 5 | 5 | 1 | 0 | 0 | 0 | 0 |
| 42 | 2.5 | 4 | 5 | 5 | 3 | 0 | 0 | 0 | 0 |
| 43 | 2.5 | 4 | 5 | 5 | 2 | 0 | 0 | 0 | 0 |
| 48 | 2.5 | 5 | 5 | 5 | 5 | 0 | 0 | 0 | 0 |
| 52 | 5.0 | 3 | 4 | 1 | 4 | 0 | 1 | 0 | 0 |
| 53 | 1.9 | 5 | 5 | 5 | 5 | 0 | 5 | 0 | 0 |
| 54 | 2.5 | 5 | 5 | 5 | 5 | 0 | 0 | 0 | 0 |
| 56 | 5.0 | 5 | 5 | 5 | 3 | 0 | 2 | 0 | 0 |
| 57 | 2.5 | 5 | 5 | 5 | 4 | 0 | 0 | 0 | 0 |
| 58 | 2.5 | 5 | 5 | 5 | 4 | 0 | 1 | 0 | 0 |
| 59/60 (3/1) | 2.5 | 5 | 5 | 5 | 5 | 0 | 0 | 0 | 0 |
| 61 | 2.5 | 5 | 5 | 5 | 5 | 0 | 0 | 0 | 0 |
| 62 | 2.5 | 3 | 2 | 5 | 3 | 0 | 0 | 0 | 0 |
| 65 | 2.5 | 5 | 5 | 5 | 5 | 0 | 1 | 0 | 0 |
| 66 | 2.5 | 5 | 5 | 5 | 5 | 1 | 0 | 0 | 0 |
| 61/68 (7/3) | 2.5 | 5 | 5 | 5 | 5 | 0 | 0 | 0 | 0 |
| 69 | 2.5 | 5 | 5 | 5 | 5 | 1 | 0 | 0 | 0 |
| 70 | 2.5 | 5 | 5 | 5 | 5 | 1 | 0 | 0 | 0 |
| 71 | 2.5 | 5 | 5 | 5 | 5 | 0 | 0 | 0 | 0 |
| 72 | 2.5 | 0 | 5 | 3 | 1 | 0 | 0 | 0 | 0 |
| 74 | 2.5 | 5 | 5 | 5 | 5 | 0 | 1 | 0 | 0 |

We claim:

1. A pyrazole derivative represented by the general formula (1a) or (1b):

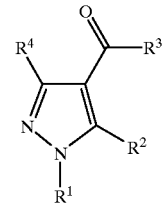

(1a)

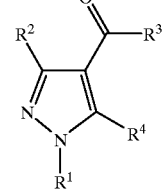

(1b)

wherein $R^1$ represents a hydrogen atom;

$R^2$ represents:

a phenyl group which may be substituted with one or more substituents selected from a halogen atom, a $C_{1-4}$ alkyl, $C_{1-4}$ alkoxy, $C_{1-4}$ haloalkyl, $C_{1-4}$ haloalkoxy, di-$C_{1-4}$ alkylamino, cyano, nitro, $C_{1-4}$ alkoxy-carbonyl, phenyl or phenoxy group;

a 1-naphthyl group which may be substituted with one or more substituents selected from a halogen atom or a $C_{1-4}$ alkyl group; or a 2-naphthyl group which may be substituted with one or more substituents selected from a halogen atom or a $C_{1-4}$ alkyl group;

$R^3$ represents a thiophen-2-yl group; and $R^4$ represents a hydrogen atom.

2. The pyrazole derivative according to claim 1, wherein $R^2$ represents a phenyl or 2-naphthyl group which may be substituted with one or more substituents selected from a halogen atom or a $C_{1-4}$ alkyl, $C_{1-4}$ alkoxy, $C_{1-4}$ haloalkyl, $C_{1-4}$ haloalkoxy, di-$C_{1-4}$ alkylamino, cyano, nitro, phenyl or phenoxy group; and $R^3$ represents a thiophen-2-yl group.

3. The pyrazole derivative according to claim 1, wherein $R^2$ represents a 3-substituted-phenyl, 4-substituted-phenyl, 3,4-disubstituted-phenyl, 3,5-disubstituted-phenyl or 3,4,5-trisubstituted-phenyi group which may be substituted with one, two or three substituents selected from a halogen atom or a $C_{1-4}$ alkyl, $C_{1-4}$ alkoxy, $C_{1-4}$ haloalkyl, $C_{1-4}$ haloalkoxy, di-$C_{1-4}$ alkylamino, cyano, nitro, phenyl or phenoxy group.

4. A herbicide composition comprising as an active ingredient one or more pyrazole derivatives according to claim 1.

* * * * *